US009295559B2

(12) United States Patent (10) Patent No.: US 9,295,559 B2
Farris (45) Date of Patent: Mar. 29, 2016

(54) TISSUE SPACER IMPLANT

(75) Inventor: Jeffrey A. Farris, Berne, IN (US)

(73) Assignee: MEDIVEST, LLC, Columbia City, IN (US)

(*) Notice: Subject to any disclaimer, the term of this patent is extended or adjusted under 35 U.S.C. 154(b) by 226 days.

(21) Appl. No.: 13/099,950

(22) Filed: May 3, 2011

(65) Prior Publication Data

US 2011/0208306 A1    Aug. 25, 2011

Related U.S. Application Data

(63) Continuation of application No. PCT/US2010/056234, filed on Nov. 10, 2010.

(60) Provisional application No. 61/259,866, filed on Nov. 10, 2009, provisional application No. 61/260,630, filed on Nov. 12, 2009.

(51) Int. Cl.
*A61F 2/44*        (2006.01)
*A61F 2/46*        (2006.01)
*A61F 2/30*        (2006.01)

(52) U.S. Cl.
CPC .................. *A61F 2/44* (2013.01); *A61F 2/4611* (2013.01); *A61F 2/30744* (2013.01); *A61F 2/442* (2013.01); *A61F 2/4637* (2013.01); *A61F 2002/302* (2013.01); *A61F 2002/305* (2013.01); *A61F 2002/30235* (2013.01); *A61F 2002/30354* (2013.01); *A61F 2002/30387* (2013.01); *A61F 2002/30484* (2013.01); *A61F 2002/30492* (2013.01); *A61F 2002/30507* (2013.01); *A61F 2002/30594* (2013.01); *A61F 2002/30604* (2013.01); *A61F 2002/30616* (2013.01); *A61F 2002/30617* (2013.01); *A61F 2002/30774* (2013.01); *A61F 2002/30787* (2013.01); *A61F 2002/4475* (2013.01); *A61F 2002/4629* (2013.01); *A61F 2310/00017* (2013.01); *A61F 2310/00023* (2013.01)

(58) Field of Classification Search
CPC ............................................. A61F 2/44–2/447
USPC ........................................... 623/17.11–17.16
See application file for complete search history.

(56) References Cited

U.S. PATENT DOCUMENTS 2,333,033 A   10/1943  Mraz
4,386,603 A    6/1983  Mayfield
5,702,453 A   12/1997  Rabbe et al.
(Continued)

FOREIGN PATENT DOCUMENTS

WO    2004037067 A2    5/2004

*Primary Examiner* — Jan Christopher Merene
*Assistant Examiner* — Steven Cotroneo
(74) *Attorney, Agent, or Firm* — Heslin Rothenberg Farley & Mesiti P.C.

(57) ABSTRACT

Tissue spacer implants, surgical distraction instruments, surgical insertion tools, coupling devices, surgical kits, surgical methods for distraction, and methods for coupling bodies are disclosed. The tissue spacer implants include a first end member, a second end member, and an intermediate spacer member having a coupling mechanism adapted to couple the first end member with the intermediate spacer member and to couple the second end member with the intermediate spacer member. The surgical instruments may be used for inserting these implants and include a first elongated member, a second elongated member, a distraction mechanism, and an actuator. The coupling devices may be used to couple the components of the implants.

32 Claims, 48 Drawing Sheets

(56) References Cited

U.S. PATENT DOCUMENTS

| | | | |
|---|---|---|---|
| 5,776,197 A | 7/1998 | Rabbe et al. | |
| 6,090,143 A * | 7/2000 | Meriwether et al. | 623/17.11 |
| 6,102,950 A * | 8/2000 | Vaccaro | 623/17.16 |
| 6,106,557 A * | 8/2000 | Robioneck et al. | 623/17.15 |
| 6,113,638 A * | 9/2000 | Williams et al. | 128/898 |
| 6,193,756 B1 | 2/2001 | Studer et al. | |
| 6,375,682 B1 * | 4/2002 | Fleischmann et al. | 623/17.12 |
| 6,808,538 B2 * | 10/2004 | Paponneau | 623/17.16 |
| 6,852,129 B2 * | 2/2005 | Gerbec et al. | 623/17.15 |
| 7,056,343 B2 | 6/2006 | Schäfer et al. | |
| 7,214,243 B2 * | 5/2007 | Taylor | 623/17.11 |
| 7,621,953 B2 | 11/2009 | Braddock, Jr. et al. | |
| 7,824,445 B2 | 11/2010 | Biro et al. | |
| 7,887,588 B2 * | 2/2011 | Rapp | 623/17.11 |
| 7,914,581 B2 | 3/2011 | Dickson et al. | |
| 8,182,537 B2 * | 5/2012 | Refai et al. | 623/17.16 |
| 8,268,002 B2 | 9/2012 | Blackwell et al. | |
| 2001/0032017 A1 * | 10/2001 | Alfaro et al. | 623/17.11 |
| 2004/0073314 A1 | 4/2004 | White et al. | |
| 2004/0122518 A1 * | 6/2004 | Rhoda | 623/17.11 |
| 2004/0153089 A1 | 8/2004 | Zdeblick et al. | |
| 2004/0172129 A1 | 9/2004 | Schafer et al. | |
| 2004/0254644 A1 | 12/2004 | Taylor | |
| 2005/0060034 A1 * | 3/2005 | Berry et al. | 623/17.11 |
| 2005/0075634 A1 | 4/2005 | Zucherman et al. | |
| 2005/0182416 A1 * | 8/2005 | Lim et al. | 606/90 |
| 2006/0015184 A1 | 1/2006 | Winterbottom et al. | |
| 2007/0073405 A1 * | 3/2007 | Verhulst et al. | 623/17.15 |
| 2007/0219562 A1 | 9/2007 | Slone et al. | |
| 2008/0021555 A1 * | 1/2008 | White et al. | 623/17.11 |
| 2008/0154379 A1 | 6/2008 | Steiner et al. | |
| 2008/0243254 A1 * | 10/2008 | Butler | 623/17.16 |
| 2009/0204215 A1 | 8/2009 | McClintock et al. | |

* cited by examiner

TISSUE SPACER IMPLANT

CROSS-REFERENCE TO RELATED APPLICATIONS

This application is a continuation of International Application No. PCT/US2010/56234 filed on Nov. 10, 2010, which claims priority to U.S. Provisional Patent Application 61/259,866 filed on Nov. 10, 2009 and U.S. Provisional Patent Application 61/260,630 filed on Nov. 12, 2009, the disclosures of which are incorporated by reference herein in their entirety.

TECHNICAL FIELD

The present invention relates generally to general surgery, dentistry, orthopaedic, and neurosurgical implants used for insertion within a space between hard and soft tissue structures, and more specifically, but not exclusively, concerns devices implanted within a bone to replace a resected, fractured, or diseased portion and to maintain or reestablish proper spacing between bone fragments.

BACKGROUND OF THE INVENTION

Damage or disease that affects the integral structure of a tissue or bone structure, such as a vertebral body within an individual's spinal column, may lead to neurologic impairment with possible permanent damage to the surrounding tissue. Maintaining or re-establishing proper anatomic spacing within a tissue or bone structure, such as the spinal column, is critical to ensuring continued functionality of the surrounding tissue and for the spinal column, the spinal cord and nerve roots and therefore, avoidance of long term serious neurological, vascular, or other systemic impairments.

Typically, spacer-type of devices have a fixed overall length and are implanted without the ability of the inserting instrument to adjust the size of the spacing required without using multiple insertion instrumentation. A need exists for a spacer-type implant and a multipurpose instrument to be used to implant a spacer-type implant that allows the surgeon to minimize the size of the surgical incision and facilitate the operative technique by allowing for distraction and implant insertion with one instrument only, thereby decreasing patient morbidity.

BRIEF SUMMARY OF THE INVENTION

Advancement of the state of tissue spacer devices and implants and the surgical management relating to the clinical presentation of missing or damaged bone fragments and other hard/soft tissue structures within the body is believed desirable. One example of an embodiment of the invention that satisfies the need for improvements to a tissue spacer device used to treat patients suffering from either diseased or damaged bone or other tissue structures includes two end members and a modular central or intermediate spacer that is of a fixed height or thickness. The aspects of the invention disclosed herein use a tissue spacer device that, among other things, eliminates torsional forces being applied at the device tissue/bone interface and maintains the desired optimized spacing between tissue/bone fragments and structures, while offering post-insertion stability.

One embodiment of the invention is a tissue spacer implant comprising or including a first end member having a first end configured to engage tissue, for example, bone, and a second end opposite the first end; a second end member having a first end configured to engage tissue and a second end opposite the first end; and an intermediate spacer member having a coupling mechanism adapted to couple the second end of the first end member with the intermediate spacer member and to couple the second end of the second end member with the intermediate member. In one aspect, the intermediate spacer member comprises a main body, and the coupling mechanism may comprise a first pair of projections from the main body adapted to engage the second end of the first end member, a second pair of projections from the main body adapted to engage the second end of the second end member; and means for deflecting at least one of the projections of the first pair of projections and at least one of the projections of the second pair of projections wherein the first the first pair of projections engages the second end of the first end member and the second pair of projections engages the second end of the second end member to couple the first end member to the second end member. In another aspect of the invention, the means for deflecting at least one of the projections of the first pair of projections, for example, a camming device, and at least one to the projections of the second pair of deflectable projections may comprise means for deflecting both of the projections of the first pair of projections and both of the projections of the second pair of projections.

In another aspect of the invention, the first pair of projections may be beveled and the recesses in the second end of the first end member are beveled and wherein the second pair of projections are beveled and the recesses in the second end of the second end member are beveled. For example, the first pair of projections may comprise dovetails and the second pair of projections may comprise dovetails.

In one aspect, the main body of the intermediate spacer member may comprise a hollow main body having longitudinal slit or separation, and wherein the means for deflecting at least one of the projections of the first pair of projections and at least one of the projections of the second pair of projections comprises a separation widening device, for example, threaded rod, adapted to be inserted into the longitudinal separation and widen the separation wherein at least one of the projections of the first pair of projections and at least one of the projections of the second pair of projections are deflected.

Another embodiment of the invention is a surgical method comprising or including exposing a space between a first tissue and a second tissue; inserting a first end member having and first end and a second end opposite the first end into the space wherein the first end of the first end member contacts the first tissue; inserting a second end member having and first end and a second end opposite the first end into the space wherein the first end of the second end member contacts the second tissue; determining a distance between the second end of the first end member and the second end of the second end member; obtaining an intermediate body member at least in part as a function of the distance determined; inserting the intermediate body member between the first end member and the second end member; and securing the intermediate body to the first end member and the second end member. In one aspect, securing the intermediate body comprises activating a coupling mechanism adapted to secure the first end member and the second end member to the intermediate body member. In another aspect, the activating a coupling mechanism may comprise deflecting a camming device, for example, a pin or threaded rod. In another aspect, inserting the intermediate body member between the first end member and the second end member may be practiced by sliding the intermediate body member along a surface of a tool. In a further aspect of this embodiment, obtaining an intermediate body member at least in part as a function of the distance determined may comprise selecting the intermediate body member from a plurality of intermediate body members at least in part as a function of the distance determined.

Another embodiment of this invention is a surgical instrument for inserting an implant between two tissue bodies, the surgical instrument comprising or including a first elongated member having a distal end and a proximal end adapted to receive a first end member of the implant; a second elongated member having a distal end and a proximal end adapted to receive a second end member of the implant; a distraction mechanism operatively connected to the first elongated member and the second elongated member, the distraction mechanism adapted to vary a separation between the first elongated member and the second elongated member; and an actuator operatively connected to the distraction mechanism and adapted to manipulate the distraction mechanism. In one aspect of this embodiment, the distraction mechanism may comprise a plurality of bar linkages pivotally mounted to the first elongated member and the second elongated member. In another aspect, at least one of the first elongated member and the second elongated member comprises a guide, for example, a rail, a ramp, or a channel, for inserting an intermediate spacer member between the first end member and the second end member. In another aspect, the first elongated member may comprise a first coupling device at the proximal end adapted to receive the first end member of the implant, and the second elongated member may comprise a second coupling device at the proximal end adapted to receive the second end member of the implant. In another aspect, the instrument may further comprise an indicator, for example, a translating or rotating indicator, that indicates a spacing between the first elongated member and the second elongated member.

A further embodiment of the invention is an insertion tool adapted to insert a component into a body, the insertion tool comprising or including an elongated rod have a first end and a second end opposite the first end, wherein the first end comprises a handle and the second end comprises a coupling device adapted to receive the component. In one aspect of this embodiment, the component may comprise an intermediate spacer member of an implant, and wherein the insertion tool is adapted to insert the intermediate spacer member between a first end member and a second end member of the implant. In another aspect, the insertion tool may further comprise an activation rod operatively connected to the coupling device. In another aspect, the activation rod may pass through the handle and terminate with a rotatable knob.

Another embodiment of the invention is a device for coupling a first body and a second body, for example, coupling an end members of a surgical implant to an intermediate member of a surgical implant, the device comprising or including a cylindrical body having a top surface and a bottom surface and an axially extending hole, the axially extending hole having a first end at the top surface and a second end at the bottom surface; a first coupling plate having a first side and a second side opposite the first side, the first coupling plate having a first projection extending from the first side and a projection extending from the second side having a first through hole having a first camming surface; a second coupling plate having a first side and a second side opposite the first side, the second coupling plate having a second projection extending from the first side and a projection extending from the second side having a second through hole having a second camming surface; and a camming device adapted to be received by the first through hole and the second through hole; wherein when the first coupling plate is inserted into the first end of the hole of the cylindrical body whereby the first projection extends at least partially over the top surface of the cylindrical body and the second coupling plate is inserted into the second end of the hole of the clinical body whereby the second projection extends at least partially over the bottom surface of the cylindrical body, and whereby the first through hole at least partially aligns with the second through hole, and wherein when the camming device is inserted into the first through hole and into the second through hole, contact between the camming device and the first camming surface and the second camming surface draws the first coupling plate and the second coupling plate together and compresses a portion of the first body between the first projection and the top surface and a portion of the second body between the second projection and the bottom surface to couple the first body to the second body. In one aspect of this embodiment, the camming device comprises a tapered pin, for example, a circular tapered pin or a non-circular tapered pin. In another aspect, the tapered pin is adapted to threadably engage a threaded hole in the cylindrical body.

A still further embodiment of the invention is a method of coupling a first body and a second body, for example, coupling an end member of a surgical implant to a intermediate member of a surgical implant, the method comprising or including providing a cylindrical body having a top surface and a bottom surface and an axially extending hole, the axially extending hole having a first end at the top surface and a second end at the bottom surface; inserting a first coupling plate into the first end of the hole in the cylindrical body, the first coupling having a first side and a second side opposite the first side and having a first projection extending from the first side and a projection extending from the second side, and having a first through hole having a first camming surface, wherein, when inserted, the first projection extends at least partially over the top surface of the cylindrical body; inserting a second coupling plate into the second end of the hole in the cylindrical body, the second coupling plate having a first side and a second side opposite the first side, and the second coupling plate having a second projection extending from the first side and a projection extending from the second side having a second through hole having a second camming surface, wherein, when inserted, the second projection extends at least partially over the bottom surface of the cylindrical body, and whereby the first through hole at least partially aligns with the second through hole; and inserting a camming device into the first through hole and the second through hole whereby the camming device contacts the first camming surface and the second camming surface and draws the first coupling plate and the second coupling plate together and compresses a portion of the first body between the first projection and the top surface and a portion of the second body between the second projection and the bottom surface to couple the first body to the second body. In one aspect of this embodiment, the camming device may comprise a tapered pin, for example, a circular tapered pin or a non-circular tapered pin. In another aspect, the tapered pin may be adapted to threadably engage a threaded hole in the cylindrical body.

A further embodiment of the invention is another device for coupling a first body and a second body, for example, coupling an end member of a surgical implant to an intermediate member of a surgical implant, the device comprising or including a cylindrical body having an outer surface, an axially extending hole, a longitudinal slit or separation from the outer surface to the axially extending hole and extending a length of the cylindrical body, a top surface having a pair of axial projections, for example, beveled or dovetailed projections, straddling the longitudinal slit, a bottom surface having a pair of axial projections, for example, beveled or dovetailed projections, straddling the longitudinal slit; and a camming device adapted to be inserted into the longitudinal slit in the cylindrical body; wherein, when the camming device is inserted into the longitudinal slit, the camming device at least partially expands the longitudinal slit whereby each of the pair of axial projections on the top surface deflect and engage the first body and each of the pair of axial projections on the bottom surface deflect and engage the second body to couple the first body with the second body. In one aspect of this embodiment, the cylindrical body further comprises a radially extending threaded hole passing at least partially through the longitudinal slit, and wherein the camming device comprises a threaded rod adapted to engage the radially extending threaded hole. In another aspect, the radially extending threaded hole comprises a tapered threaded hole.

Another embodiment of the invention is a method for coupling a first body and a second body, for example, coupling components of a surgical implant, the method comprising or including providing a cylindrical body having an outer surface, an axially extending hole, a longitudinal slit from the outer surface to the axially extending hole and extending a length of the cylindrical body, a top surface having a pair of axial projections straddling the longitudinal slit, a bottom surface having a pair of axial projections straddling the longitudinal slit; and inserting a camming device into the longitudinal slit in the cylindrical body wherein the camming device at least partially expands the longitudinal slit whereby each of the pair of axial projections on the top surface deflect and engage the first body and each of the pair of axial projections on the bottom surface deflect and engage the second body to couple the first body with the second body. In one aspect of this embodiment, the cylindrical body may further comprise a radially extending threaded hole passing at least partially through the longitudinal slit, and wherein inserting the camming device comprises inserting a threaded rod into the radially extending threaded hole. In another aspect, the pair of axial projections on the top surface and the pair of axial projections on the bottom surface may each comprise beveled or dovetailed projections.

An even further embodiment of the invention is a surgical kit comprising or including any one of the surgical instruments described above and; and one or more of the tissue spacer implants recited above. The kit may also include an insertion tool as recited above. In one aspect of this embodiment, the one or more tissue spacer implants may comprise at least one first end member, at least one second end member, and a plurality of intermediate spacer members of varying dimension. This aspect may also include an enclosure adapted to retain the surgical instrument and the one or more tissue spacer implants, and this aspect may also include an instruction manual describing use of the surgical instrument and one or more tissue spacer implants.

Further additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

DETAILED DESCRIPTION OF THE INVENTION

Disclosed herein are tissue spacer implants, insertion instruments used for distraction and implantation of the implants, coupling devices and methods, and surgical implantation methods.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an instrument positioned nearest the torso, while "distal" indicates the part of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Also, the terms "implant" and "device" may be used interchangeably and have the same meaning herein.

Figure 1:
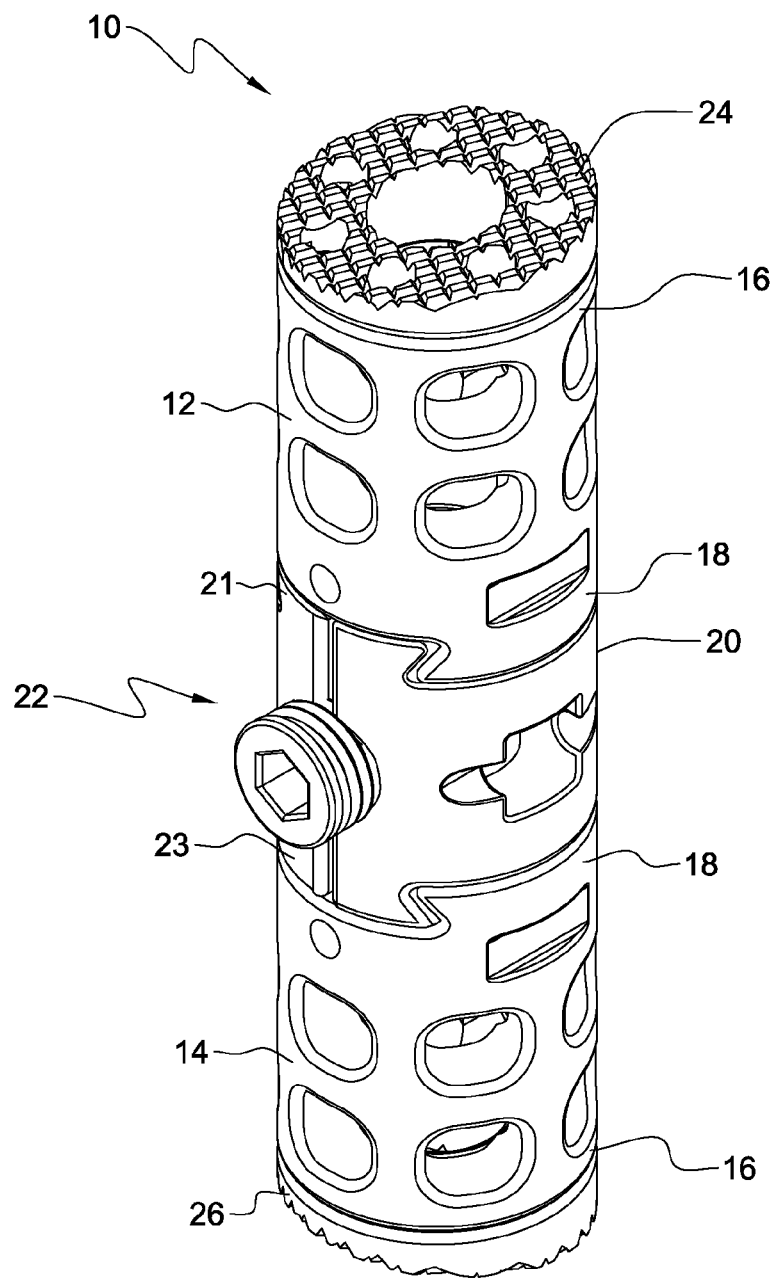
FIG. 1 is a front perspective view of a tissue spacer implant according to one aspect of the invention.
Figure 2:
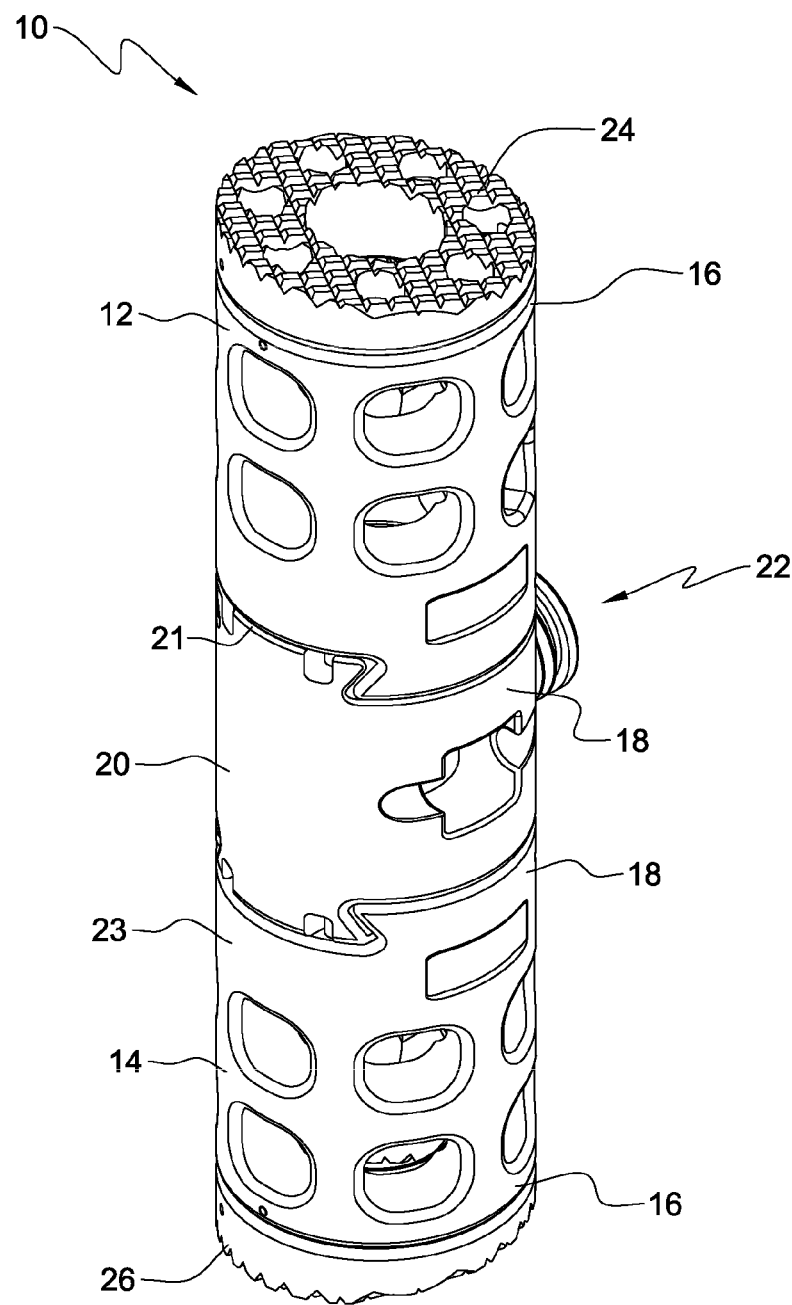
FIG. 2 is a rear perspective view of a tissue spacer implant shown in FIG. 1.

FIG. 1 is a front perspective view of a tissue spacer implant 10 according to one aspect of the invention. FIG. 2 is a rear perspective view of a tissue spacer 10 shown in FIG. 1. As shown, tissue spacer 10 includes a first end member 12 and a second end member 14. Each end member 12 and 14 include a first end 16 and a second end 18 opposite the first end 16 each configured to engage tissue, for example, bone, such as, vertebrae. According to aspects of the invention, implant 10 also includes an intermediate spacer member 20 positioned between first end member 12 and second end member 14. The intermediate spacer 20 includes a first end 21 and a second end 23 opposite the first end 21. Intermediate spacer member 20 typically includes a coupling mechanism 22 adapted to couple the second end 18 of the first end member 12 with the first end 21 of intermediate spacer member 20 and to couple the second end 18 of the second end member 14 with second end 23 of the intermediate member 20. End members 12 and 14 may be modular and allow the surgeon to mix and match various shaped and configured end members 12, 14 with an intermediate spacer member 20. As shown in FIGS. 1 and 2, first end 16 of end members 12 and 14 may be adapted to receive adapters 24 and 26, respectively, to adapt implant 10 to the tissue (not shown) into which implant 10 is to be inserted. For example, adapters 24 and 26 may be fashioned to mount to end members 12 and 14 and provide a surface that encourages retention to or compatibility with tissue. In one aspect, adapters 24 and 26 are referred to as "foot plates" in the art.

Figure 3:
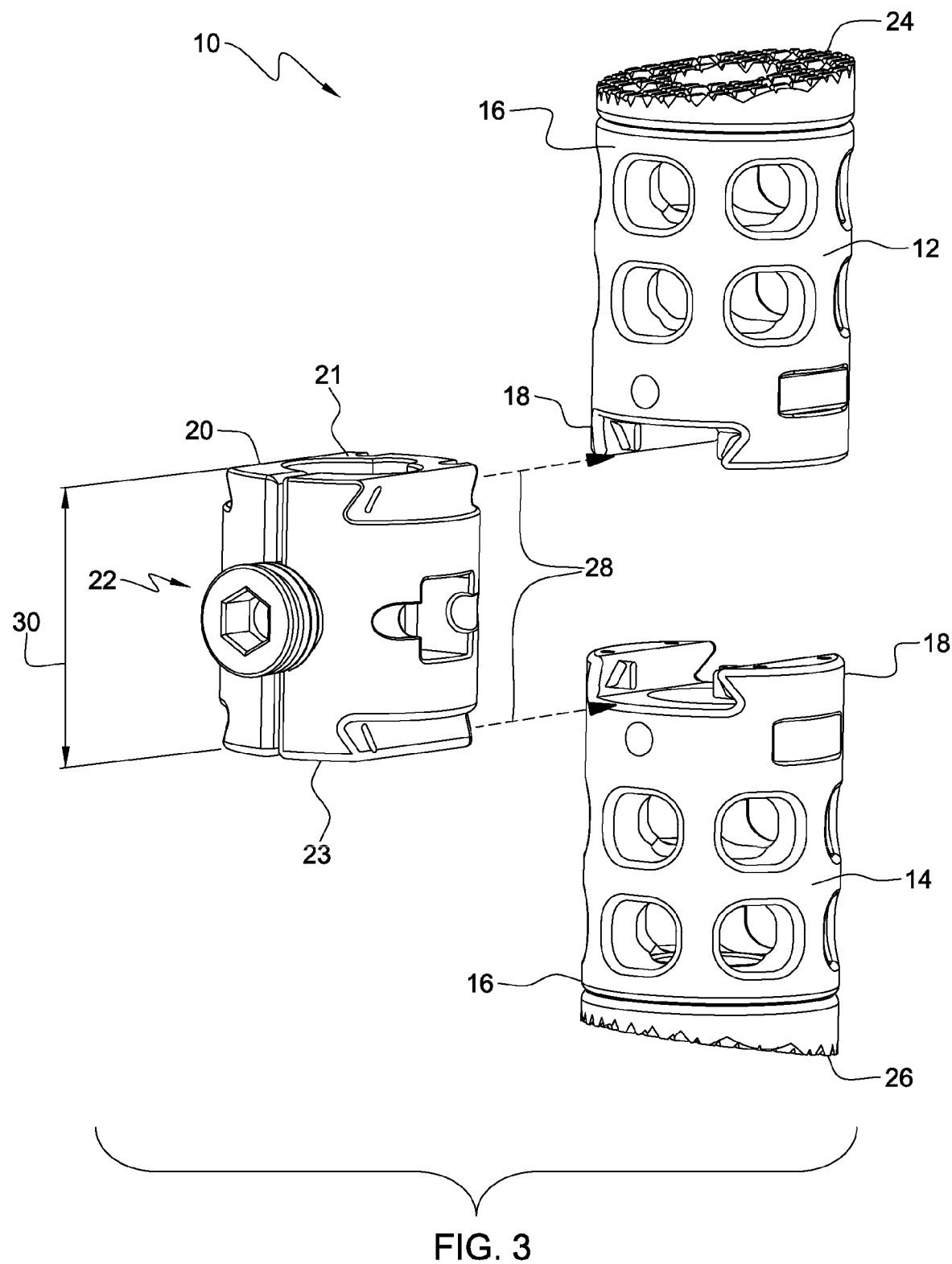
FIG. 3 is a front perspective view of a tissue spacer implant shown in FIG. 1 illustrating a typical insertion of the intermediate spacer between the end members according to one aspect of the invention.

FIG. 3 is a front perspective view of a tissue spacer implant 10 shown in FIGS. 1 and 2 and illustrating a typical insertion of a intermediate spacer member 20 between first end member 12 and second end member 14 according to one aspect of the invention, for example, as indicated by arrows 28. As will become clear in the following discussing of aspects of the invention, in one aspect, end members 12 and 14 may be positioned against tissue (not shown), for example, bone, whereby adapters 24 and 26 contact the tissue, and then intermediate spacer member 20 may be inserted between end members 12 and 14 as indicated by arrows 28. During or after insertion of intermediate spacer member 20 between end members 12 and 14, coupling mechanism 22 is activated to couple the three components: the first end member 12, the intermediate spacer member 20, and the second end member 14. According to aspects of the invention, the coupled members 12, 20, and 14 provide a substantially rigid implant between adjacent tissues, for example, vertebrae. In one aspect of the invention, intermediate spacer member 20 may be provided in a plurality of lengths or heights 30 whereby the intermediate spacer member 20 may be selected from one of these intermediate spacer members 20 depending upon the spacing between end members 12 and 14.

Figure 4:
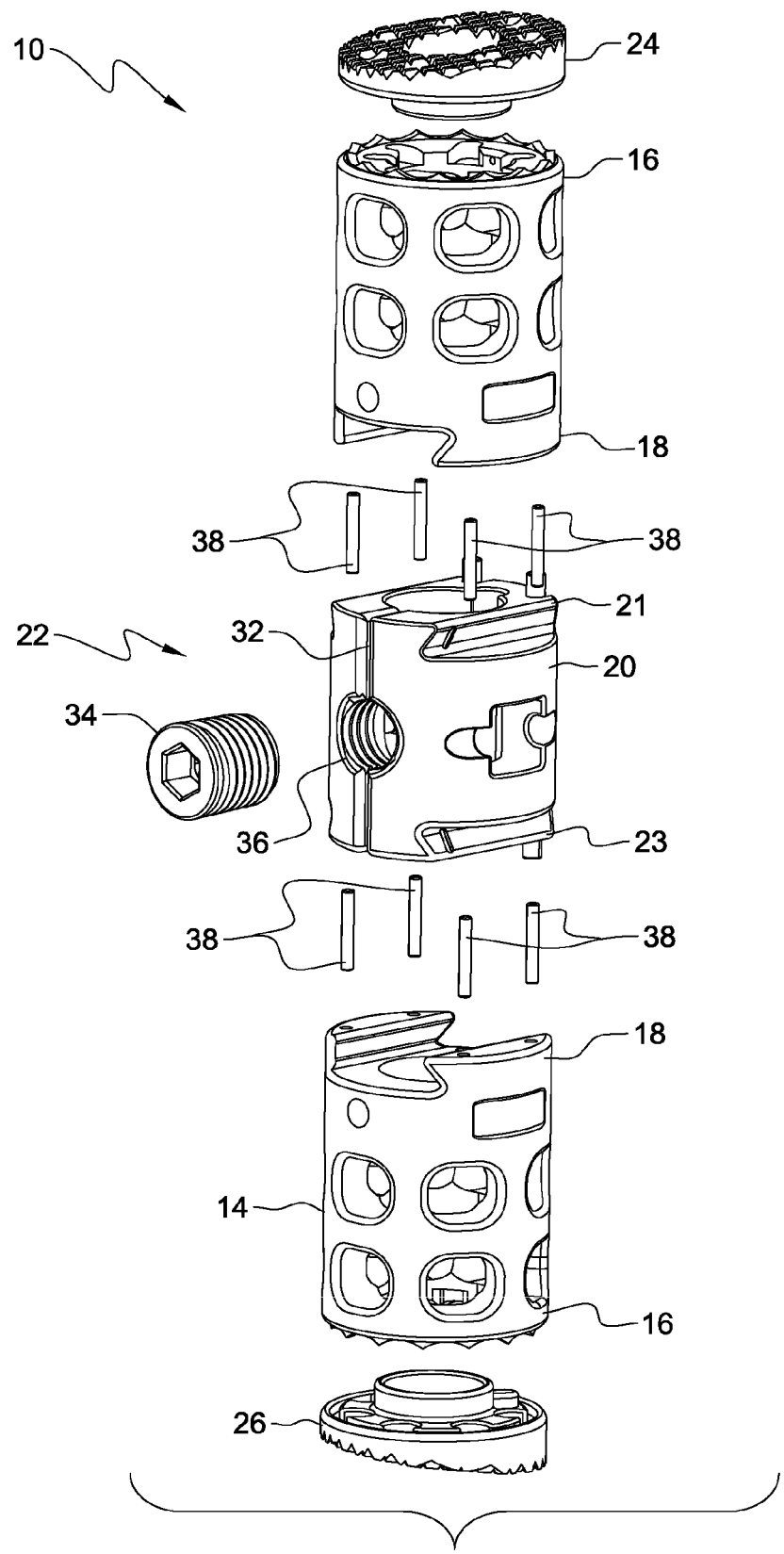
FIG. 4 is an exploded perspective view of a tissue spacer implant shown in FIG. 1.

FIG. 4 is an exploded perspective view of a tissue spacer implant 10 shown in FIGS. 1, 2, and 3. As shown in FIG. 4, coupling mechanism 22 may include an opening, gap, separation, slot, or slit 32 in intermediate spacer member 20 and a rod or pin 34, though other devices may be used, which is adapted to be inserted in a hole or opening 36 in intermediate spacer member 20. According to this aspect of the invention, as rod or pin 34 is inserted into hole 36, rod or pin 34 provides a camming effect to encourage the enlargement of opening 32 and the deflection of projections (see below) on ends 21 and 23 to promote engagement of end 21 with first end member 12 and the engagement of second end 23 with second end member 14. As shown in FIG. 4, in one aspect, rod 34 may be a threaded rod adapted to engage an internal thread 37 in hole 36 to effect the desired camming action.

As also shown in FIG. 4, implant 10 may include one or more reinforcing members 38, for example, elongated rods or bars, to reinforce at least one of end members 12 and 14, for example, to reinforce projections (see below) from end members 12 and 14. Reinforcing members 38 may be metallic, for example, made from steel, stainless steel, or titanium, among other metals, or non-metallic, for example, high molecular weight (UHMW) polyethylene, or its equivalent.

Figure 5:
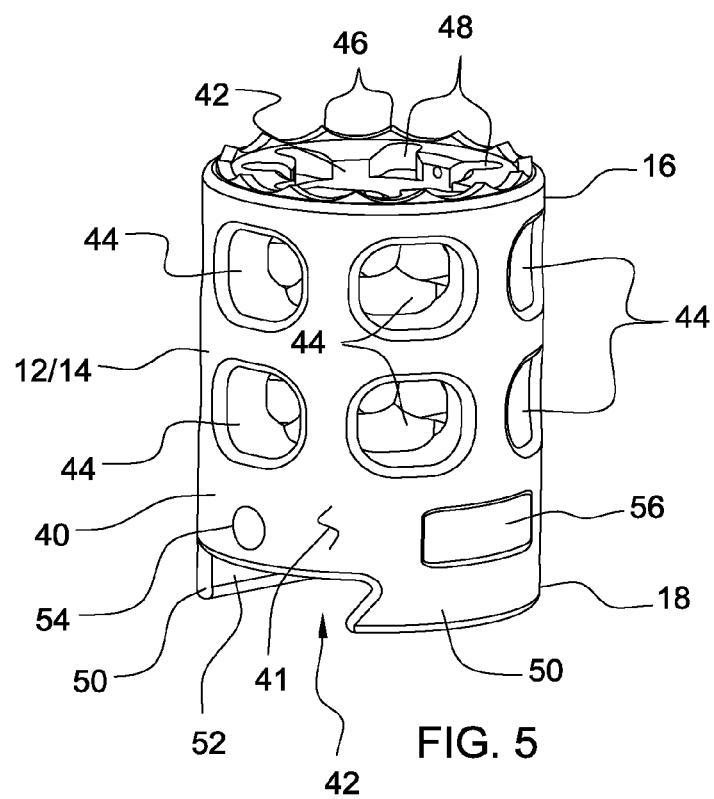
FIG. 5 is a top, front perspective view of an end member shown in FIGS. 1-4 according to an aspect of the invention.
Figure 6:
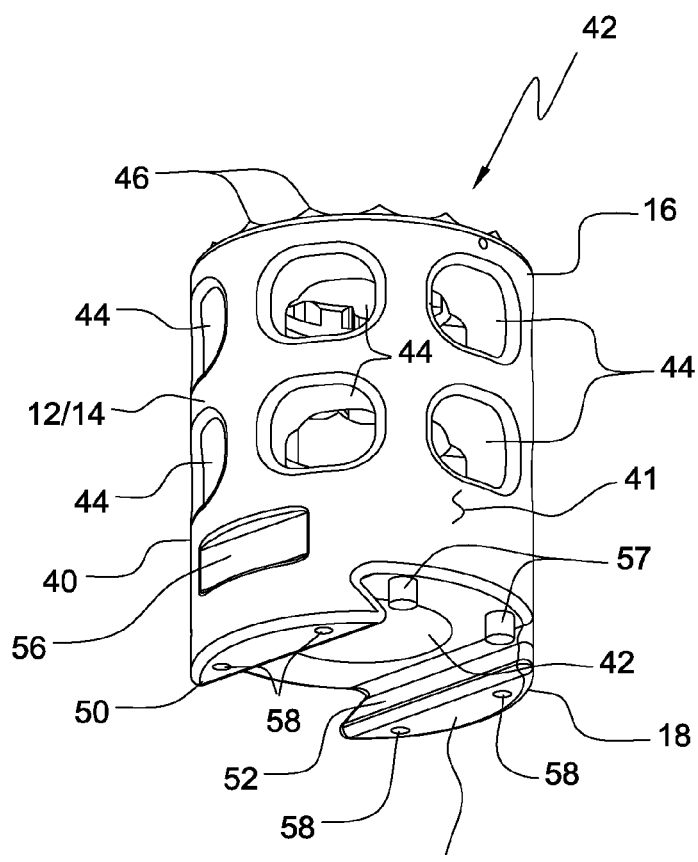
FIG. 6 is bottom, rear perspective view of the end member shown in FIG. 5.
Figure 7:
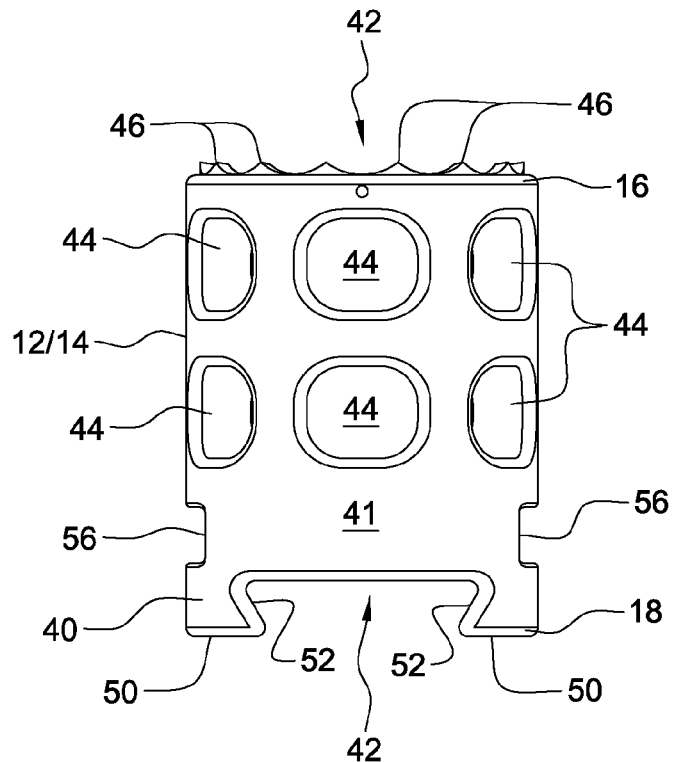
FIG. 7 is a front elevation view of the end member shown in FIG. 5, the rear elevation view being a mirror image thereof.
Figure 8:
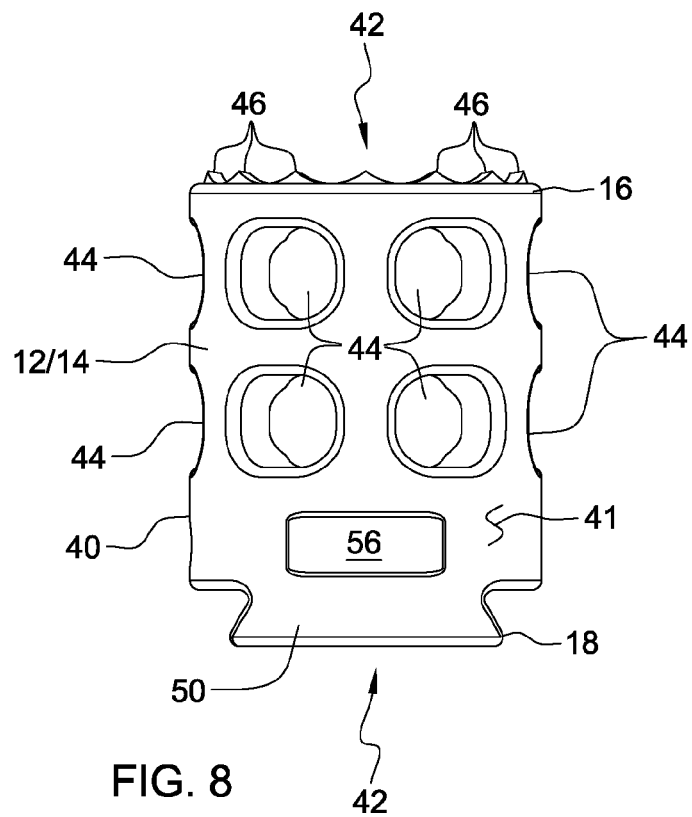
FIG. 8 is a right side elevation view of the end member shown in FIG. 5, the left side elevation view being a mirror image thereof.
Figure 9:
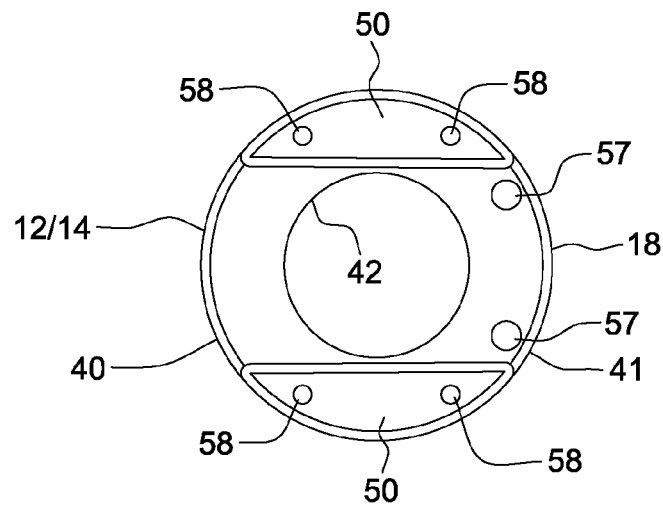
FIG. 9 is a bottom view of the end member shown in FIG. 5.

FIG. 5 is a top, front perspective view of an end member 12 or 14 shown in FIGS. 1-4 according to an aspect of the invention. In one aspect, end members 12 and 14 may be substantially identical, for example, to minimize manufacturing costs; however, in other aspects, end members 12 and 14 may not be substantially identical. FIG. 6 is a bottom, rear perspective view of end member 12, 14 shown in FIG. 5. FIG. 7 is a front elevation view of end member 12, 14 shown in FIG. 5, the rear elevation view of the end member 12, 14 being a mirror image thereof. FIG. 8 is a right side elevation view of the end member 12, 14 shown in FIG. 5, the left side elevation view of the end member 12, 14 being a mirror image thereof, and FIG. 9 is a bottom view of the member 12, 14 shown in FIG. 5.

As shown in FIGS. 5 through 9, end member 12, 14 comprises a generally cylindrical body 40 having and outer surface 41, a first end 16, and a second end 18. Though cylindrical body 40 is shown as a circular cylindrical body, a non-circular cylindrical body may also be used, for example, a polygonal cylindrical or an elliptical cylindrical body may also be provided according to aspects of the invention. It is also conceived that body 40 may be non-cylindrical, for example, having an arbitrary non-cylindrical shape.

As shown in FIGS. 5-9, the body 40 of end member 12, 14 may typically have a hole 42, for example, a central through hole extending from the first end 16 to the second end 18, though hole 42 may not pass completely through body 40, for example, hole 42 may be a blind hole having a bottom. As shown, body 40 may also include a plurality of holes or openings 44 extending from the outer surface 41 to hole 42. Holes or openings 44 may be rectangular with rounded corners, as shown, or may be oval in shape, although many other geometric shapes, for example, circular, elliptical, and polygonal (for example, triangular, square, or hexagonal), are contemplated. Hole 42 and holes 44 may be provided to reduce the weight of end member 12, 14 and/or to promote acceptance of end member 12, 14 by the tissue into which implant 10 is inserted. For example, in one aspect, holes 42 and 44 may be provided to allow introduction of bone graft material, for example, after implantation, to implant 10 to promote adherence to bone.

According to aspects of the invention, first end 16 of end member 12, 14 is adapted to engage tissue, for example, in one aspect, first end 16 may include projections 46 and/or recesses 48 adapted to engage tissue. However, as shown in FIGS. 1-4, first end 16 may be adapted to accept adapters 24 and 26, for example, "foot plates" 24 and 26. For example, first end 16 may include projections 46 and/or recesses 48 adapted to receive adapters 24 or 26.

According to aspects of the invention, second end 18 of end member 12, 14 is adapted to engage intermediate spacer member 20, as shown in FIGS. 1-4, for example, releasably engage intermediate spacer member 20. Though according to aspects of the invention any means may be provided to promote or provide engagement between second end 18 and the ends 21, 23 of intermediate spacer member 20, in one aspect of the invention, one means comprises projections 50, for example, a pair of opposing projections 50, extending from body 40, for example, axially extending from body 40. Projections 50 may be adapted to engage one or more cooperating recesses and/or projections in first end 21 and second end 23 of intermediate spacer member 20. According to aspects of the invention, different kinds of recesses or projections may be used to engage, join, or couple first end 21 and second end 23 with intermediate spacer member 20, including, but not limited to, rails, slots, and channels. As shown in FIGS. 5-9, in one aspect, projections 50 may provide beveled projections, for example, having a bevel 52. Projections 50 having bevel surfaces 52 may comprise one component of a dove-tail like engagement mechanism, wherein the surfaces 52 engage cooperating surfaces on first end 21 and second end 23 of intermediate spacer member 20. As shown in FIGS. 5-9, in one aspect, projections 50 of end member 12, 14 may comprise "female" dovetails. In another aspect, projections 50 of end member 12, 14, may also comprise "male" dovetails.

As also shown in FIGS. 5-9, end member 12, 14 may also include features that accommodate an insertion or manipulation tool (not shown). For example, end member 12, 14 may include one or more holes, recesses, or apertures 54 and/or one or more slots, slits, or recesses 56 positioned and adapted to engage a tool, for example, a handling or insertion tool. Engagement and handling of end member 12, 14 with a tool according to an aspect of the invention will be discussed below.

End member 12, 14 may also include recesses or projections adapted to limit or enhance engagement of intermediate spacer member 20 with end members 12 and 14. For example, as shown in FIGS. 5-9, end member 12, 14 may include one or more recesses or projections 57 shaped, for example, as pins, and positioned to engage one or more projections or recesses in intermediate spacer member 20 which limit or act as a "stop" to the engagement with end members 12 and 14, for example, as intermediate spacer member 20 is slidably engaged with end members 12 and 14 as shown in FIG. 3. For example, as shown in FIGS. 10-14, intermediate spacer member 20 may include recesses 77 positioned and shaped to engage projections 57 to limit the movement of intermediate member 20 when engaging end members 12 and 14.

As discussed above with respect to FIG. 4, end member 12, 14 may also include reinforcing elements 38, for example, elongated rods or bars, to reinforce at least one of end members 12 and 14, for example, to reinforce projections 50 of end members 12 and 14. Accordingly, in one aspect, end members 12 and 14 may include holes or apertures 58 adapted to receive one or more reinforcing elements 38. As shown in FIGS. 5-9, holes 58 may be directed axially into end members 12 and 14, for example, through projections 50 to reinforce projections 50 and minimize or prevent excess deflection.

End member 12, 14 may be fabricated from metals and/or non-metals. For example, in one aspect end member 12, 14 may be metallic, for example, made from any metal that is resistant to corrosion when exposed to bodily fluids, such as, stainless steel or titanium. In another aspect, end member 12, 14, may be non-metallic, for example, made from a plastic that is resistant to attack when exposed to bodily fluids, such as, a polyether ether ketone (PEEK), a polytetraflouroethylene (PTFE), or their equivalents. In one aspect, end members 12 and 14 may typically be made from FDA approved implant grade materials, such as, implant grade titanium and/or implant stainless steel or implant grade plastics, such as, PEEK. The size of end member 12, 14 may vary broadly depending upon the size of the cavity or tissue into which implant 10 is to be inserted. For example, end member 12, 14 may have a height or length ranging from about 0.25 to about 6 inches, but is typically between about 0.50 to about 1.5 inches in height or length. Also, the diameter or outside dimension of end member 12, 14 may range from about 0.125 to about 3 inches, but is typically between about 0.50 to about 1.5 inches in outside dimension.

Figure 10:
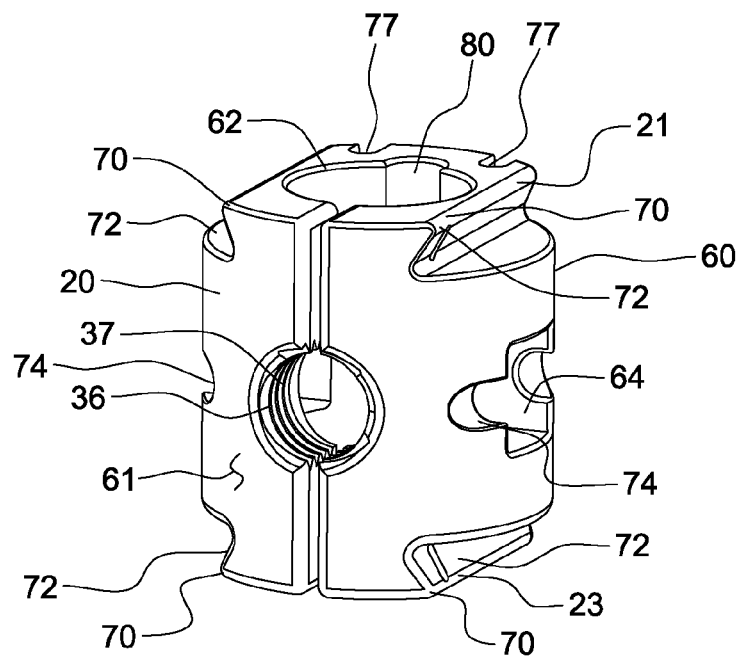
FIG. 10 is a front perspective view of an intermediate spacer member shown in FIGS. 1-4 according to an aspect of the invention.
Figure 11:
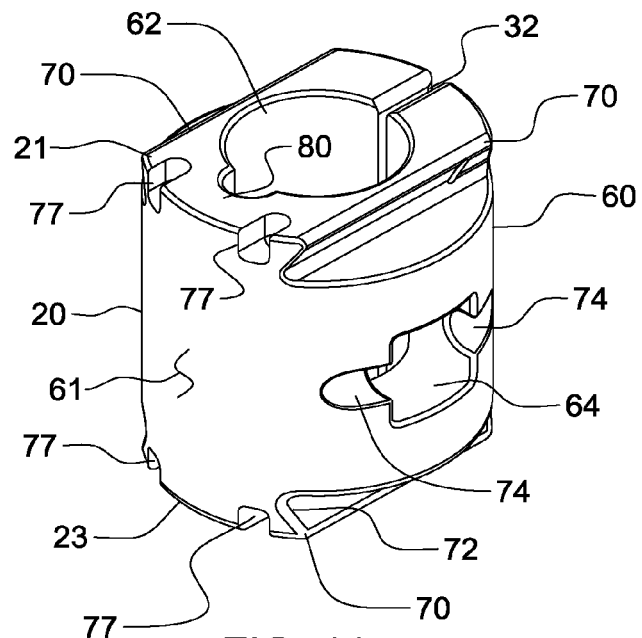
FIG. 11 is a rear perspective view of the intermediate spacer member shown in FIG. 10.
Figure 12:
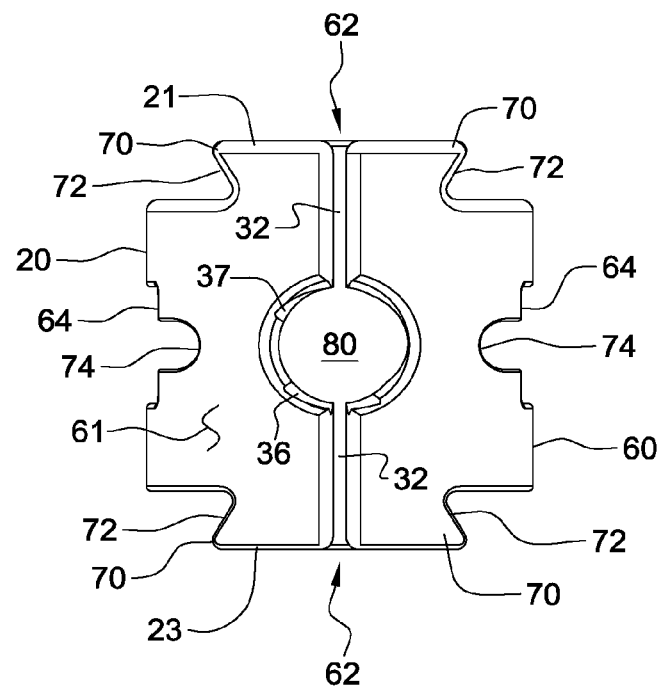
FIG. 12 is a front elevation view of the intermediate spacer member shown in FIG. 10.
Figure 13:
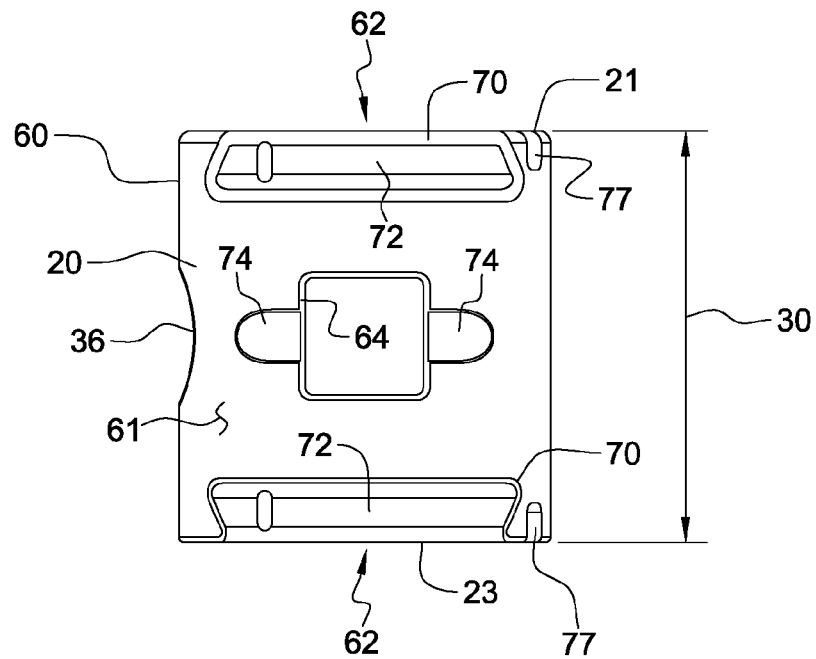
FIG. 13 is a right side elevation view of the intermediate spacer member shown in FIG. 10, the left side elevation view being a mirror imager thereof.
Figure 14:
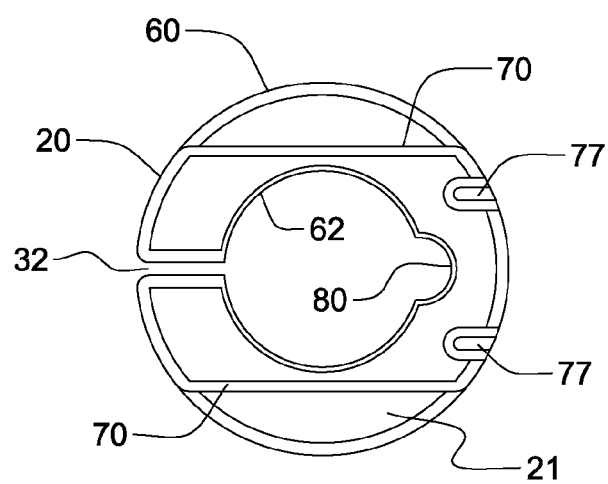
FIG. 14 is a top view of the intermediate spacer member shown in FIG. 10, the bottom view being a mirror imager thereof.

FIG. 10 is a front perspective view of the intermediate spacer member 20 shown in FIGS. 1-4 according to an aspect of the invention. FIG. 11 is a rear perspective view of intermediate spacer member 20 shown in FIG. 10. FIG. 12 is a front elevation view of the intermediate spacer member 20 shown in FIG. 10. FIG. 13 is a right side elevation view of the intermediate spacer member 20 shown in FIG. 10, the left side elevation view of intermediate spacer member 20 being a mirror image thereof. FIG. 14 is a top view of the intermediate spacer member 20 shown in FIG. 10, the bottom view being a mirror image thereof.

As shown in FIGS. 10 through 14, intermediate spacer member 20 comprises a generally cylindrical main body 60 having and outer surface 61, a first end 21, and a second end 23 opposite first end 21. Though cylindrical body 60 is shown as a circular cylindrical body, a non-circular cylindrical body may also be used, for example, a polygonal cylindrical or an elliptical cylindrical body may also be provided according to aspects of the invention. It is also conceived that body 60 may be non-cylindrical, for example, having an arbitrary non-cylindrical shape.

As shown in FIGS. 10-14, the body 60 of intermediate spacer member 20 may typically have a hole 62, for example, a central through hole extending from the first end 21 to the second end 23, though hole 62 may not pass completely through body 60, for example, hole 62 may be a blind hole having a bottom. As shown, body 60 also includes a plurality of holes 64 extending from the outer surface 61 to hole 62. Hole 62 and holes 64 may be provided to reduce the weight of intermediate spacer member 20 and/or to promote acceptance by the tissue into which implant 10 is inserted. For example, in one aspect, holes 62 and 64 may be provided to allow introduction of bone graft material, for example, after implantation, to implant 10 to promote adherence to bone.

According to aspects of the invention, end 21 and end 23 of intermediate spacer member 20 are adapted to engage end members 12 and 14, respectively, specifically, engage second end 18 of end members 12 and 14, for example, releasably engage second end 18 of end members 12 and 14. Though according to aspects of the invention any means may be provided to promote or provide engagement between ends 21 and 23 and second end 18 and of end members 12 and 14, in one aspect of the invention, one means comprises projections 70, for example, a pair of opposing projections 70, extending from body 60, for example, axially extending from body 60. Projections 70 may be adapted to engage one or more cooperating recesses and/or projections in one of end 16 and/or end 18 of end members 12 and 14. In one aspect of the invention, projections 70 straddle the separation or slot 32. In this aspect of the invention, the term "straddle" means that at least one projection 70 is positioned at least partially to one side of separation or slot 32 and another projection 70 is at least partially to the other side of separation or slot 32. In one aspect, when projections 70 "straddle" separation or slot 32, one projection 70 and another projection 70 may be equidistant from separation or slot 32, for example, equidistant from the centerline of separation or slot 32. However, in another aspect, two or more projections 70 may straddle separation or slot 32 and may not be equidistant from separation or slot 32. Though projections 70 shown in FIGS. 10-14 suggest that projections 70 may reside on a single structure, according to aspects of the invention, projections 70 may extend individually from the ends 21, 23 of body 20.

As shown in FIGS. 10-14, in one aspect, projections 70 may provide beveled projections, for example, having a beveled surface 72. Projections 70 having bevel surfaces 72 may comprise one component of a dove-tail like engagement mechanism, wherein the surfaces 72 engage cooperating surfaces on end 16 and/or end 18 of end members 12 and 14. As shown in FIGS. 10-14, in one aspect, projections 70 of intermediate spacer member 20 may comprise "male" dovetails. In another aspect, projections 70 of intermediate spacer member 20 may also comprise "female" dovetails.

As also shown in FIGS. 10-14, intermediate spacer member 20 may also include features that accommodate an insertion or a manipulation tool (not shown). For example, intermediate spacer member 20 may include one or more holes, recesses, slots, slits, or apertures 74 positioned and adapted to engage a tool, for example, a handling or insertion tool. Engagement and handling of intermediate spacer member 20 with a tool according to an aspect of the invention will be discussed below.

Intermediate spacer member 20 may also include recesses or projections adapted to limit or enhance engage of intermediate spacer member 20 with end members 12 and 14. For example, as shown in FIGS. 10-14, intermediate spacer member 20 may include one or more projections or recesses 77 shaped and positioned to engage one or more recesses or projections in end members 12 and 14 which limit or act as a "stop" to the engagement with end members 12 and 14, for example, as intermediate spacer member 20 is slidably engaged with end members 12 and 14 as shown in FIG. 3. For example, as shown in FIGS. 5-9, end members 12 and 14 may include projections 57 positioned and shaped to engage recesses 77 to limit the movement of intermediate member 20 when engaging end members 12 and 14.

As discussed above, with respect to FIG. 4, according to one aspect of the invention, implant 10 includes a coupling mechanism 22 adapted to couple the three components: the first end member 12, the intermediate spacer member 20, and the second end member 14. In one aspect, the coupling mechanism 22 includes a rod or pin 34 that is inserted into hole 36 and provides a camming effect to encourage the deflection of projections 70 on ends 21 and 23 of intermediate spacer member 20 to promote engagement with end members 12 and 14. In one aspect, in order to enhance the flexibly of intermediate spacer member 20 and to promote the engagement of projections 70 with projections 50 of end members 12 and 14, the deflection of projections 70 under the camming effect of rod or pin 34 is enhanced by providing at least one recess 80 in the inner surface of hole 62. Among other things, the at least one recess 80 reduces the bending resistance of intermediate spacer member 20 and thus enhances the flexibly of intermediate spacer member 20. For example, in one aspect, an elongated recess 80 may be provided substantially opposite the location of slot 32 of intermediate spacer member 20 so that when pin or rod 34 is introduced to hole 36, the enhanced flexibility of intermediate spacer member 40 enhances the deflection of projections 70 thus ensuring a more secure engagement with projections 50 of end members 12 and 14. Though recess 80 may take many geometrical shapes or forms, in one aspect, as shown in FIGS. 10-14, recess 80 may comprise a recess having a semicircular or arcuate cross section, for example, to minimize stress concentration under the camming load of pin or rod 34.

Intermediate spacer member 20 may be fabricated from metals and/or non-metals. For example, in one aspect, intermediate spacer member 20 may be metallic, for example, made from any metal that is resistant to corrosion when exposed to bodily fluids, such as, stainless steel or titanium. In another aspect, intermediate spacer member 20 may be nonmetallic, for example, made from a plastic that is resistant to attack when exposed to bodily fluids, such as, a PEEK, a PTFE, or their equivalents. In one aspect, spacer member 20 may typically be made from FDA approved implant grade materials, such as, implant grade titanium and/or implant stainless steel or implant grade plastics, such as, PEEK. The size of intermediate spacer member 20 may vary broadly depending upon the size of the cavity or tissue into which implant 10 is to be inserted. For example, intermediate spacer member 20 may have a height or length ranging from about 0.25 to about 6 inches, but is typically between about 0.50 to about 1.5 inches in height or length. Also, the diameter or outside dimension of intermediate spacer member 20 may range from about 0.125 to about 3 inches, but is typically between about 0.50 to about 1.5 inches in outside dimension.

According to one aspect of the invention, a plurality of intermediate spacer members 20 may be provided wherein each of the spacer members 20 may be adapted to couple to end members 12 and 14, for example, while each of the plurality of spacer members 20 are of varying height or length. In one aspect, the plurality of spacer members 20 are provided with regularly varying heights, for example, varying in height by 1 millimeter [mm] or 5 mm intervals. This allows the surgeon to determine a desired height of spacer member 20 during surgery, as discussed below, and the desired spacer member 20 of the desired height may be selected from the plurality of spacer members 20 provided. In one aspect, a kit may be provided having implant 10 having elements, for example, intermediate spacer members 20 and/or end members 12, 14 of varying length, diameter, and/or shape, for example, one or more, geometric cross-sectional shapes.

According to one aspect of the invention, a tissue spacer implant 10 is provided having the intermediate spacer member 20 comprising the main body 60, and the coupling mechanism 22 comprises a first pair of projections 70 from the main body 60 adapted to engage the second end 18 of the first end member 12, a second pair of projections 70 from the main body 60 adapted to engage the second end 18 of the second end member 14, a means for deflecting at least one of the projections 70 of the first pair of projections and at least one of the projections 70 of the second pair of projections wherein the first pair of projections engages the second end 18 of the first end member 12 and the second pair of projections 70 engages the second end 18 of the second end member 14 to couple the first end member 12 to the second end member 14.

According to another aspect of the invention, a tissue spacer implant 10 is provided having an intermediate spacer member 20 comprising the hollow main body 60 having longitudinal separation 32, and wherein the means for deflecting at least one of the projections 70 of the first pair of projections and at least one of the projections 70 of the second pair of projections comprises a separation widening device, for example, a pin or rod 34, adapted to be inserted into the longitudinal separation 32 and widen the separation 32 wherein at least one of the projections 70 of the first pair of projections and at least one of the projections of the second pair of projections are deflected.

Figure 15:
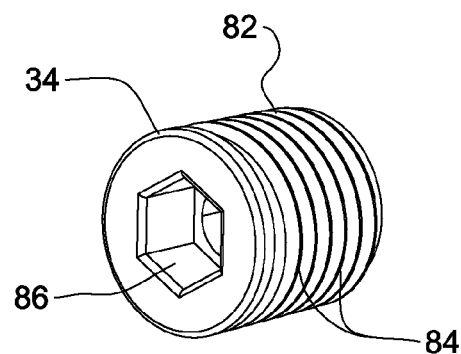
FIG. 15 is a perspective view of a threaded rod shown in FIGS. 1-4 according to one aspect of the invention.
Figure 16:
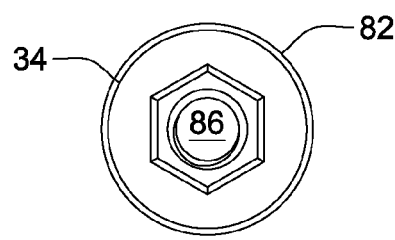
FIG. 16 is an end view of the threaded rod shown in FIG. 15.
Figure 17:
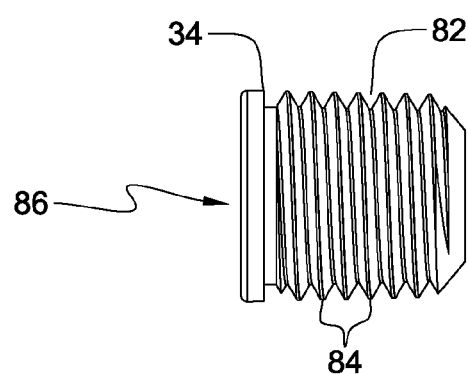
FIG. 17 is a side elevation view of the threaded rod shown in FIG. 15.

FIG. 15 is a perspective view of a camming device 34 shown in FIGS. 1-4 according to one aspect of the invention. FIG. 16 is an end view of the camming device 34 shown in FIG. 15 and FIG. 17 is a side elevation view of the camming device 34 shown in FIG. 15. According to aspects of the invention, camming device 34 may be a threaded rod or set screw and may comprise one means of deflecting projections 70 on intermediate spacer member 20 to promote engagement of projections 70 with projections 50 of end members 12 and 14. Again, this deflection of projections 70 may be effected by any camming device 34, for example, any wedge or cam adapted to separate the slot or separation 32 of intermediate spacer member 20.

As shown in FIGS. 15-17, in one aspect, camming device, threaded rod, or set screw 34 comprises a cylindrical rod 82 having a plurality of external threads 84 adapted to engage internal threads 37 in hole 36 (see FIG. 4). Threads 37 and 84 may comprise any conventional thread pattern, for example, an NPT, a UN, a UNC, or a UNJ thread, and the like. Threaded rod 34 may also include one end adapted to receive and be driven by a tool. For example, as shown in FIGS. 15-17, camming device 34 may include a hole 86 adapted to receive a hex-head wrench (that is, an Allen wrench) though a hole 86 adapted for a slotted head, a Phillips head, or a Torx head, among others, may be provided.

Camming device or threaded rod 34 may be fabricated from metals or non-metals. For example, in one aspect, camming device 34 may be metallic, for example, made from any metal that is resistant to corrosion when exposed to bodily fluids, such as, stainless steel or titanium. In another aspect, camming device 34 may be non-metallic, for example, made from a plastic that is resistant to attack when exposed to bodily fluids, such as, a PEEK, a PTFE, or their equivalents. In one aspect, camming device 20 may typically be made from FDA approved implant grade materials, such as, implant grade titanium and/or implant stainless steel, or implant grade plastics, such as, PEEK. The size of camming device 34 may vary broadly depending upon the size of implant 10. For example, camming device 34 may have a length ranging from about 0.125 to about 2 inches, but is typically between about 0.25 to about 0.75 inches in length. Also, the diameter or outside dimension of camming device 34 may range from about 0.125 to about 1 inch, but is typically between about 0.25 inches to about 0.50 inches in outside dimension.

Figure 18:
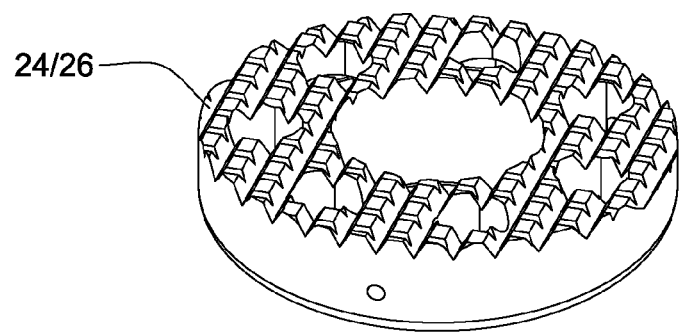
FIG. 18 is top perspective view of an adapter according to one aspect of the invention.
Figure 19:
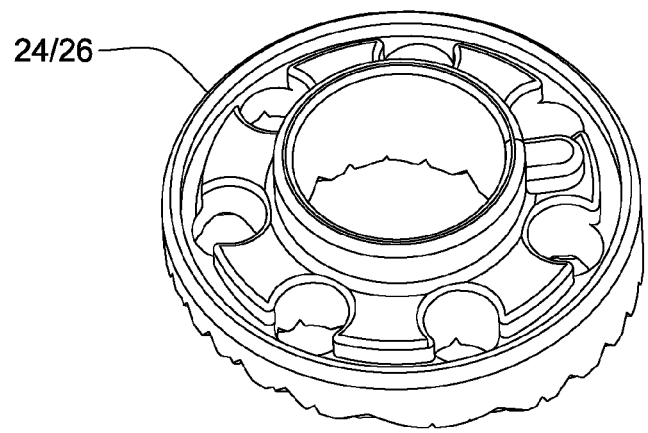
FIG. 19 is bottom perspective view of the adapter shown in FIG. 18.

FIG. 18 is top perspective view of a tissue adapter 24, 26 according to one aspect of the invention. FIG. 19 is bottom perspective view of the tissue adapter 24, 26 shown in FIG. 18. In one aspect of the invention, tissue adapters, or simply, adapters, 24 and 26 may be substantially identical, for example, to minimize manufacturing costs; however, in other aspects, tissue adapter 24, 26 may not be substantially identical. In one aspect of the invention, adapters 24 and 26 are referred to as "foot plates."

According to one aspect of the invention, some form of end surface or foot plate 24, 26 may be provided to implant 10 to enhance engagement with tissue, for example, bone. In one aspect, adapters 24 and 26 may be used to provide varying types of tissue contacting surfaces and structures, including, but not limited to, sharp tines, porous coatings, biomaterial/ingrowth surfaces and ridge structures. In one aspect, a modular footplate 24, 26 may be coupled to implant 10 to accommodate various clinical deformities or bone growth coatings. As shown in FIGS. 1-3, adapters 24 and 26 may provide angled end surfaces. In one aspect, adapters 24 and 26 may be attachable to end members 12 and 14 and address various clinical deformities that are encountered. Adapters 24 and 26 may be mounted to end members 12 and 14 by conventional means, for example, press fit, snap locks, screws, and pins, among other conventional means.

Figure 20:
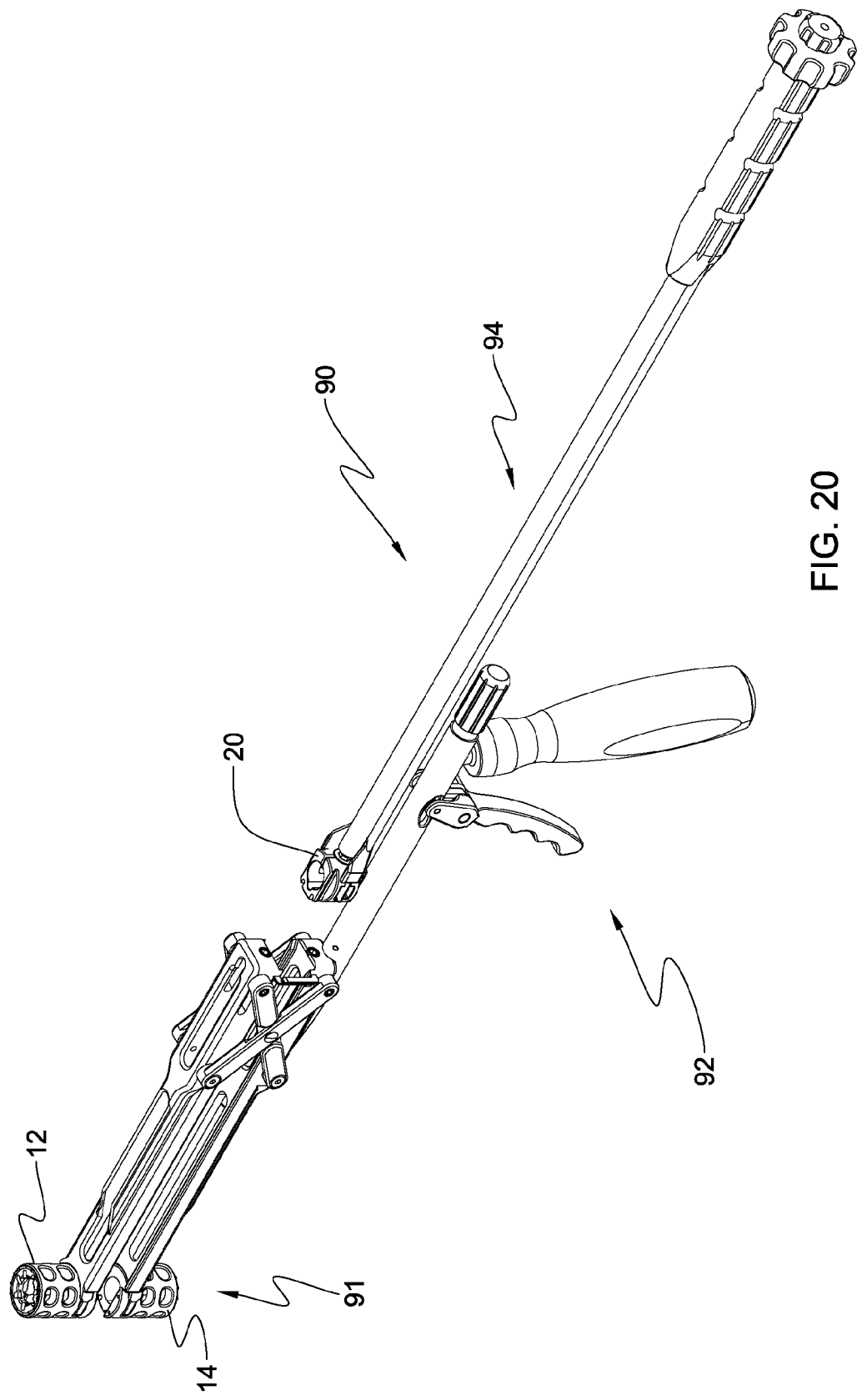
FIG. 20 is a perspective view of a typical insertion tool that can be used to implant the tissue spacer according to an aspect of the present invention.
Figure 21:
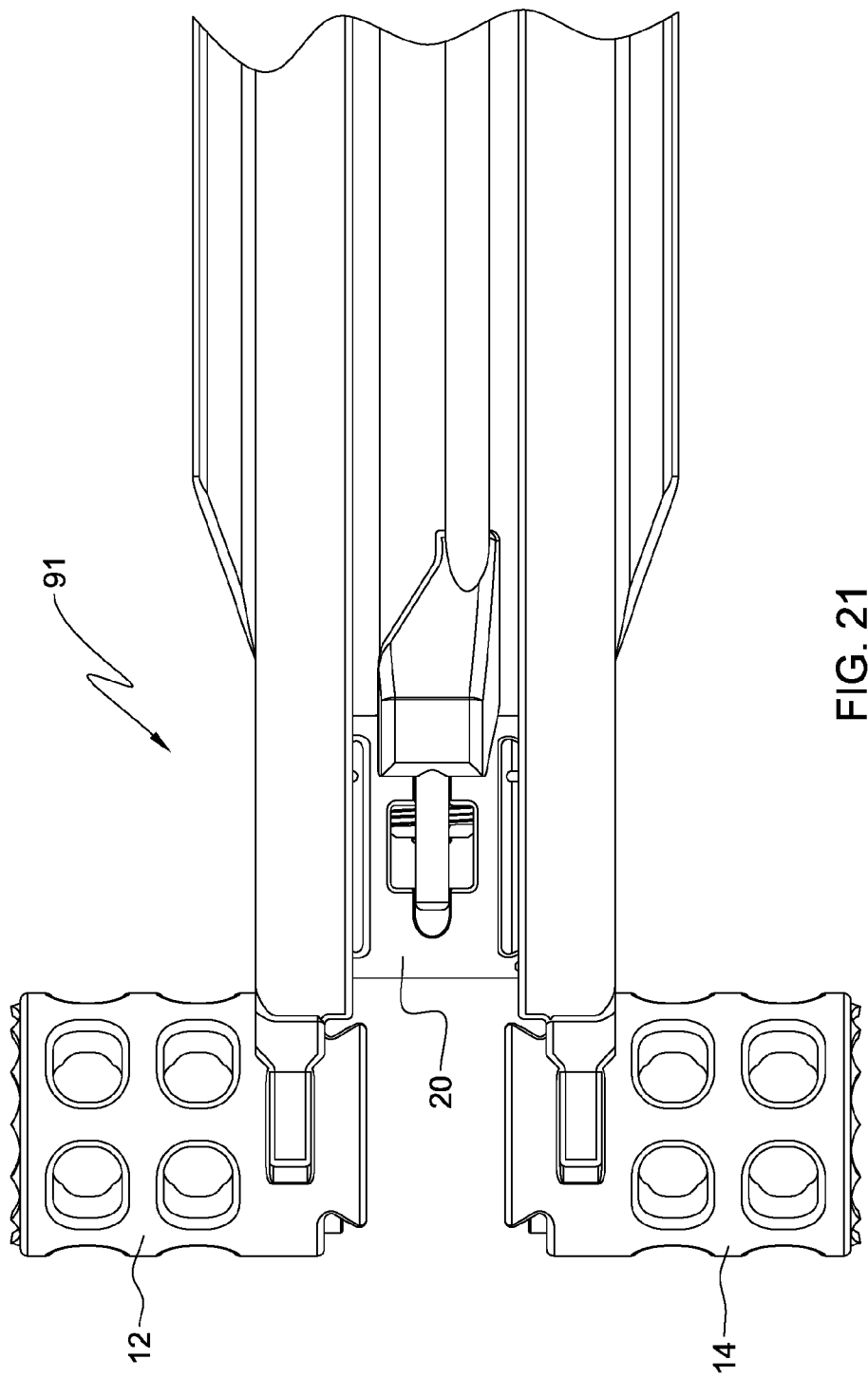
FIG. 21 is a detailed side elevation view of the tool shown in FIG. 20 illustrating one means of implanting the tissue space shown in FIGS. 1 through 4.

FIG. 20 is a perspective view of a typical insertion tool 90 that can be used to implant the tissue spacer 10 according to an aspect of the present invention. FIG. 21 is a detailed side elevation view of the tool 90 shown in FIG. 20 illustrating one means of implanting the tissue space 10 shown in FIGS. 1 through 4. A detailed description of insertion tool 90 is provided below with respect to FIGS. 46-61.

As shown in FIG. 20, according to aspects of the invention, tissue spacer 10 may be inserted between tissue, for example, between two vertebrae, by first mounting end members 12 and 14 to the working or proximal end 91 of tool 90. As will be discussed further below, the separation of end members 12 and 14 can be varied by manipulating hand lever assembly 92 of tool 90. According to aspects of the invention, once the separation of end members 12 and 14 is determined (for example, as a function of the spacing between vertebrae), an appropriately sized intermediate spacer member 20 can be selected by the surgeon from a plurality of spacer members 20 of varying dimension and inserted between end members 12 and 14 with the aid of insertion tool 94, for example, as illustrated in FIG. 3 above. Once properly placed between end members 12 and 14, coupling mechanism 22 of intermediate spacer member 20, for example, having set screw 34, is activated by rotating set screw 34 using a tool head incorporated into insertion tool 94 to secure intermediate spacer member 20 to end members 12 and 14 as described above. Again, detailed aspects of tools 90 and 92 and their operation with respect to implant 10 will be provided with respect to FIGS. 46-61 below.

Figure 22:
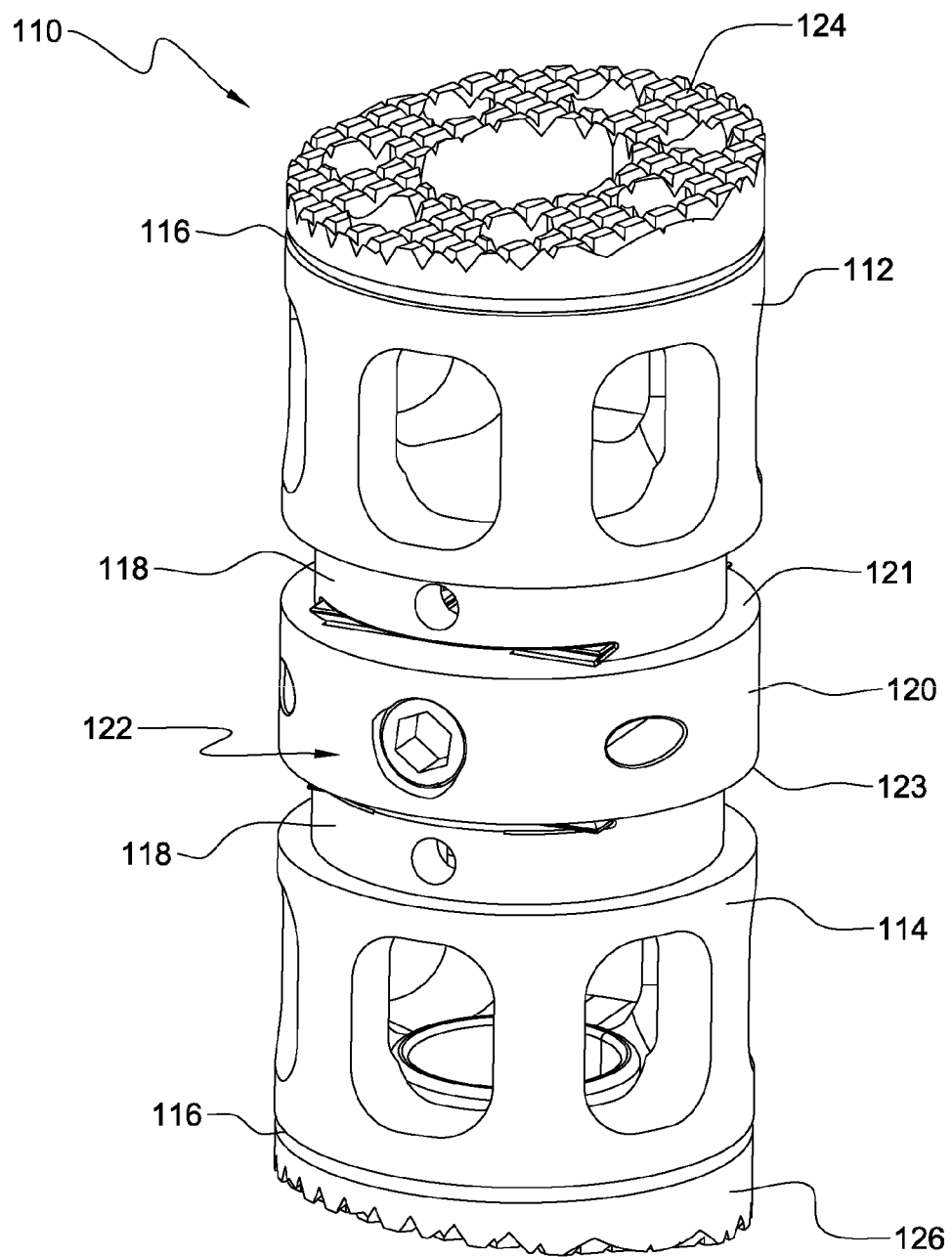
FIG. 22 is a front elevation view of another embodiment of a tissue spacer device according to another aspect of the present invention.
Figure 23:
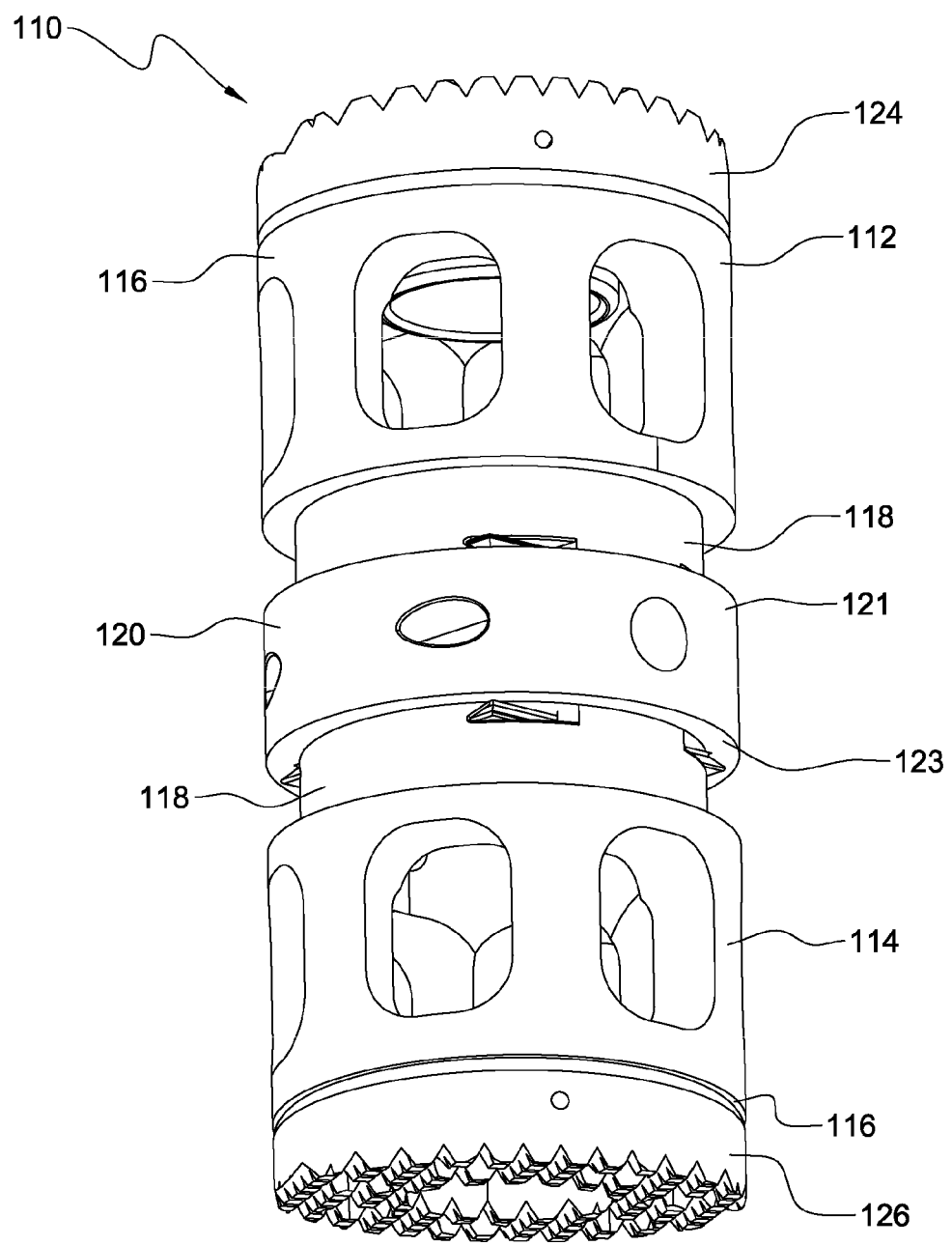
FIG. 23 is a rear perspective view of the tissue spacer shown in FIG. 22.

FIG. 22 is a front elevation view of another embodiment of a tissue spacer implant 110 according to another aspect of the present invention. FIG. 23 is a rear perspective view of the tissue spacer implant 110 shown in FIG. 22.

As shown, tissue spacer implant 110 includes a first end member 112 and a second end member 114. Each end member 112 and 114 includes a first end 116 and a second end 118 opposite the first end 116. First end 116 is configured to engage tissue, for example, bone, such as, vertebrae. According to aspects of the invention, implant 110 also includes an intermediate spacer member 120 positioned between first end member 112 and second end member 114. The intermediate spacer 120 includes a first end 121 and a second end 123 opposite the first end 121. Intermediate spacer member 120 typically includes a coupling mechanism 122 adapted to couple the second end 118 of the first end member 112 with the first end 121 of intermediate spacer member 120 and to couple the second end 118 of the second end member 114 with second end 123 of the intermediate member 120. End members 112 and 114 may be modular and allow the surgeon to mix and match various shaped and configured end members 112, 114 with an intermediate spacer member 120. As shown in FIGS. 22 and 23 first end 116 of end members 112 and 114 may be adapted to receive adapters 124 and 126, respectively, to adapt implant 110 to the tissue (not shown) into which implant 110 is to be inserted. For example, adapters 124 and 126 may be fashioned to mount to end members 112 and 114 and provide a surface that encourages retention to or compatibility with tissue. In one aspect, adapters 124 and 126 are referred to as "foot plates" in the art, an example of which is illustrated in FIGS. 18 and 19 above.

Figure 24:
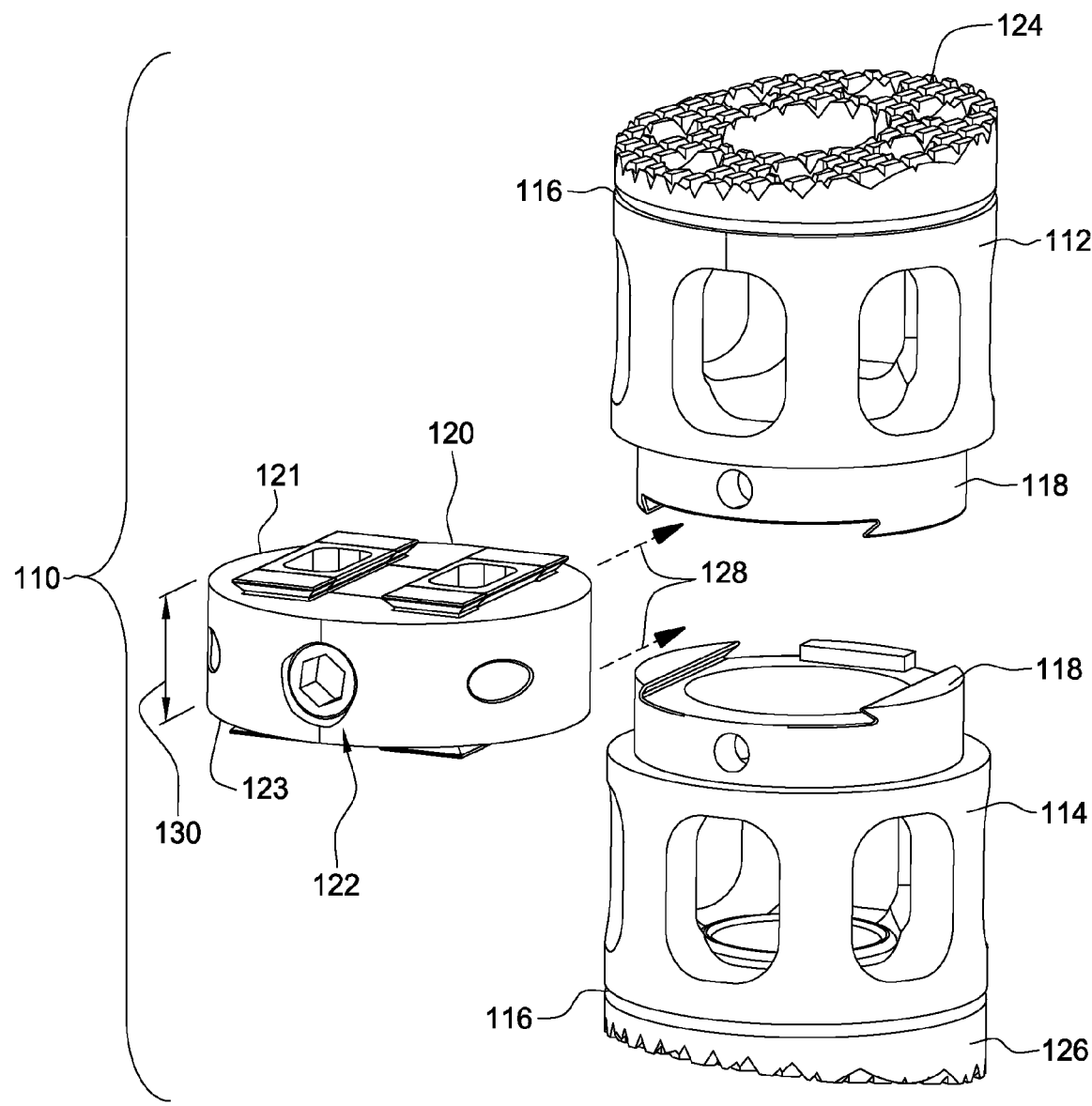
FIG. 24 is a front perspective view of a tissue spacer shown in FIG. 22 illustrating a typical insertion of the intermediate spacer between end members according to one aspect of the invention.

FIG. 24 is a front perspective view of a tissue spacer implant 110 shown in FIGS. 22 and 23 and illustrating a typical insertion of a intermediate spacer member 120 between first end member 112 and second end member 114 according to one aspect of the invention, for example, as indicated by arrows 128. As will become clear in the following discussion of aspects of the invention, in one aspect, end members 112 and 114 may be positioned against tissue (not shown), for example, bone, whereby adapters 124 and 126 contact the tissue, and then intermediate spacer member 120 may be inserted between end members 112 and 114 as indicated by arrows 128. During or after insertion of intermediate spacer member 120 between end members 112 and 114, coupling mechanism 122 is activated to couple the three components: the first end member 112, the intermediate spacer member 120, and the second end member 114. According to aspects of the invention, the coupled members 112, 120, and 114 provide a substantially rigid implant between adjacent tissue, for example, vertebrae. In one aspect of the invention, intermediate spacer member 120 may be provided in a plurality of lengths or heights 130 whereby the intermediate spacer member 120 may be selected from one of these intermediate spacer members 120 depending upon the spacing between end members 112 and 114.

Figure 25:
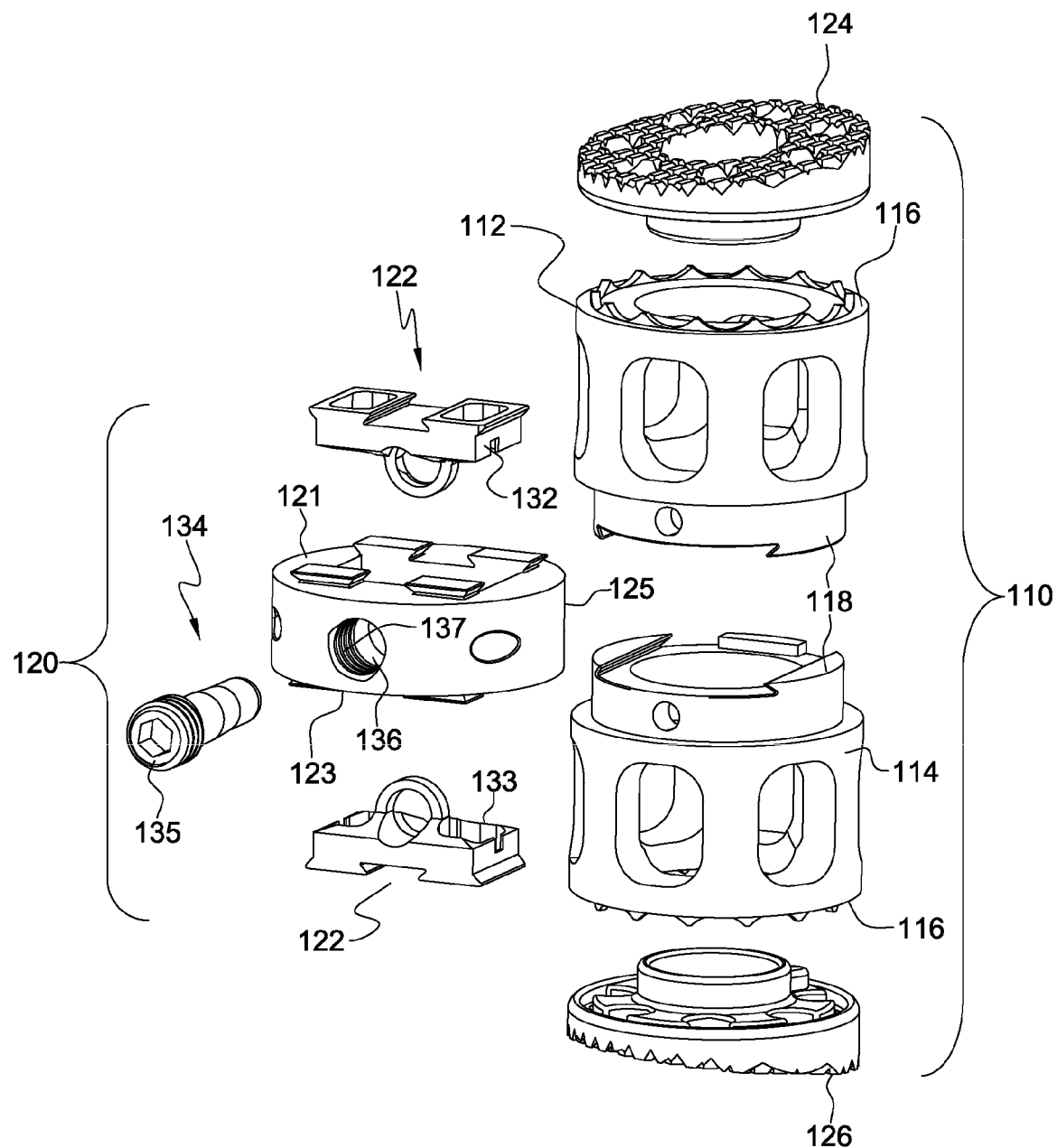
FIG. 25 is an exploded perspective view of the aspect of the invention shown in FIG. 22.

FIG. 25 is an exploded perspective view of a tissue spacer implant 110 shown in FIGS. 22, 23, and 24. As shown in FIG. 25, the intermediate spacer 120 may comprise a cylindrical body 125, and coupling mechanism 122 may include a first or upper coupling plate, or seat plate, 132, a second or lower coupling plate, or seat plate, 133, and means 134 for deflecting the first coupling plate 132 or the second coupling plate 133, or both. For example, the means 134 for deflecting may comprise impinging a camming device 135, such as, a tapered cylinder or wedge, against the first coupling plate 132 or the second coupling plate 133, or both. According to this aspect of the invention, as camming device 135, for example, a rod or pin 135 is inserted into hole 136 in body 125, rod or pin 135 provides a camming effect to encourage deflection of first coupling plate 132 and second coupling plate 134 (see below) to promote engagement of end 121 with first end member 112 and the engagement of second end 123 with second end member 114. As shown in FIG. 25, in one aspect, rod or pin 125 may be a threaded rod or pin adapted to engage an internal thread 137 in hole 136 to effect the desired camming action.

Though not shown in FIG. 25, in one aspect, implant 110 may include one or more reinforcing members, for example, similar to reinforcing members 38 shown in FIG. 4 for implant 10. The reinforcing members may reinforce at least one of end members 112 and 114, for example, to reinforce projections (see below) from end members 112 and 114.

Figure 26:
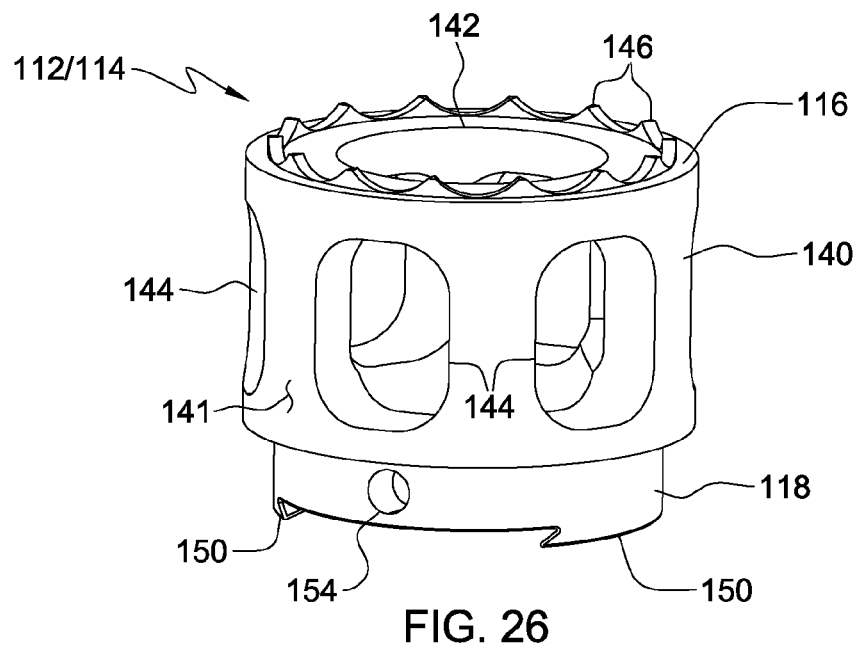
FIG. 26 is top, front perspective view of an end member of the tissue spacer implant shown in FIGS. 22-25 according to an aspect of the present invention.
Figure 27:
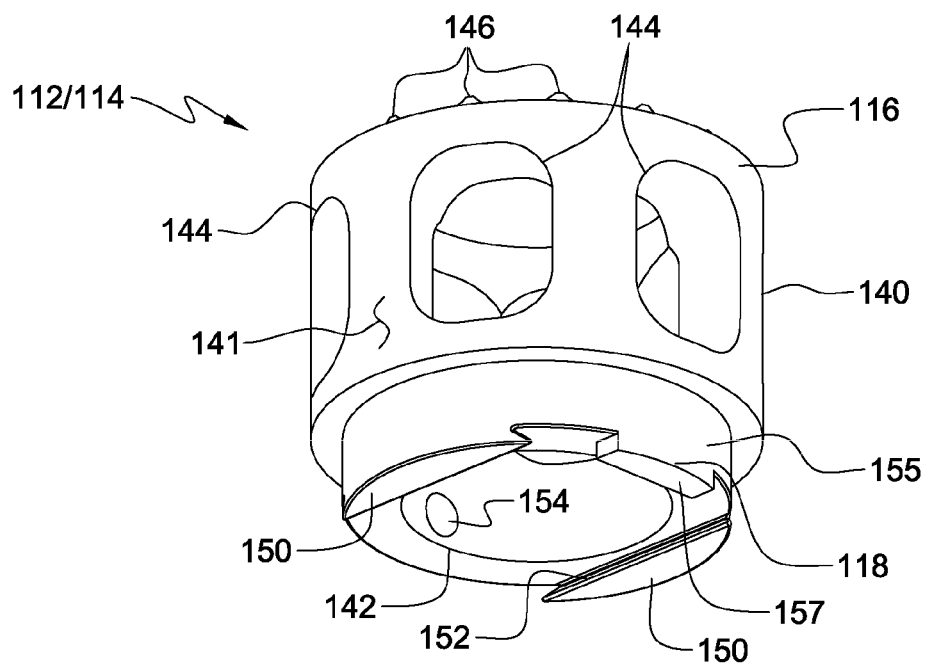
FIG. 27 is a bottom, rear perspective view of the end member shown in FIG. 26.
Figure 28:
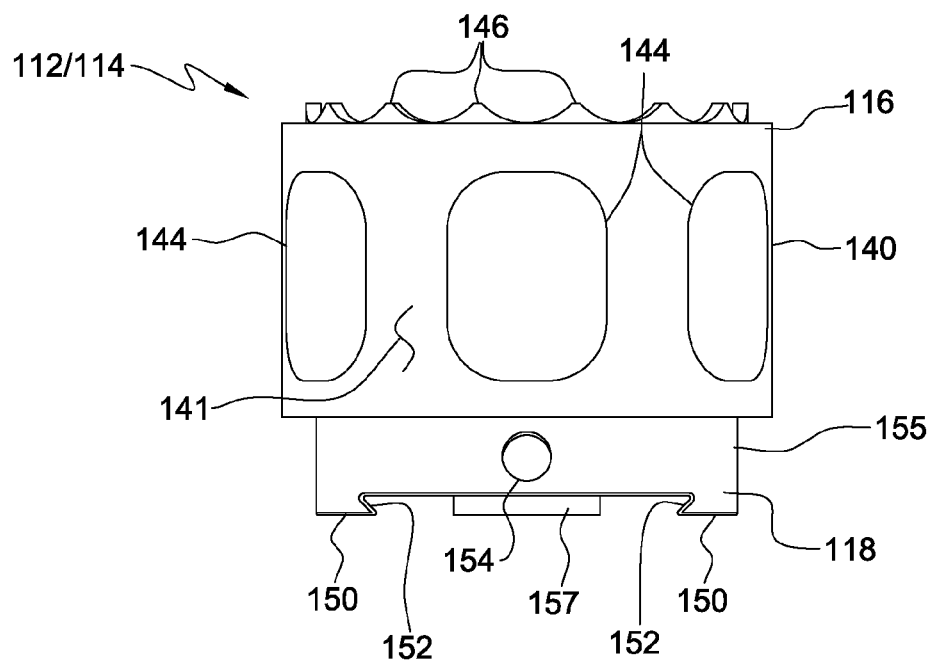
FIG. 28 is a front elevation view of the end member shown in FIG. 26.
Figure 29:
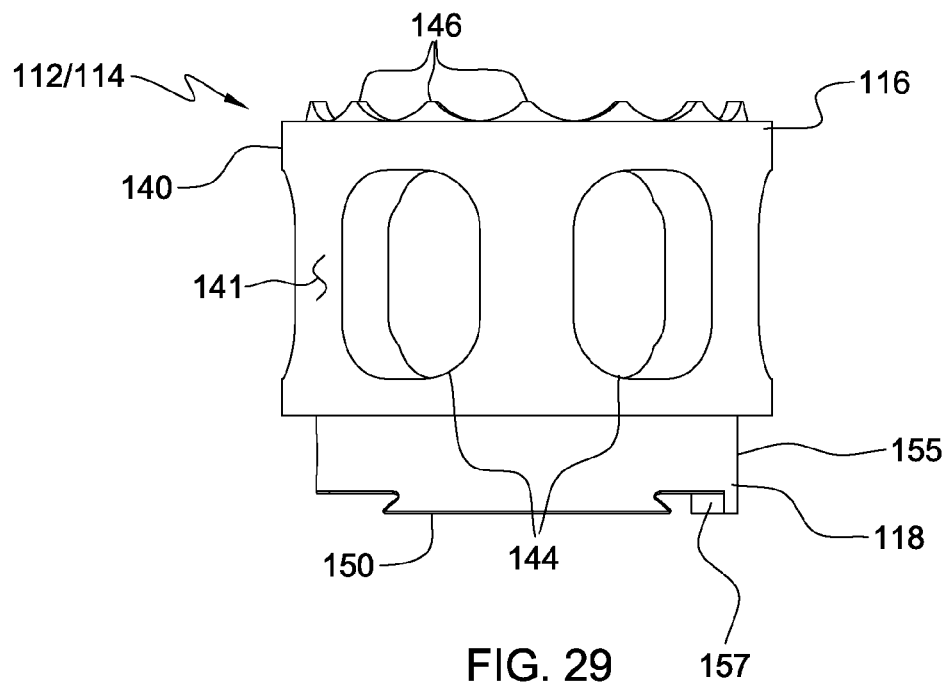
FIG. 29 is a right side elevation view of the end member shown in FIG. 26, the left side elevation view being a mirror image thereof.
Figure 30:
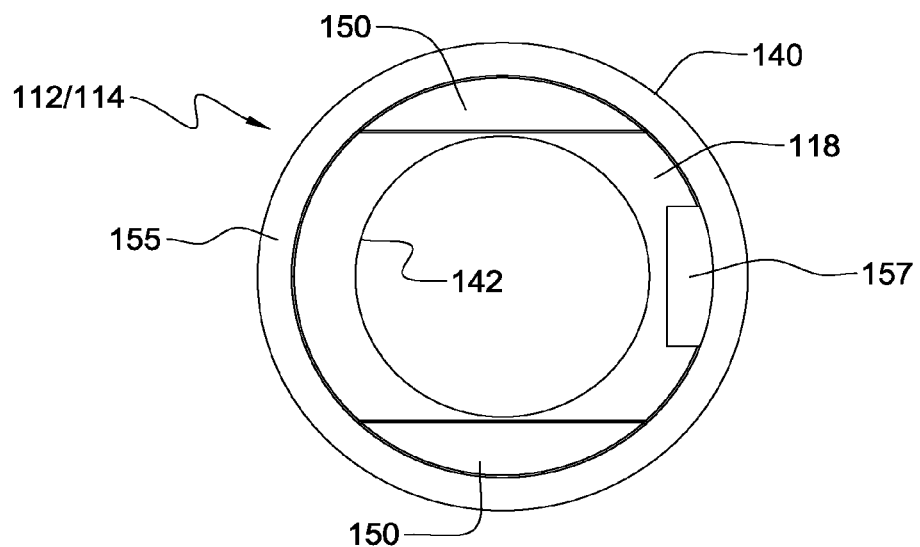
FIG. 30 is a bottom view of the end member shown in FIG. 26.

FIG. 26 is top, front perspective view of an end member 112, 114 of the tissue spacer implant shown in FIGS. 22-25 according to an aspect of the present invention. In one aspect of the invention, end members 112 and 114 may be substantially identical, for example, to minimize manufacturing costs; however, in other aspects, end members 112 and 114 may not be substantially identical. FIG. 27 is a bottom, rear perspective view of the end member 112, 114 shown in FIG. 26. FIG. 28 is a front elevation view of the end member 112, 114 shown in FIG. 26. FIG. 29 is a right side elevation view of the end member 112, 114 shown in FIG. 26, the left side elevation view being a mirror image thereof, and FIG. 30 is a bottom view of the end member 112, 114 shown in FIG. 26.

As shown in FIGS. 26 through 30, end member 112, 114 comprises a generally cylindrical body 140 having and outer surface 141, a first end 116, and a second end 118. Though cylindrical body 140 is shown as a circular cylindrical body, a non-circular cylindrical body may also be used, for example, a polygonal cylindrical or an elliptical cylindrical body may also be provided according to aspects of the invention. It is also conceived that body 140 may be non-cylindrical, for example, having an arbitrary non-cylindrical shape.

As shown in FIGS. 5-9, the body 140 of end member 112, 114 may typically have a hole 142, for example, a central through hole extending from the first end 116 to the second end 18, though hole 142 may not pass completely through body 140, for example, hole 142 may be a blind hole having a bottom. As shown, body 140 may also include a plurality of holes or openings 144 extending from the outer surface 141 to hole 142. Holes or openings 144 may be rectangular with rounded corners, as shown, or may be oval in shape, although many other geometric shapes, for example, circular, elliptical, and polygonal (for example, triangular, square, or hexagonal), are contemplated. Hole 142 and holes 144 may be provided to reduce the weight of end member 112, 114 and/or to promote acceptance of end member 112, 114 by the tissue into which implant 110 is inserted. For example, in one aspect, holes 142 and 144 may be provided to allow introduction of bone graft material, for example, after implantation, to implant 110 to promote adherence to bone.

According to aspects of the invention, first end 116 of end member 112, 114 is adapted to engage tissue (not shown), for example, in one aspect, first end 116 may include projections 146 and/or recesses adapted to engage tissue. However, as shown in FIGS. 22-25, first end 116 may be adapted to accept adapters 124 and 126, for example, "foot plates" 24 and 26, shown in FIGS. 18 and 19. For example, first end 116 may include projections 146 and/or recesses adapted to receive adapters 24 or 26.

According to aspects of the invention, second end 118 of end member 112, 114 is adapted to engage intermediate spacer member 120, as shown in FIGS. 22-25, for example, releasably engage intermediate spacer member 120. Though according to aspects of the invention any means may be provided to promote or provide engagement between second end 118 and the ends 121, 123 of intermediate spacer member 120, in one aspect of the invention, one means comprises projections 150, for example, a pair of opposing projections 150, extending from body 140, for example, axially extending from body 140. Projections 150 may be adapted to engage one or more cooperating recesses and/or projections in one of first end 121 and second end 123 of intermediate spacer member 120. According to aspects of the invention, different kinds of recesses or projections may be used to engage, join, or couple first end 121 and second end 123 with intermediate spacer member 120, including, but not limited to, rails, slots, and channels. As shown in FIGS. 26-30, in one aspect, projections 150 may be beveled projections, for example, having a beveled surface 152. Projections 150 having beveled surfaces 152 may comprise one component of a dove-tail like engagement mechanism, wherein the surfaces 152 engage cooperating surfaces on first end 121 and second end 123 of intermediate spacer member 120 and/or beveled edges on coupling mechanism 124. As shown in FIGS. 26-30, in one aspect, projections 150 of end member 112, 114 may comprise "female" dovetails. In another aspect, projections 150 of end member 112, 114, may also comprise "male" dovetails.

As also shown in FIGS. 26-30, end member 112, 114 may also include features that accommodate an insertion or manipulation tool (not shown). For example, end member 112, 114 may include one or more holes, recesses, or apertures 154 and/or one or more slots, slits, or recesses 155 positioned and adapted to engage a tool, for example, a handling or insertion tool. Engagement and handling of end member 112, 114 with a tool according to an aspect of the invention will be discussed and illustrated below.

End member 112, 114 may also include recesses or projections adapted to limit or enhance engagement of intermediate spacer member 120 with end members 112 and 114. For example, as shown in FIGS. 26-30, end member 112, 114 may include one or more recesses or projections 157 shaped, for example, as pins or bosses, and positioned to engage one or more projections or recesses in intermediate spacer member 120 which limit or act as a "stop" to the engagement with end members 112 and 114, for example, as intermediate spacer member 120 is slidably engaged with end members 112 and 114 as shown in FIG. 24. For example, as shown in FIGS. 31-35, intermediate spacer member 120 may include projections 170 positioned and shaped to engage projections 157 to limit the movement of intermediate member 120 when engaging end members 112 and 114.

As discussed above with respect to FIG. 4, end member 112, 114 may also include reinforcing elements, for example, elongated rods or bars, similar to reinforcing elements 38 shown in FIG. 4, to reinforce at least one of end members 112 and 114, for example, to reinforce projections 150 of end members 112 and 114. Accordingly, in one aspect, end members 112 and 114 may include holes or apertures adapted to receive one or more reinforcing elements. These holes for receiving reinforcing elements may be directed axially into end members 112 and 114, for example, through projections 150 to reinforce projections 150 and minimize or prevent excess deflection of projections 150.

End member 112, 114 may be fabricated from metals and non-metals. For example, in one aspect, end member 112, 114 may be metallic, for example, made from any metal that is resistant to corrosion when exposed to bodily fluids, such as, stainless steel or titanium. In another aspect, end member 112, 114, may be non-metallic, for example, made from a plastic that is resistant to attack when exposed to bodily fluids, such as, a PEEK, a PTFE, or their equivalents. In one aspect, end member 112, 114 may typically be made from FDA approved implant grade materials, such as, implant grade titanium and/or implant stainless steel, or implant grade plastics, such as, PEEK. The size of end member 112, 114 may vary broadly depending upon the size of the cavity or tissue into which implant 10 is to be inserted. For example, end member 112, 114 may have a height or length ranging from about 0.25 to about 6 inches, but is typically between about 0.50 to about 1.5 inches in height or length. Also, the diameter or outside dimension of end member 112, 114 may range from about 0.125 to about 3 inches, but is typically between about 0.50 to about 1.5 inches in outside dimension.

Figure 31:
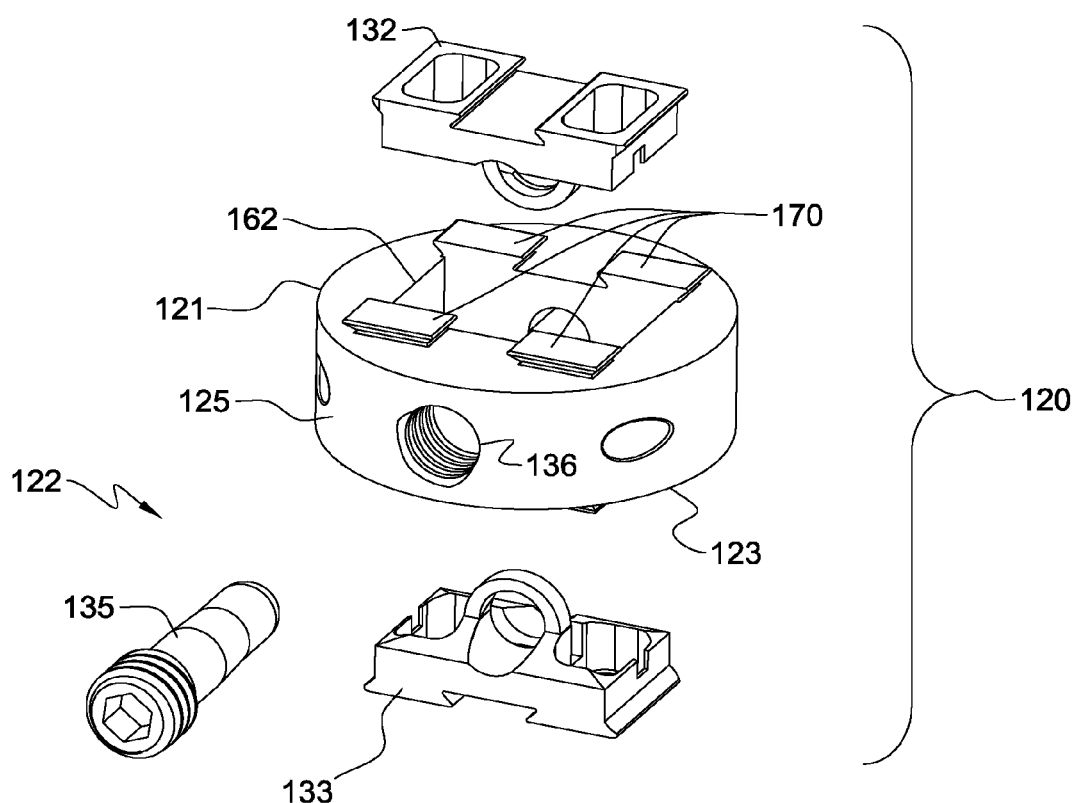
FIG. 31 is an exploded perspective view of the intermediate spacer member and coupling mechanism shown in FIGS. 22 through 24 according to one aspect of the invention.
Figure 32:
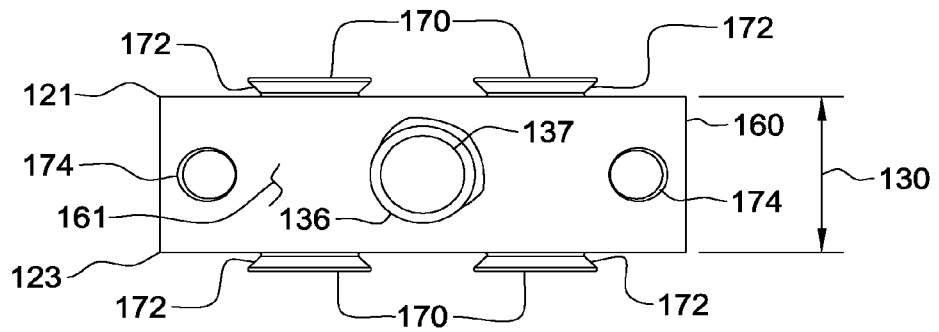
FIG. 32 is a front elevation view of the intermediate spacer member body shown in FIG. 31.
Figure 33:
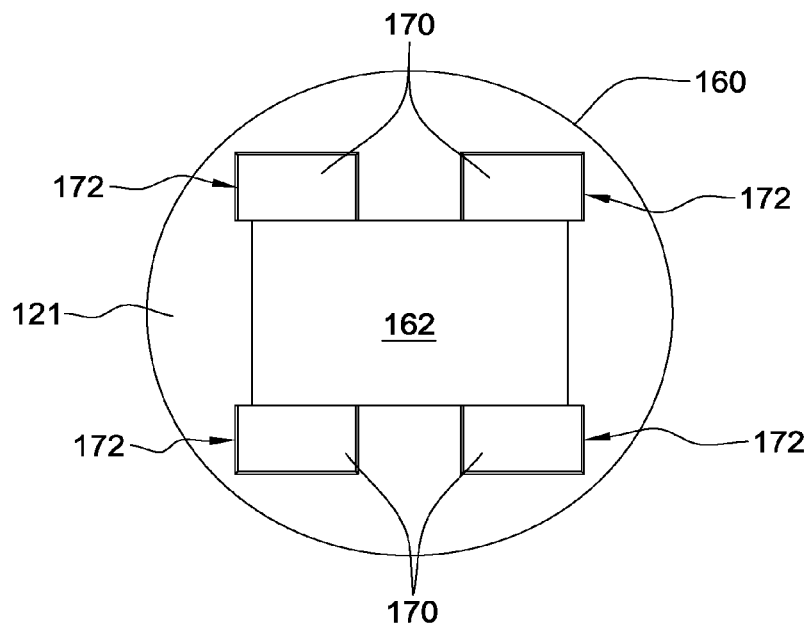
FIG. 33 is a top view of the intermediate spacer member body shown in FIG. 31, the bottom view being a mirror image thereof.
Figure 34:
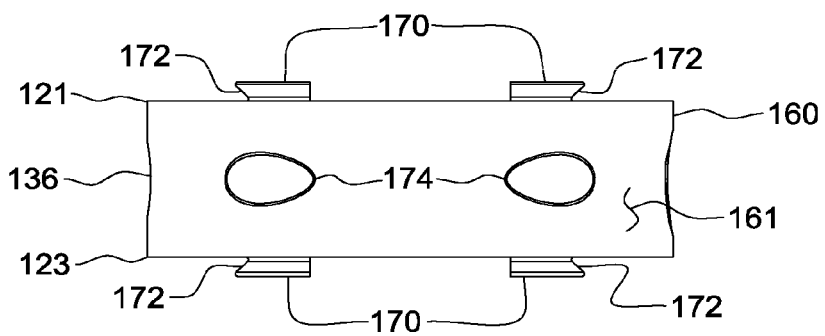
FIG. 34 is a right side elevation view of the intermediate spacer member body shown in FIG. 31, the left side elevation view being a mirror image thereof.

FIG. 31 is an exploded perspective view of the intermediate spacer member 120 and coupling mechanism 122 shown in FIGS. 22 through 24 according to one aspect of the invention. FIG. 32 is a front elevation view of the intermediate spacer member 120 shown in FIG. 31. FIG. 33 is a top view of the intermediate spacer member 120 shown in FIG. 31, the bottom view being a mirror image thereof. FIG. 34 is a right side elevation view of the intermediate spacer member 120 shown in FIG. 31, the left side elevation view being a mirror image thereof.

As shown in FIGS. 32 through 34, intermediate spacer member 120 comprises a generally cylindrical main body 160 having an outer surface 161, a first end 121, and a second end 123 opposite first end 121. Though cylindrical body 160 is shown as a circular cylindrical body, a non-circular cylindrical body may also be used, for example, a polygonal cylindrical or an elliptical cylindrical body may also be provided according to aspects of the invention. It is also conceived that body 160 may be non-cylindrical, for example, having an arbitrary non-cylindrical shape.

As shown in FIGS. 32-34, the body 160 of intermediate spacer member 120 may typically have a hole 162, for example, a central through hole extending from the first end 121 to the second end 123, though hole 162 may not pass completely through body 160, for example, hole 162 may be a blind hole having a bottom. In FIG. 33, hole 162 is shown having a rectangular shape, but hole 162 may take any shape, for example, round, oval, or polygonal, among others. In one aspect, the only restriction to the shape of hole 162 is compatibility of the shape of hole 162 with the shape of coupling plates 132, 133 which, according to one aspect, are inserted into hole 162. Though not shown, body 160 also includes a plurality of holes extending from the outer surface 161 to hole 162. Hole 162 and holes through body 160 may be provided to reduce the weight of intermediate spacer member 120 and/or to promote acceptance by the tissue into which implant 110 is inserted. For example, in one aspect, holes through body 160 may be provided to allow introduction of bone graft material, for example, after implantation, to implant 110 to promote adherence to bone. However, as shown in FIG. 31, hole 162 may also be provided to accommodate features of coupling mechanism 122, for example, to receive coupling plates 132 and 133.

According to aspects of the invention, end 121 and end 123 of intermediate spacer member 120 are adapted to engage end members 112 and 114, respectively, specifically, engage second end 118 of end members 112 and 114, for example, releasably engage second end 118 of end members 112 and 114. Though according to aspects of the invention any means may be provided to promote or provide engagement between ends 121 and 123 and second end 118 and of end members 112 and 114, in one aspect of the invention, one means comprises projections 170, for example, a pair of opposing projections 170, extending from body 160, for example, axially extending from body 160. Projections 170 may be adapted to engage one or more cooperating recesses and/or projections in one of end 116 and/or end 118 of end members 112 and 114. As shown in FIGS. 31-34, in one aspect, projections 170 may provide beveled projections, for example, having a beveled surface 172. Projections 170 having bevel surfaces 172 may comprise one component of a dove-tail like engagement mechanism, wherein the surfaces 172 engage cooperating surfaces on end 116 and/or end 118 of end members 112 and 114. As shown in FIGS. 31-34, in one aspect, projections 170 of intermediate spacer member 120 may comprise "male" dovetails. In another aspect, projections 170 of intermediate spacer member 120 may also comprise "female" dovetails.

In one aspect, projections 170 may be adapted to cooperate with an insertion tool, for example, insertion tool 220 and 420 disclosed below. For example, projections 170 may include a recess 171 adapted to engage an alignment mechanism, for example, rail or projection on an insertion tool to assist in guiding intermediate spacer member 120 into place. However, in one aspect of the invention, recess 171 may be omitted, as indicated in phantom in FIGS. 35-37.

As also shown in FIGS. 31-34, intermediate spacer member 120 may also include features that accommodate an insertion or manipulation tool (not shown). For example, intermediate spacer member 120 may include one or more holes, recesses, slots, slits, or apertures 174 positioned and adapted to engage a tool, for example, a handling or insertion tool. Engagement and handling of intermediate spacer member 120 with a tool according to an aspect of the invention will be discussed and illustrated below.

Intermediate spacer member 120 may also include recesses or projections adapted to limit or enhance engagement of intermediate spacer member 120 with end members 112 and 114. For example, as shown in FIGS. 31-34, intermediate spacer member 120 may include one or more projections or recesses, for example, projections 170, shaped and positioned to engage one or more recesses or projections in end members 112 and 114 which limit or act as a "stop" to the engagement with end members 112 and 114, for example, as intermediate spacer member 120 is slidably engaged with end members 112 and 14 as shown in FIG. 24. For example, as shown in FIGS. 26-30, end members 112 and 114 may include projections 157 positioned and shaped to engage projections 170 to limit the movement of intermediate member 120 when engaging end members 112 and 114.

As discussed above with respect to FIGS. 24 and 25, according to one aspect of the invention, implant 110 includes a coupling mechanism 122 adapted to couple the three components: the first end member 112, the intermediate spacer member 120, and the second end member 114. In one aspect, the coupling mechanism 122 includes a camming device 134, for example, a rod or pin 135, and a set of coupling plates 132 and 133 adapted to be deflected by camming device 134. In one aspect, camming device 134 comprises a tapered cylinder or pin 135 adapted to be inserted into hole 136 and provide a camming effect to encourage the deflection of coupling plates 132 and 133 from the ends 121 and 123 of intermediate spacer member 120 to promote engagement with end members 112 and 114. The details of this camming deflection for coupling plates 132 and 134 are discussed below with respect to FIGS. 41 and 42.

Intermediate spacer member 120 may be fabricated from metals and/or non-metals. For example, in one aspect, intermediate spacer member 120 may be metallic, for example, made from any metal that is resistant to corrosion when exposed to bodily fluids, such as, stainless steel or titanium. In another aspect, intermediate spacer member 120 may be non-metallic, for example, made from a plastic that is resistant to attack when exposed to bodily fluids, such as, a PEEK, a PTFE, or their equivalents. In one aspect, intermediate spacer member 120 may typically be made from FDA approved implant grade materials, such as, implant grade titanium and/or implant stainless steel, or implant grade plastics, such as, PEEK. The size of intermediate spacer member 120 may vary broadly depending upon the size of the cavity or tissue into which implant 110 is to be inserted. For example, intermediate spacer member 120 may have a height or length ranging from about 0.25 to about 6 inches, but is typically between about 0.50 to about 1.5 inches in height or length. Also, the diameter or outside dimension of intermediate spacer member 120 may range from about 0.125 to about 3 inches, but is typically between about 0.50 to about 1.5 inches in outside dimension.

According to one aspect of the invention, a plurality of intermediate spacer members 120 may be provided wherein each of the spacer members 120 may be adapted to couple to end members 112 and 114, for example, as described, while each of the plurality of spacer members 120 are of varying height or length 130 (See FIG. 32.). In one aspect, the plurality of spacer members 120 are provided with regularly varying heights 130, for example, varying in height by 1 millimeter [mm] intervals or 5 mm intervals. This allows the surgeon to determine a desired height of spacer member 120 during surgery, as discussed below, and the desired spacer member 120 of the desired height may be selected from the plurality of spacer members 120 of varying height provided. In one aspect, a kit may be provided having implant 110 having elements, for example, intermediate spacer members 120 and/or end members 112, 114 of varying length, diameter, and/or shape, for example, one or more, geometric cross-sectional shapes.

Figure 35:
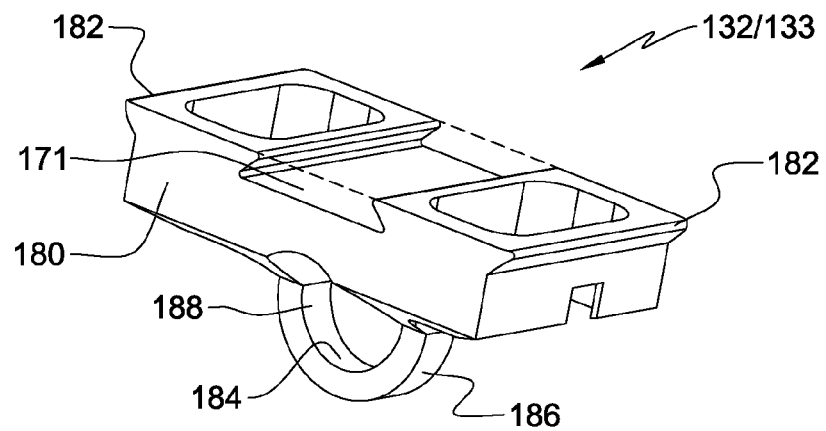
FIG. 35 is a front, top perspective view of a coupling plate shown in FIG. 31 according to one aspect of the invention.
Figure 36:
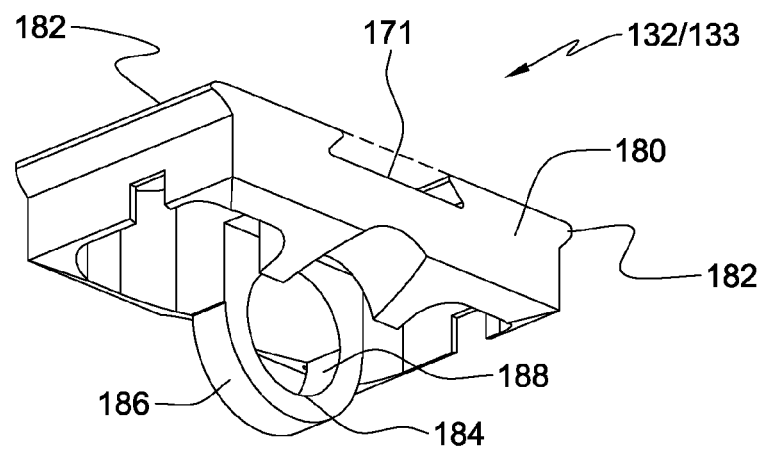
FIG. 36 is a rear, bottom perspective view of the coupling plate shown in FIG. 31.
Figure 37:
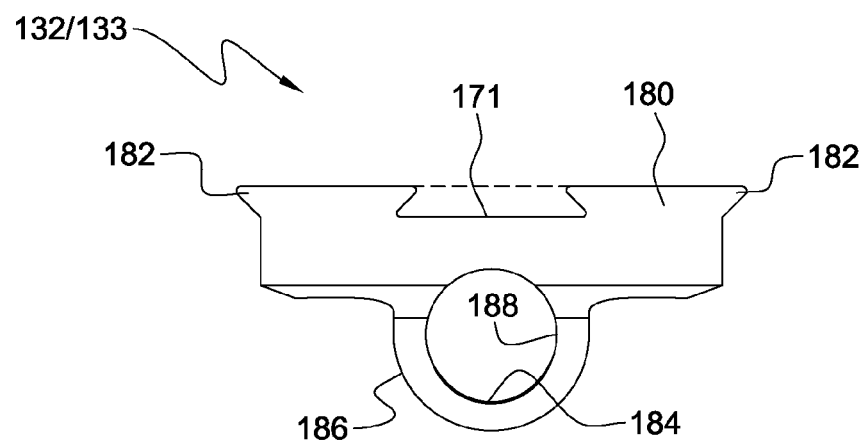
FIG. 37 is a front elevation view of the coupling plate shown in FIG. 31, the rear elevation view being a mirror image thereof.
Figure 38:
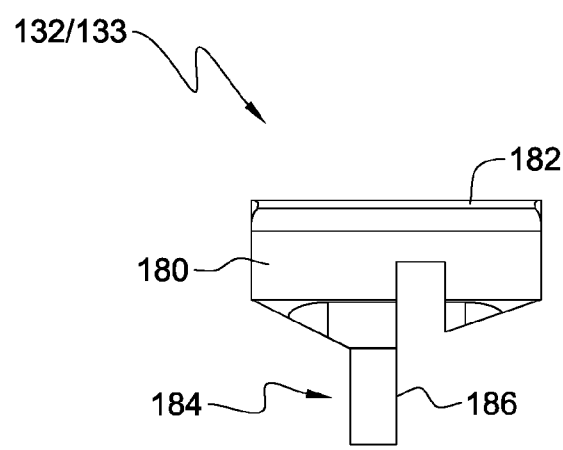
FIG. 38 is a right sided elevation view of the coupling plate shown in FIG. 31, the left side elevation view being a mirror image thereof.

FIG. 35 is a front, top perspective view of a coupling plate 132, 133 shown in FIG. 31 according to one aspect of the invention. In one aspect of the invention, coupling plates 132, 133 may be substantially identical, for example, to minimize manufacturing costs; however, in other aspects, coupling plates 132, 133 may not be substantially identical. FIG. 36 is a rear, bottom perspective view of the coupling plate 132, 133 shown in FIG. 31. FIG. 37 is a front elevation view of the coupling plate 132, 133 shown in FIG. 31, the rear elevation view being a mirror image thereof. FIG. 38 is a right sided elevation view of the coupling plate 132, 133 shown in FIG. 31, the left side elevation view being a mirror image thereof.

As shown in FIGS. 35-38, coupling plate 132, 133 comprises a main body 180, two opposing projections 182 from main body 180, and a camming surface 184 mounted to main body 180. According to one aspect of the invention, camming surface 184 may be positioned anywhere on main body 180 whereby, when contacted by an appropriate camming device, for example, camming device 135 shown in FIGS. 39 and 40, deflects coupling plates 132, 133 whereby projections 182 are impinged against opposing surfaces to encourage engagement of coupling plate 132, 133 with the opposing surfaces, for example, the beveled surfaces 152 of end members 112, 124. A description of one engagement of coupling plate 132, 133 is provided below with respect to FIGS. 41 and 42.

In the aspect of the invention shown in FIGS. 35-38, main body 180 of coupling plate 132, 133 substantially comprises a rectangular body, for example, a rectangular body adapted to comply with the rectangular shape of hole 162 in intermediate spacer member 120 (see FIG. 33). However, it is understood that main body 180 may assume many different geometric shapes, including circular cylindrical, oval cylindrical, or polygonal cylindrical, and hole 162 may assume a complementary shape to accommodate main body 180. In addition, the two opposing projections 182 from main body 180 may also be provided in a variety of configurations, for example, as long as they engage complementary surfaces which are coupled by coupling plates 132, 133. For example, projections 182 may comprise beveled surfaces as shown in FIGS. 35-38, but may comprise non-beveled projections, or one or more pins, tabs, bosses, and the like.

In addition, camming surface 184 mounted to main body 180 may also take any convenient shape or location on body 180, for example, integrally mounted on body 180. According to an aspect of the invention, camming surface 184 is positioned to cooperate with a camming device, for example, camming device 135 shown in FIGS. 39 and 40. In the aspect of the invention shown in FIGS. 35-38, camming surface 184 comprises an internal surface of a hollow projection or ring 186, specifically, a projection integrally mounted to and projecting from body 180 and having a through hole or bore 188. In the aspect of the invention shown in FIGS. 35-38, projection 186 comprises a substantially circular projection 186 having a circular though hole 188, for example, a circular bore adapted to receive a circular camming device, for example, camming device 135 shown in FIGS. 39 and 40. However, according to aspects of the invention, projection 186 may take any shape while providing camming surface 184. For example, projection 186 may be elliptical or polygonal, for example, triangular, square, or rectangular and provide a through hole 188 providing a camming surface 184. Through hole or bore 188 may also be elliptical or polygonal, for example, triangular, square, or rectangular, depending upon the shape of the camming device with which camming surface 184 cooperates with. For example, the camming device may be circular as well as elliptical or polygonal, for example, triangular, square, or rectangular, according to aspects of the invention.

Coupling plates 132, 133 may be fabricated from metals or non-metals. For example, in one aspect, coupling plates 132, 133 may be metallic, for example, made from any metal that is resistant to corrosion when exposed to bodily fluids, such as, stainless steel or titanium. In another aspect, coupling plates 132, 133 may be non-metallic, for example, made from a plastic that is resistant to attack when exposed to bodily fluids, such as, a PEEK, a PTFE, or their equivalents. In one aspect, coupling plates 132, 133 may typically be made from FDA approved implant grade materials, such as, implant grade titanium and/or implant stainless steel, or implant grade plastics, such as, PEEK. The size of coupling plates 132, 133 may vary broadly depending upon the size of implant 110. For example, coupling plates 132, 133 may have a length, width, and height ranging from about 0.25 inches to about 5 inches, but the length, width, and height is typically between about 0.75 inches to about 1.50 inches.

Figure 39:
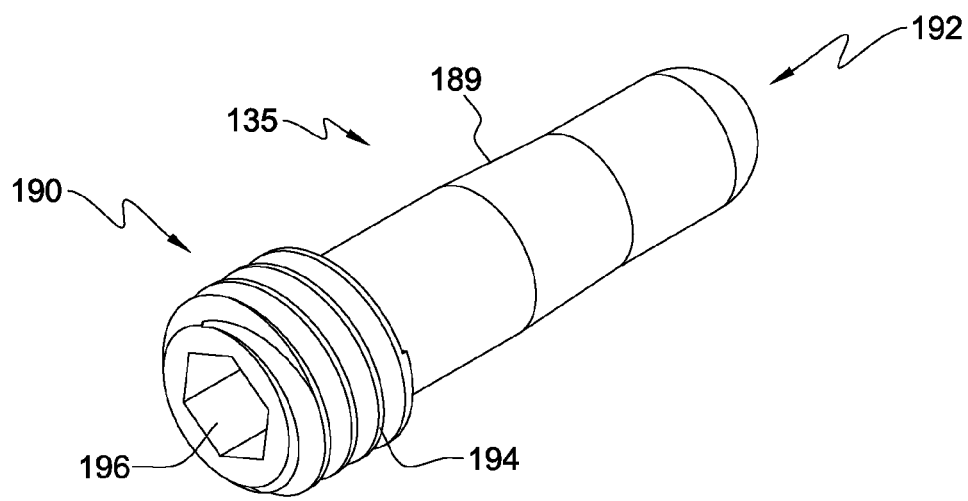
FIG. 39 is a perspective view of the camming device shown in FIG. 31 according to one aspect of the invention.
Figure 40:
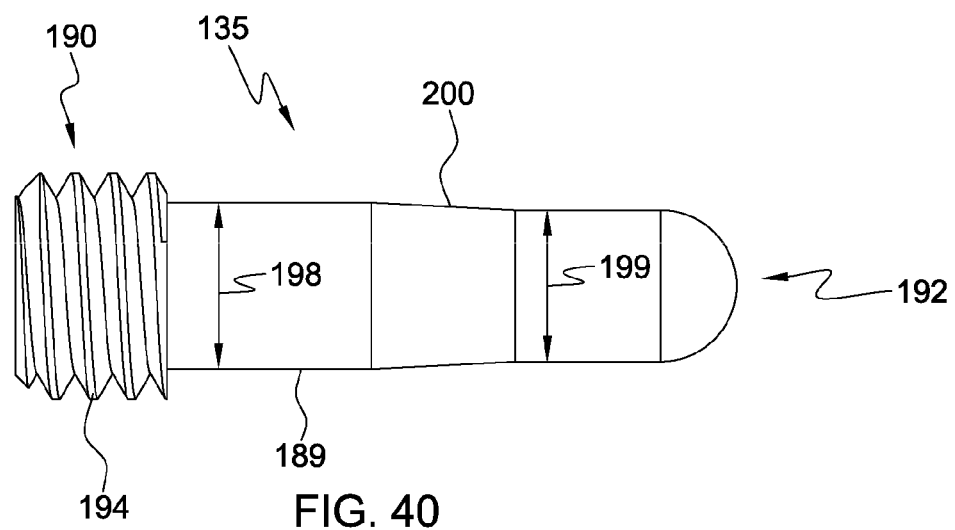
FIG. 40 is a side elevation view of the camming device shown in FIG. 39.

FIG. 39 is a perspective view of one camming device 135 shown in FIG. 31 according to one aspect of the invention. FIG. 40 is a side elevation view of the camming device 135 shown in FIG. 39. Though other devices which are adapted to be inserted to engage camming surface 184 in coupling plates 132, 133 may be used, FIGS. 39 and 40 illustrate one camming device 135 that may be used. Camming device 135 may be provided in any convenient cross-sectional shape, for example, circular, oval, or rectangular. In the aspect shown in FIGS. 39 and 40, camming device 135 comprises a circular pin or rod adapted to be inserted into bore 188 of coupling plate 132, 133.

As shown, camming device 135 comprises as circular cylindrical body 189 having a first end 190 and a second end 192 opposite first end 190. In this aspect, first end 190 includes a plurality of screw threads 194 adapted to engage internal threads 137 of hole 136 in intermediate spacer member 120, and a recess 196 adapted to engage a tool, for example, a hex head drive. Second end 182 is tapered or beveled to facilitate insertion of camming device 135 into hole 136 and bore 188. As shown most clearly in FIG. 40, cylindrical body 189 may vary in diameter, for example, from a first diameter 198 to a second diameter 199, and provide a camming surface 200 of varying diameter between first diameter 198 and second diameter 199, for example, comprising circular frustum of varying diameter, such as, a right circular frustum. According to aspects of the invention camming surface 200 of varying diameter comprises a camming surface adapted to engage a corresponding camming surface on coupling plate 132, 133 to provide engagement between intermediate body member 120 and end members 112, and 113.

Camming device 135 may be fabricated from metals or non-metals. For example, in one aspect, camming device 135 may be metallic, for example, made from any metal that is resistant to corrosion when exposed to bodily fluids, such as, stainless steel or titanium. In another aspect, camming device 135 may be non-metallic, for example, made from a plastic that is resistant to attack when exposed to bodily fluids, such as, a PEEK, a PTFE, or their equivalents. In one aspect, camming device 135 may typically be made from FDA approved implant grade materials, such as, implant grade titanium and/or implant stainless steel, or implant grade plastics, such as, PEEK. The size of camming device 135 may vary broadly depending upon the size of implant 110. For example, camming device 135 may have a length ranging from about 0.25 inches to about 5 inches, but is typically between about 0.75 inches to about 1.50 inches in length. Also, the diameter or outside dimension of camming device 135 may range from about 0.125 inches to about 2 inches, but is typically between about 0.25 inches to about 0.50 inches in outside dimension.

According to this aspect of the invention, as camming device 135 is inserted into hole 136 and into the bores 188 of coupling plates 132, 133, camming device 135 provides a camming effect to encourage the deflection of coupling plates 132, 133 whereby intermediate body member 120 and end members 112 and 113 are engaged, for example, rigidly fixed to each other. As shown in FIG. 31 in one aspect, camming device 135 may be a threaded into internal thread 137 in hole 136 to effect the desired camming action.

Figure 41:
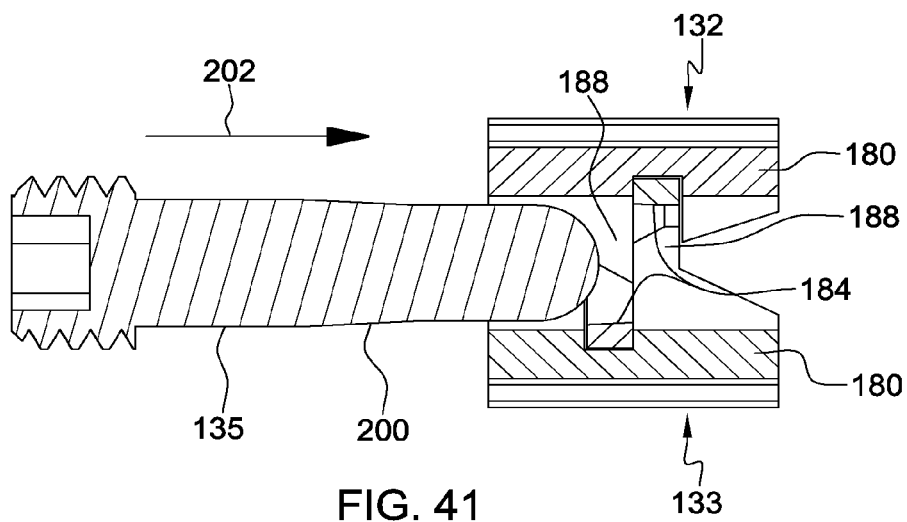
FIG. 41 is a cross-sectional view of an assembly of the coupling plates and coupling mechanism shown in FIG. 31 illustrating the initial engagement of the camming device shown in FIGS. 39 and 40 with the coupling plates shown in FIGS. 35 through 38.

FIG. 41 is a cross-sectional view of an assembly of the coupling plates 132, 133 and coupling mechanism 122 shown in FIG. 31 illustrating the initial engagement of the camming device 135 shown in FIGS. 39 and 40 with the coupling plates 132, 133 shown in FIGS. 35 through 38. As shown in FIG. 41, camming device 135 is inserted into bores 188 of coupling plates 132, 133, for example, while being threaded into hole 136 (not shown), and camming surface 200 on camming device 135 is directed toward camming surfaces 184 on coupling plates 132 and 133.

Figure 42:
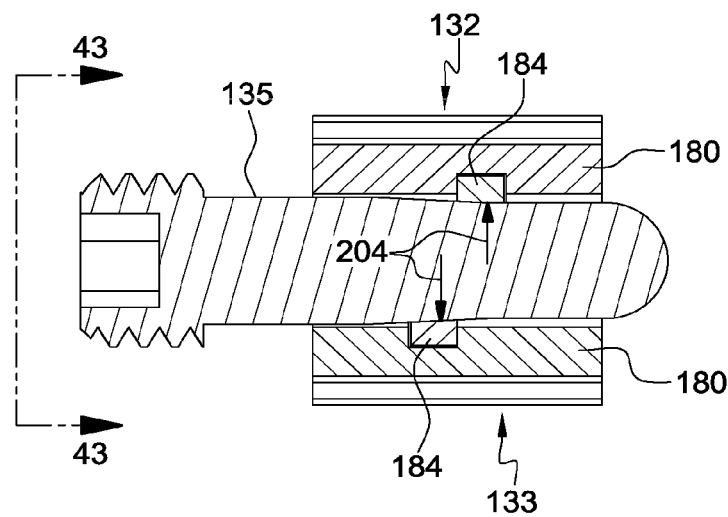
FIG. 42 is a cross-sectional view of the assembly shown in FIG. 41 illustrating the substantially full engagement of the camming device with the coupling plates.

FIG. 42 is a cross-sectional view of the assembly shown in FIG. 41 illustrating the substantially full engagement of the camming device 135 with the coupling plates 132 and 133. As shown in FIG. 42, when camming surface 200 of camming device 135 contacts camming surfaces 184 on coupling plates 132 and 133, camming surface 200 imposes a contact force 204 upon camming surfaces 184. The contact force 204 on the camming surface 184 of the upper coupling plate 132 draws the coupling plate 132 downward, as shown for example in FIG. 42. At substantially the same time, this contact force 204 on the camming surface 184 of the lower coupling plate 133 draws the lower coupling plate 133 upward, as shown for example in FIG. 42. The result of this interaction between camming device 135 and coupling plates 132 and 133 is shown in FIG. 43.

Figure 43:
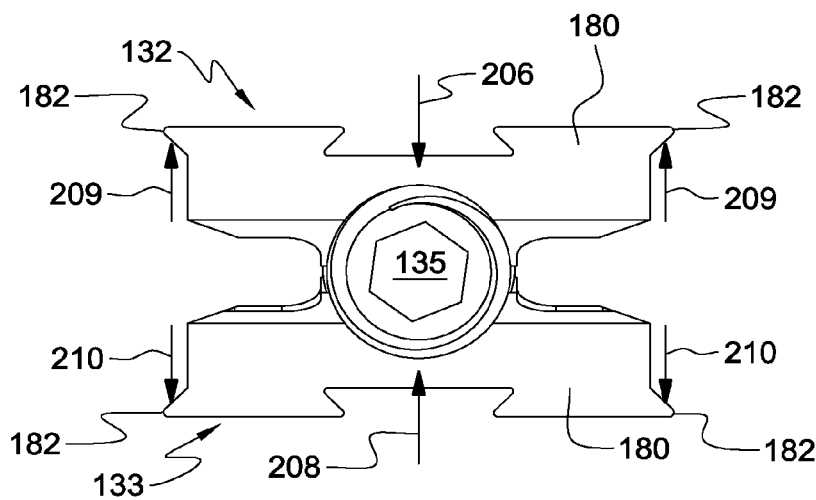
FIG. 43 is a front elevation view of the assembly shown in FIG. 42 as viewed along view lines 43-43 in FIG. 42.

FIG. 43 is a front elevation view of the assembly shown in FIG. 42 as viewed along view lines 43-43 in FIG. 42. As shown in FIG. 43, the contact force 204 (see FIG. 42) on the camming surface 184 of the upper coupling plate 132 draws the upper coupling plate 132 downward, as indicated by arrow 206 in FIG. 43. According to aspects of the invention, this relative movement as indicated by arrows 206 and 208, however small, induces a contact force between projections 182 of upper coupling plate 132 and a surface adjacent projection 182, for example, the surface 152 of projection 150 of end member 112 (See FIG. 28), as indicated by arrow 209. At substantially the same time, this relative movement as indicated by arrows 206 and 208, however small, induces a contact force between projections 182 of lower coupling plate 133 and a surface adjacent projection 182, for example, the surface 152 of projection 150 of end member 112 (See FIG. 28), as indicated by arrow 209. That is, according to aspects of the invention, the insertion of camming device 135 into the bores 188 of assembled coupling plates 132, 133, for example, assembled within hole 162 of intermediate spacer member 120, deflects coupling plates 132 and 133 whereby the projections 182 of coupling plates 132 and 133 are drawn toward, for example, firmly toward, surface 152 of end members 112 and 114 whereby end members 112 and 114 are coupled to intermediate spacer member 120. Moreover, according to aspects of the invention, this coupling is reversible, for example, by unthreading camming device 135 from intermediate spacer member 120, whereby intermediate spacer member 120 can be uncoupled and removed from end members 112 and 144, and, as appropriate, replaced by a different intermediate spacer member 120, for example, of a different size.

Figure 44:
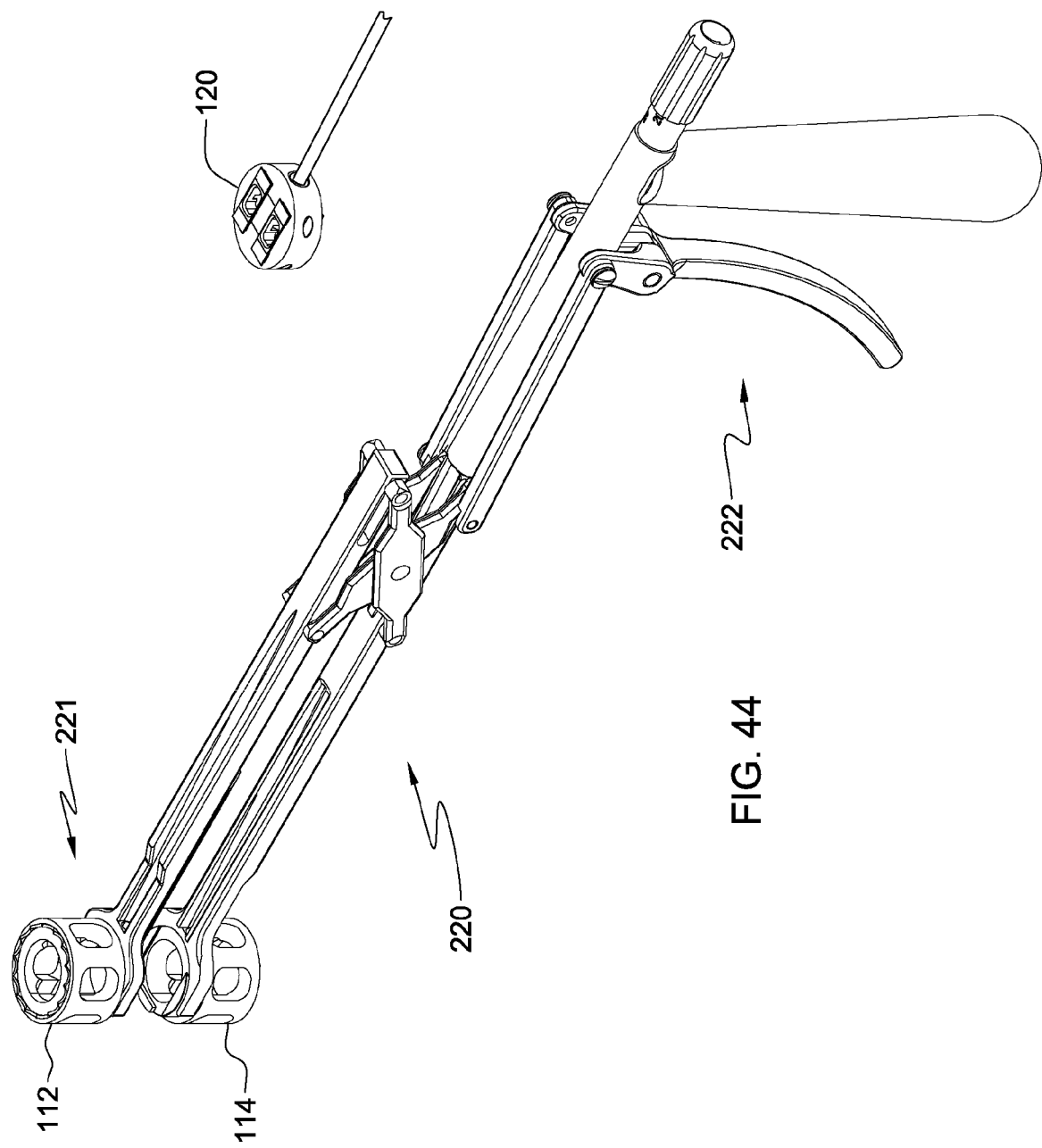
FIG. 44 is a perspective view of another insertion tool that can be used to implant a tissue spacer implant according to an aspect of the present invention.
Figure 45:
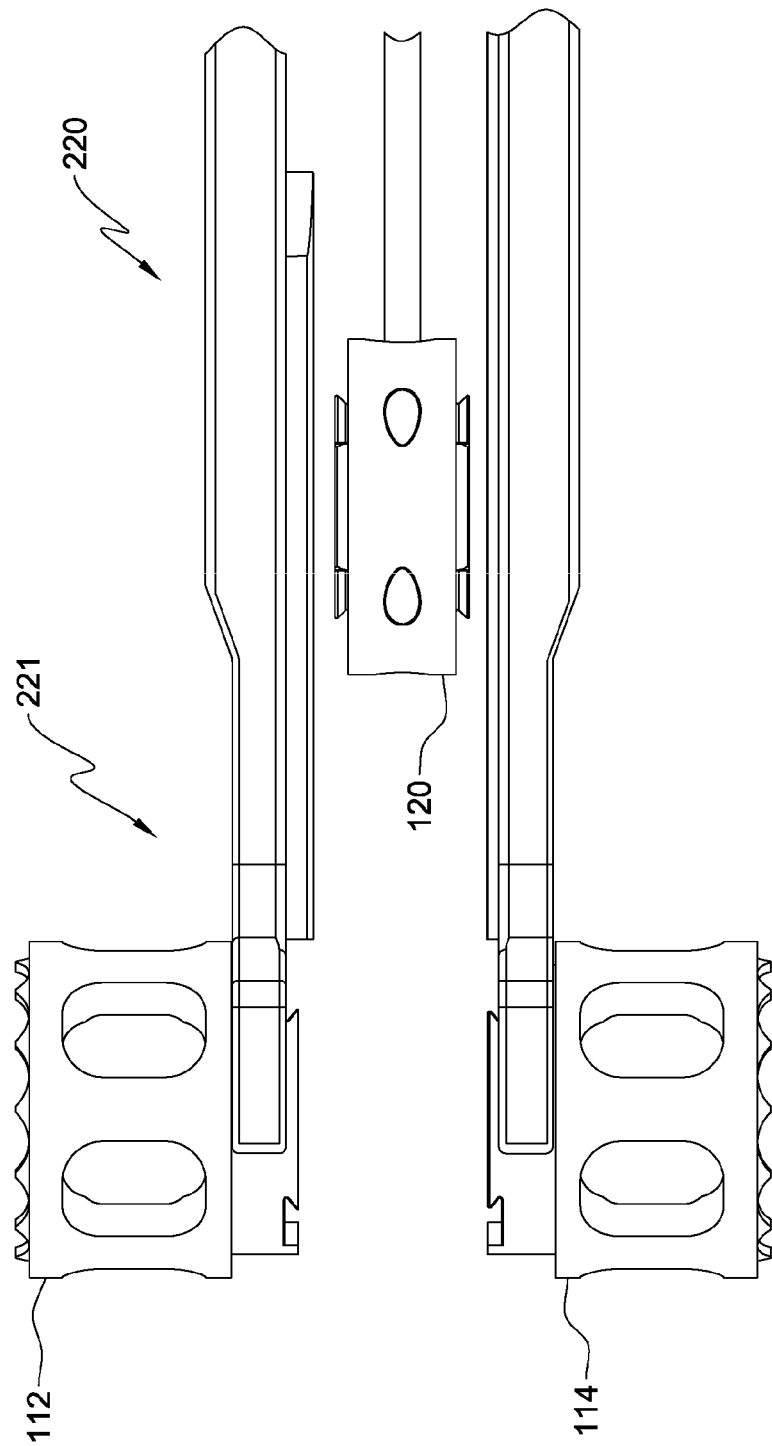
FIG. 45 is a detailed perspective view of the tool shown in FIG. 43 illustrating one means of implanting the tissue space shown in FIGS. 22 through 25.

In a fashion similar to implant 10 shown in FIGS. 20 and 21, implant 110 may also be handled by an insertion tool during surgery. FIG. 44 is a perspective view of a typical insertion tool 220 that can be used to implant the tissue spacer 110 according to an aspect of the present invention. FIG. 45 is a detailed side elevation view of the tool 220 shown in FIG. 44 illustrating one means of implanting the tissue space 110 shown in FIGS. 22 through 43. A detailed description of insertion tool 220 is provided below with respect to FIGS. 62 through 67.

As shown in FIG. 45, according to aspects of the invention, tissue spacer 110 may be inserted between tissue, for example, between two vertebrae, by first mounting end members 112 and 114 to the working or proximal end 221 of tool 220. As will be discussed further below, the separation of end members 112 and 114 can be varied by manipulating hand lever assembly 228 of tool 220. According to aspects of the invention, once the separation of end members 112 and 114 is determined (for example, as a function of the spacing between vertebrae), an appropriately sized intermediate spacer member 120 can be selected by the surgeon, for example, from a plurality of spacer members 120 and inserted between end members 112 and 114 with the aid of insertion tool 220, for example, as illustrated in FIG. 24 above. Once properly placed between end members 112 and 114, coupling mechanism 122 of intermediate spacer member 120, for example, having camming device 135, is activated using a tool head incorporated into insertion tool 220 to secure intermediate spacer member 120 to end members 112 and 114 as described above. Again, detailed aspects of tool 220 and its operation with respect to implant 110 will be provided below with respect to FIGS. 62 through 67.

Aspects of the surgical method for using the tissue spacer implant 10, 110, for example, the appropriate surgical exposure and dissection techniques, are well known in the art. However, novel aspects of the present invention include obtaining the properly sized and configured end members 12, 14, 112, 114 and attaching these end members to a distraction/insertion tool, for example, one of the tools described below. Following the attachment of the end members 12, 14, 212, 214 to the distraction tool, the end members are placed between two tissue bodies. For example purposes only, the following description references a technique used in the replacement of a missing vertebral body, though aspects of the invention may be applied to any tissue, for example, in a living being. The ends of the distraction tool with the coupled and aligned end members 12, 14, 212, 214 are positioning within a space within a spinal column with both end members 12, 14, 212, 214 engaging respective adjacent vertebral bodies. Upon completion of the distraction step or maintenance of the existing space with the instrument and calculation of the necessary thickness of the intermediate spacer member 20, 216, the appropriate sized intermediate spacer member 20, 216 is sliding engaged with the distraction instrument and the member 20, 216 is oriented and tracked into the space between the end members 12, 14, 212, 214 allowing the coupling mechanism 22, 122 to mate with the corresponding end member. Accordingly, the implants 10, 110 are assembled into a final single construct.

FIGS. 45-67 illustrate various tools and methods of using the tools that can be used to surgically implant a tissue spacer device, for example, the tissue spacer implants 10 or 110 described above, according to another aspect of the invention. In general, the implant tool disclosed below is a surgical instrument for use in inserting an implant into a space between two tissue bodies, for example, two vertebrae. More specifically, though according to aspects of the invention, the surgical instruments disclosed herein may typically be used to distract and/or maintain a space between any two tissue bodies so that a tissue spacer implant may be inserted between the two tissue bodies, according to other aspects of the invention, the disclosed tool may be used to distract and/or maintain a space between any two tissue bodies, for example, between any two tissue bodies in a living organism. The surgical instruments generally include a handle, an actuator, two elongated members that include implant engagement ends and a distraction mechanism. The surgical instrument may further include a tissue space indicator and spacer insertion mechanism or tool.

As used herein, the terms "surgical instrument," "surgical tool," "distraction tool," "inserter," or "distractor" may be used interchangeably as they substantially describe the same type of operative instrument. Furthermore, described herein are a surgical method for using the surgical instrument, a method of fabricating the surgical instrument and a tissue spacer implant insertion kit that may be used to maintain a space between two tissue bodies within a patient suffering from a diseased or compromised structural element.

Figure 46:
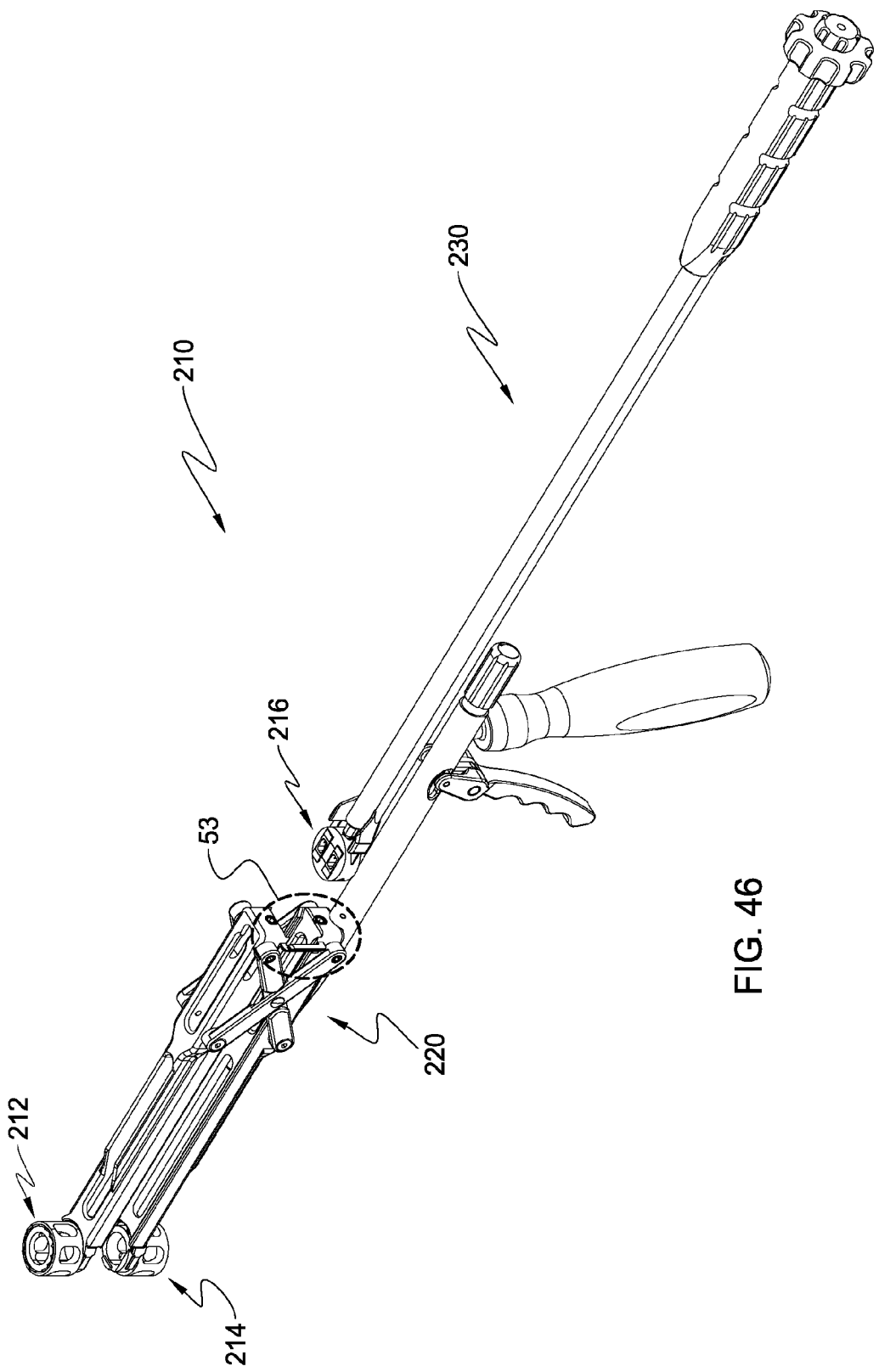
FIG. 46 is a perspective view of a surgical tool assembly according to another aspect of the invention which can be used to implant a tissue spacer implant.
Figure 47:
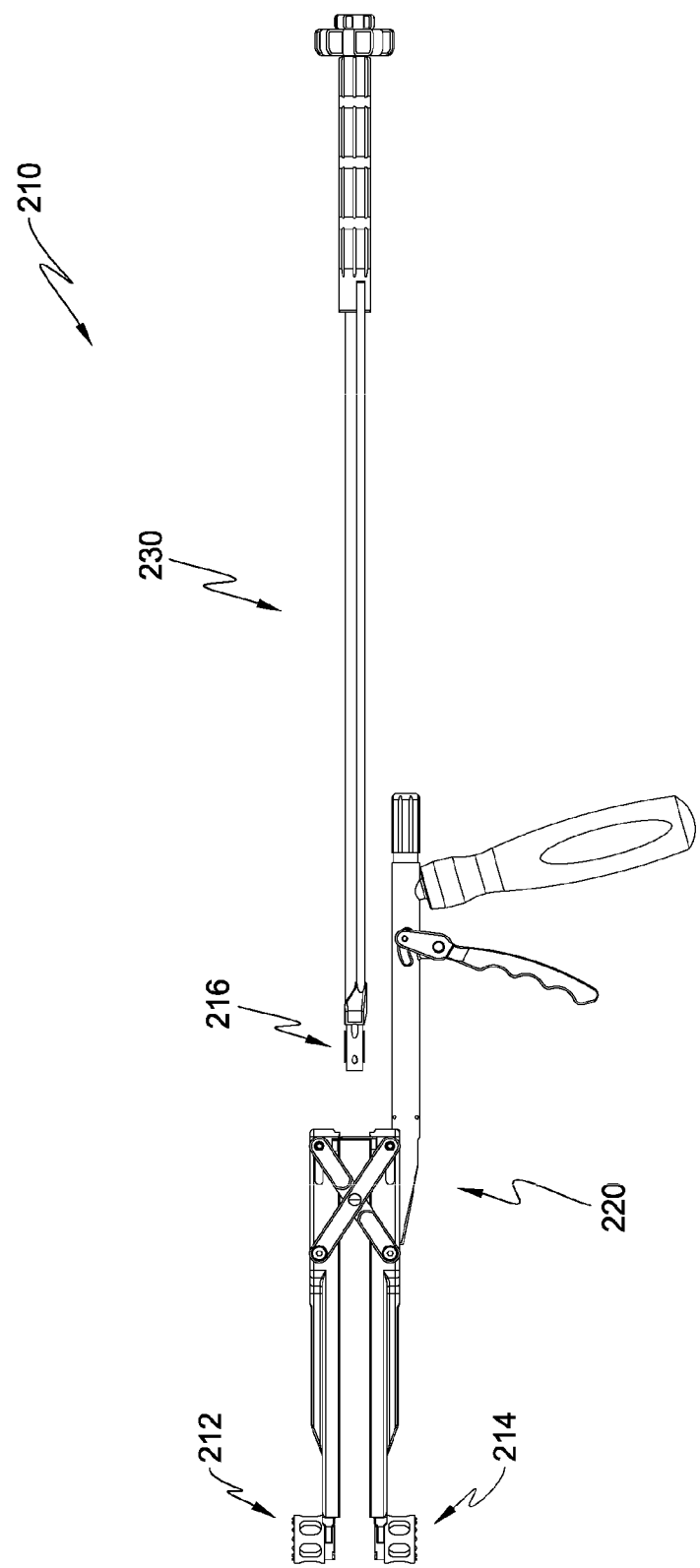
FIG. 47 is a side elevation view of the tool assembly shown in FIG. 46.

FIG. 46 is a perspective view of a surgical tool assembly 210 according to an aspect of the invention which can be used to implant a tissue spacer implant, for example, to insert tissue spacer implant 10 or 110 disclosed above. FIG. 47 is a side elevation view of the tool assembly 210 shown in FIG. 46. As shown, according to one aspect, tool assembly 210 includes a distraction tool 220 and an insertion tool 230 that are adapted to insert a first end member 212, a second end member 214, and an intermediate spacer member 216 of a spacer implant.

Figure 48:
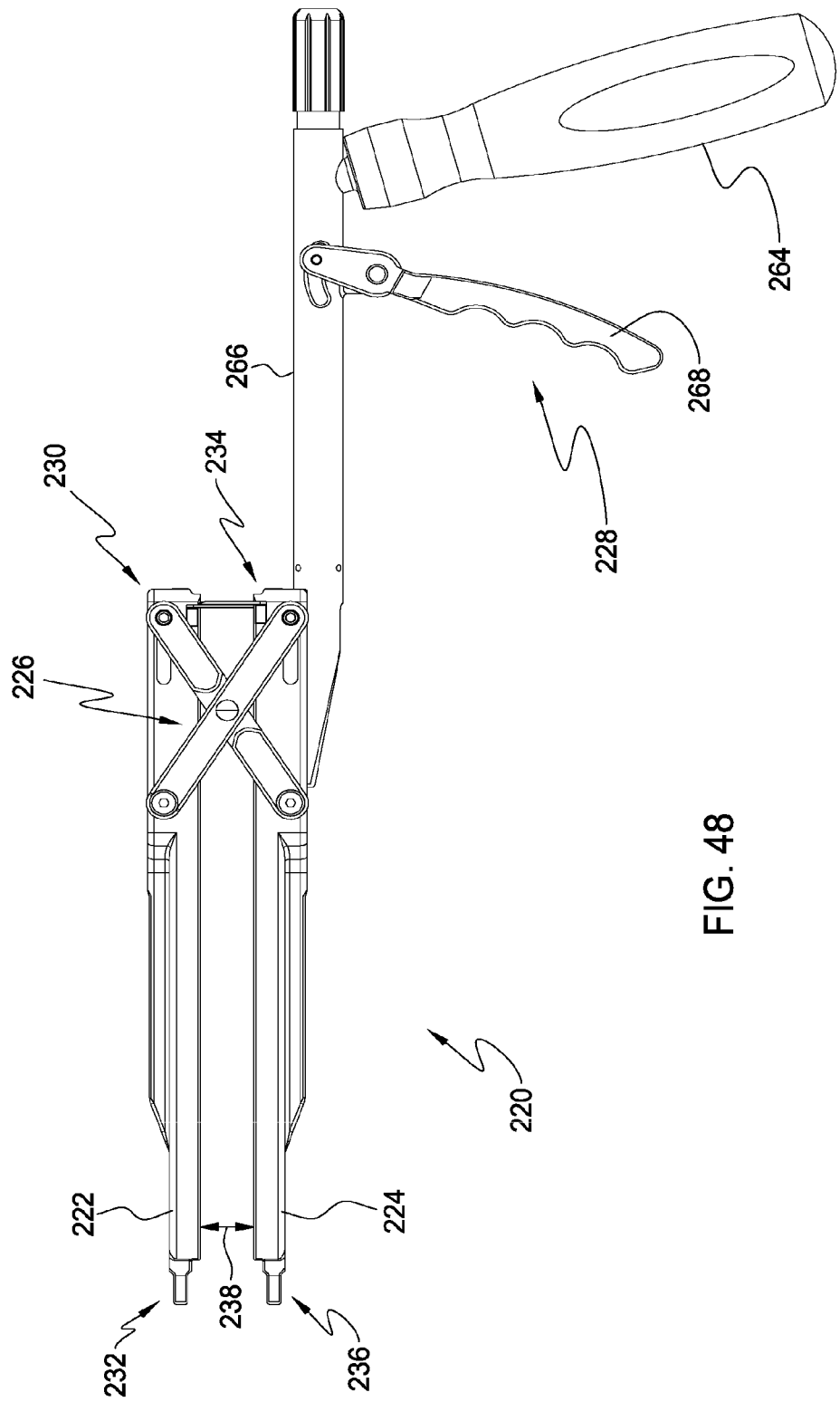
FIG. 48 is a side elevation view of the distraction tool shown in FIGS. 46 and 47.
Figure 49:
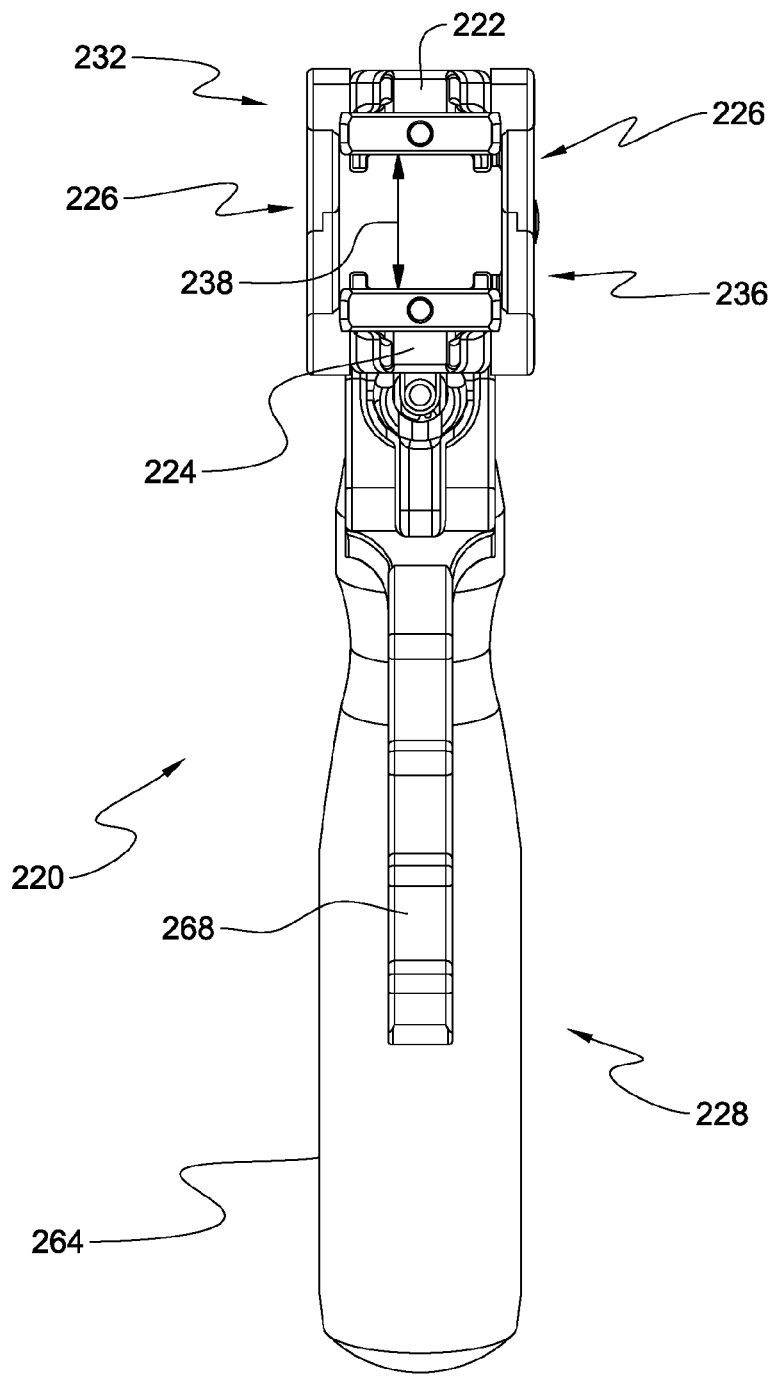
FIG. 49 is a left end elevation view of distraction tool shown in FIG. 48.
Figure 50:
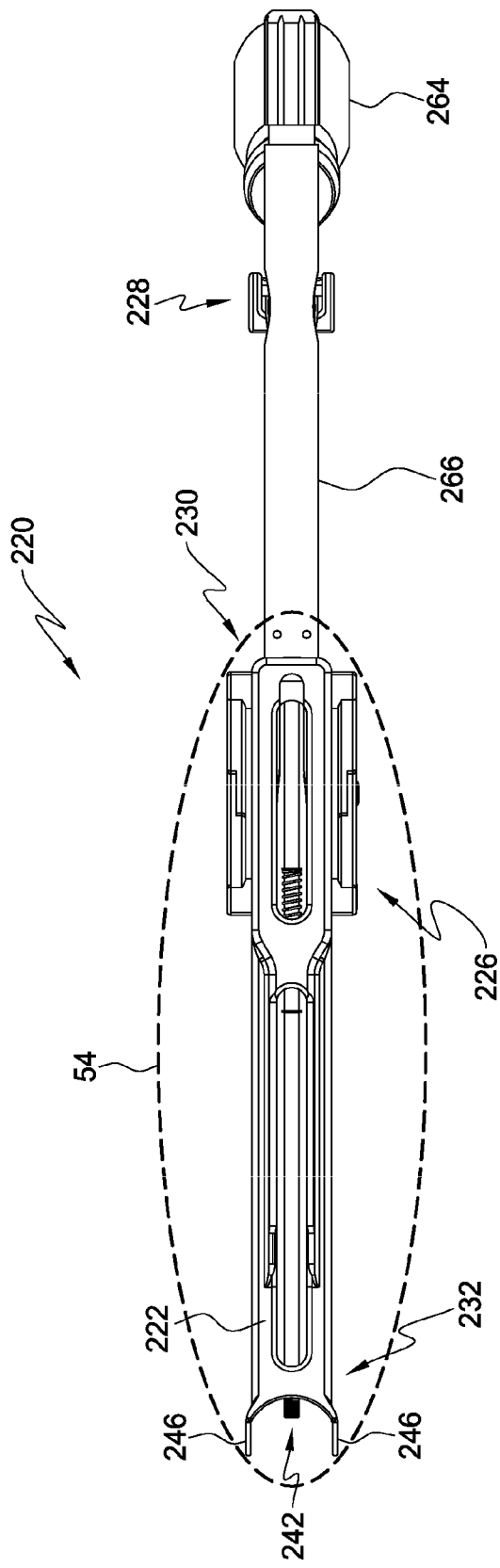
FIG. 50 is a top view of the distraction tool shown in FIG. 48.

FIG. 48 is a side elevation view of the distraction tool 220 shown in FIGS. 46 and 47. FIG. 49 is a left end elevation view of the distraction tool 220 shown in FIG. 48 and FIG. 50 is top view of distraction tool 220 shown in FIG. 48. As shown in FIGS. 48-50, distraction tool 220 includes a first elongated member 222, a second elongated member 224, a distraction mechanism 226, and an actuator 228. First elongated member 222 includes a distal end 230 and a proximal end 232. Proximal end 232 is typically adapted to receive a first end member of an implant (not shown in FIG. 48, but see, for example, end member 212 shown in FIGS. 46 and 47). Second elongated member 224 similarly includes a distal end 234 and a proximal end 236. Proximal end 236 is typically adapted to receive a second end member of the implant (again, not shown, but see, for example, end member 214 shown in FIGS. 46 and 47). The distraction mechanism 226 is operatively connected to the first elongated member 222 and the second elongated member 224. According to aspects of the invention, distraction mechanism 226 is adapted to vary the separation 238 between the first elongated member 222 and the second elongated member 224. The actuator 228, for example, a manual actuator, is operatively connected to the distraction mechanism 226, for example, by rods and linkages as discussed below, and is adapted to manipulate the distraction mechanism 226 to vary the separation 238 between the elongated members 222 and 224.

Figure 51:
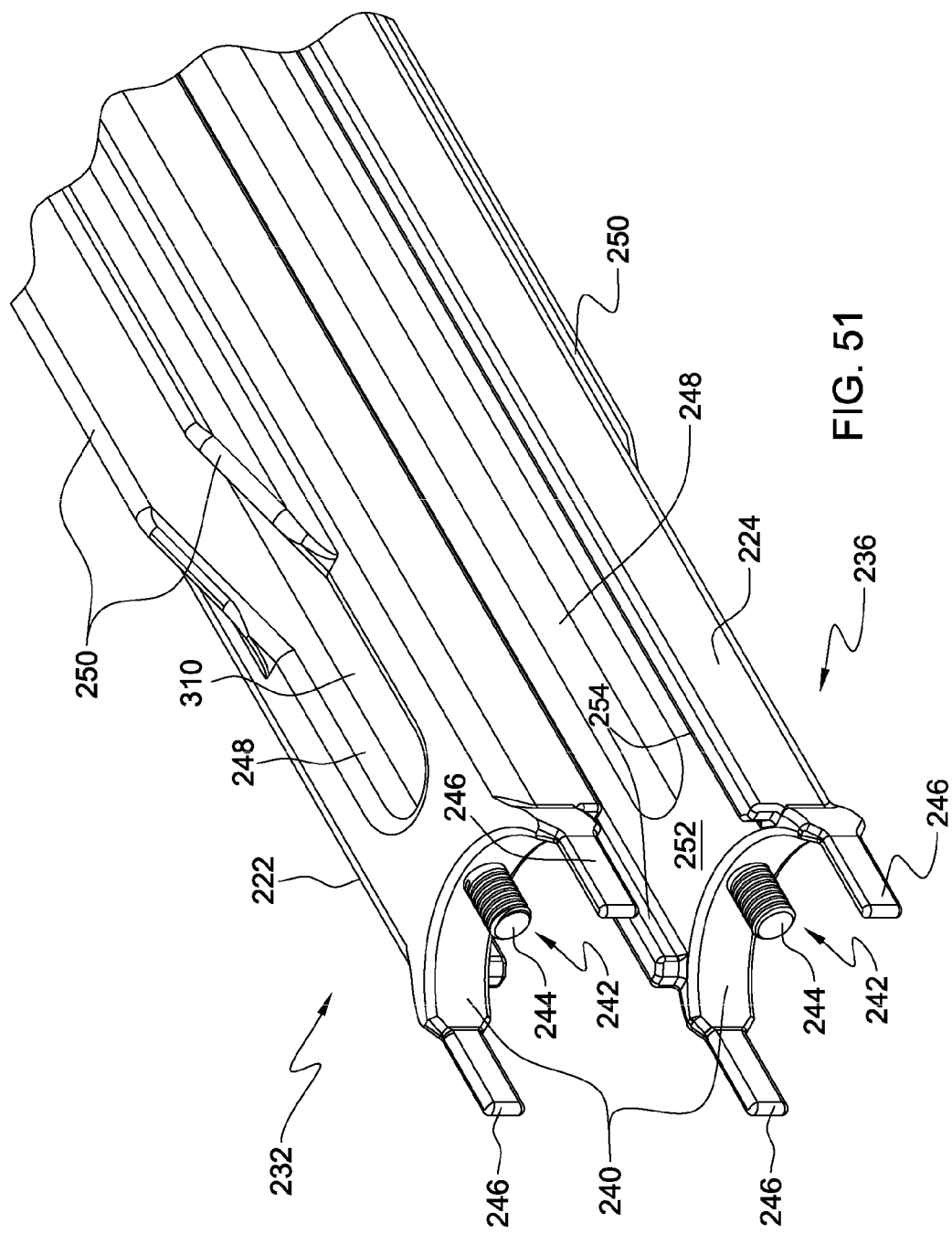
FIG. 51 is a detailed perspective view of the proximal end of the distraction tool shown in FIG. 48.

FIG. 51 is a detailed perspective view of the proximal ends 232, 236, of first elongated member 222 and second elongated member 224, respectively, of the distraction tool 220 shown in FIGS. 48-50. As noted above, proximal ends 232, 236 are adapted to receive components of an implant (not shown), for example, end members 212 and 214 shown in FIGS. 46 and 47. As shown in FIG. 51, proximal ends 232 and 236 may be appropriately shaped to receive the implant components (not shown), for example, proximal ends 232, 236 may include a recess 240 shaped to comply with the shape of the implant. In the aspect shown in FIG. 51, recesses 240 are arcuate and comprise a surface of substantially uniform radius; however, in other aspects, recesses 240 may be planar, for example, rectangular, or curved, for example, oval of ellipsoidal, to comply with implants of similar shape. Proximal ends 232 and 236 may also include a coupling device 242 adapted to enhance engagement of proximal ends 232 with the implant. For example, as shown in FIG. 51, proximal ends 232 and 236 may include a recess or projection 244, for example, a threaded screw positioned and sized to engage a threaded hole in the implant. In addition, proximal ends 232 and 236 may also include one or more axial projections or capture arms 246 adapted to engage one or more recesses in the implant. Projections 246 may be configured to facilitate capturing and holding of the implant during the distraction and implantation phases of the surgical procedure. In one aspect, projections 246 are configured and dimensioned to not exceed the outer dimensions of the implant so as to minimize the necessary surgical exposure and resultant tissue impingement of the instrument following insertion during the surgical procedure.

Coupling device 242 may also include spring locks, spring pins, and surface texturing, among other means of enhancing engagement with the implant.

As also shown in FIG. 51, elongated members 222 and 224 may include through holes or slots 248, for example, to minimize the weight of tool 220, and may include ribs 250, for example, tapered ribs, to strengthen elongated members 222 and 224 to minimize deflection or damage during use or handling.

In one aspect of the invention, elongated members 222 and 224 may be adapted to facilitate the insertion of a component of the implant (not shown), for example, an alignment mechanism to facilitate the insertion of intermediate spacer member 216 shown in FIGS. 46 and 47. For example, elongated members 222 and 224 may include a guide, for example, one or more channels, rails, ramps, pins, posts, keys, slots, guides and/or other alignment mechanisms, for inserting an intermediate spacer member 216 between the end member 222 and end member 224, for example, to facilitate insertion of an implant component. In the aspect of the invention shown in FIG. 51, each of the elongated members 222 and 224 includes a channel 252, for example, on the upper surface of lower elongated member 224 and on the lower surface of upper elongated member 222 to guide a component, for example, an intermediate spacer member, along elongated members 222 and 224 and assist the surgeon during insertion of, for example, an intermediate spacer member of an implant. Channels 252 have opposing sides or ribs 254 laterally spaced to guide the component along channels 252.

In one aspect, the alignment mechanism, such as, channel 252, may also function to confirm the correct sizing of the distracted gap or separation 238 that the instrument 220 has created. That is, the intermediate spacer member 216 may mate with both of the top and bottom alignment mechanism, for example, channels 252 or dovetails, and by doing so confirm that the top elongated member 222 and the bottom elongated member 224 are correctly spaced apart.

Figure 52:
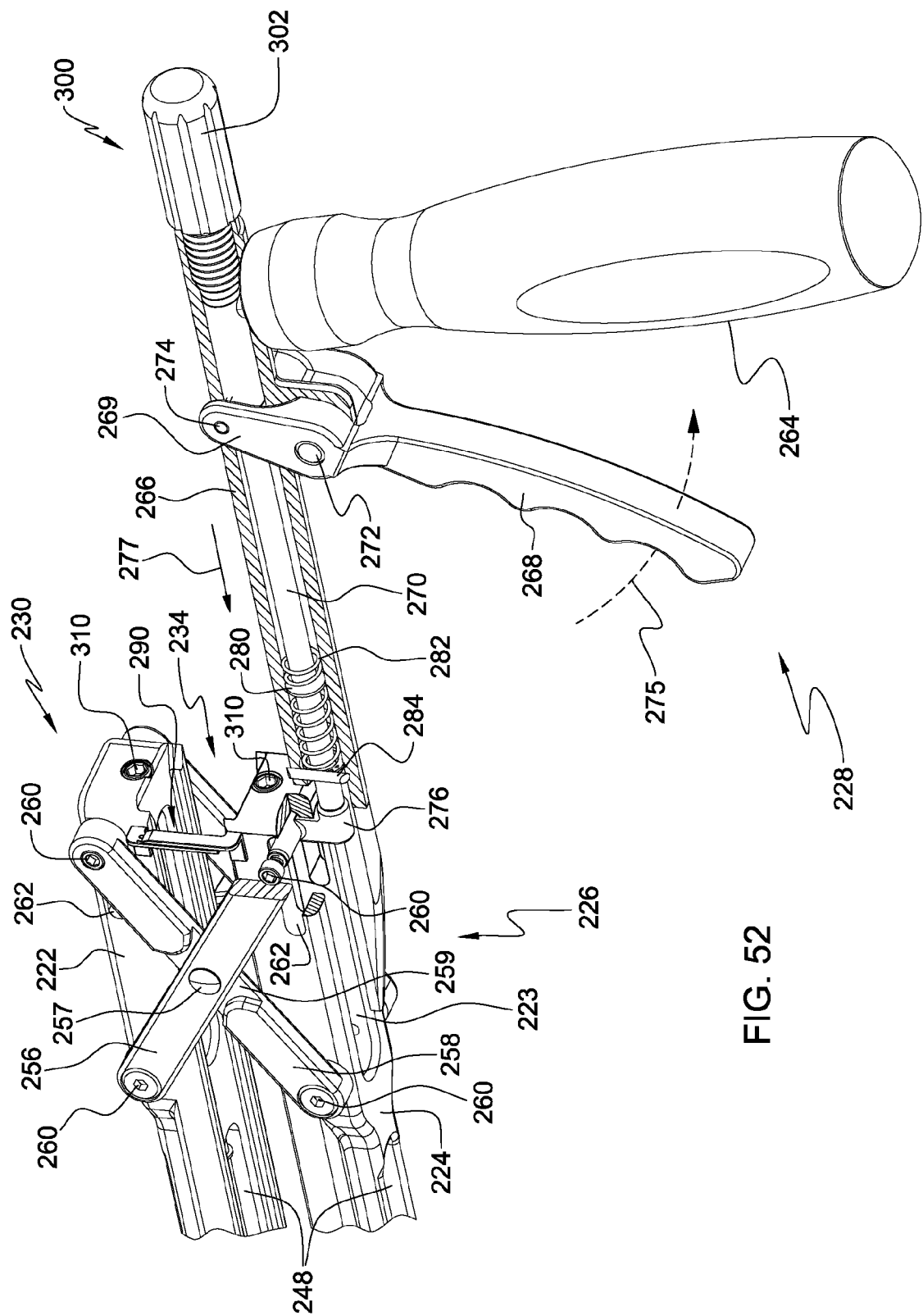
FIG. 52 is a detailed perspective view, partially in cross section, of the distal end of distraction mechanism of the distraction tool shown in FIG. 48.

FIG. 52 is a detailed perspective view, partially in cross section, of the distraction mechanism 226 of the distraction tool 220 shown in FIG. 48 according to one aspect of the invention. According to aspects of the invention, distraction mechanism 226 is configured to allow a surgeon or other operator to manipulate or vary the separation 238 (see FIGS. 48 and 49) between elongated members 222 and 224, and, accordingly, "distact" the two tissue surfaces against which the implant components mounted to the proximal ends 232, 236 of elongated members 222, 224, respectively, bear. In one aspect of the invention, any appropriate distraction mechanism 226 may be used to provide this function, for example, any combination of levers, cams, gears, or other devices or mechanisms that can effect the desired distraction may be used. In the aspect of the invention shown in FIG. 52, distraction mechanism 226 comprises at least one pair of links 256, 258 pivotally mounted to the distal ends 230, 234 of elongated members 222 and 224, respectively. Though one or more sets of links 256, 258 may be used to provide the desired function, as shown in FIG. 52, two sets of links 256, 258 pivotally mounted to opposite sides of elongated members 222 and 224 by fasteners or pins 260 are provided in the aspect shown in FIG. 52. Links 256, 258 may be pivotally mounted to each other by fastener 257, for example, a rivet or pin, and may include at least one recess 259 to minimize the assembled width of links 256, 258 and may limit the rotation of links 256, 258 about pin 257.

According to the aspect of the invention shown in FIG. 52, links 256, 258 may also be slidably mounted to elongated members 222 and 224. For example, the distal ends 230 and 234 of elongated members 222 and 224, respectively, may include elongated slots 262 positioned and adapted to receive pins 260 and allow longitudinal translation of pins 260 and links 256, 258 along elongated members 222 and 224.

According to aspects of the invention, distraction mechanism 226 is actuated by actuator 228. Again, though any type of manual or automated actuator may be used to actuate distraction mechanism 226, in the aspect of the invention shown in FIG. 52, actuator 228 may include a stationary hand grip 264 mounted to a support member 266, for example, a bar, rod or tube, and a rotatable hand lever 268 pivotally mounted to support member 266 and also pivotally mounted to an actuation rod or tube 270. Hand grip 264 may be shaped and made from a material to enhance the grip of the surgeon while providing a comfortable, ergonomic design. Hand grip 264 may have at least an elastomeric surface to enhance the grip, for example, a silicone based elastomer may be used. As shown in FIG. 52, hand lever 268 may have a forked extension 269 which is pivotally mounted to support member 266 by pin 272 and pivotally mounted to an actuator rod 270, for example, an actuator rod 270 mounted for axial translation within support member 266, for example, inside a hollow tube. As shown by the partial cut-away in FIG. 52, actuator rod 270 is operatively connected to an actuator bar 276 which in turn is connected to pin 260 of link 256. As shown in FIG. 52, in one aspect, the distal ends 230, 234 of elongated members 222, 224, respectively, may include elongated slots 223, for example, to allow unencumbered translation of actuator bar 276 within slots 223.

According to the aspect of the invention shown in FIG. 52, with the rotation of hand lever 268 about pin 272, for example, in the direction of arrow 275, the moment arm between pin 272 and pin 274 induces a translation of actuator rod 270, for example, in the direction of arrow 277, and a translation of actuator bar 276 and pin 260 in slots 262. The translation of pin 260 in opposing slots 262 translates the lower end of link 256 and, due to the pivotal mounting of link 256 to link 258 by pin 257 and the pivotal mounting of links 256 and 258 to elongated members 222 and 224 by pins 260, results in an increase in the distance 238 between elongated members 222 and 224. Similarly, the rotation of hand lever 268 about pin 272 in the direction of opposite to the direction of arrow 275 results in a decrease in the distance 238 between elongated members 222 and 224.

FIG. 52 also illustrates certain features of the present invention that enhance operation or facilitate use of the invention by the surgeon. For example, the translation of actuator rod 270 may be biased by the presence of one or more springs 280, that is, actuator 228 may be a spring-based manual actuator. In one aspect, the one or more springs 280 are operatively connected to the actuation rod 270. The one or more springs 280 may be restrained on rod 270 by snap ring 282 and may bear against pins 284 mounted to support member 266.

According to another aspect of the invention, an indicator adapted to indicate the spacing 238 between elongated members 222 and 224 may be provided to the surgeon, for example, by one or more user-readable indicia. The indicator of the spacing 238 may be provided by a moving indicator, for example, a translating indicator or a rotating indicator. For instance, in one aspect, elongated members 222 and 224 may be provided with a scale 290 having at least one translatable element that indicates the spacing 238 with movement of elongated members 222 and 224. An example of one such scale is shown in FIG. 53.

Figure 53:
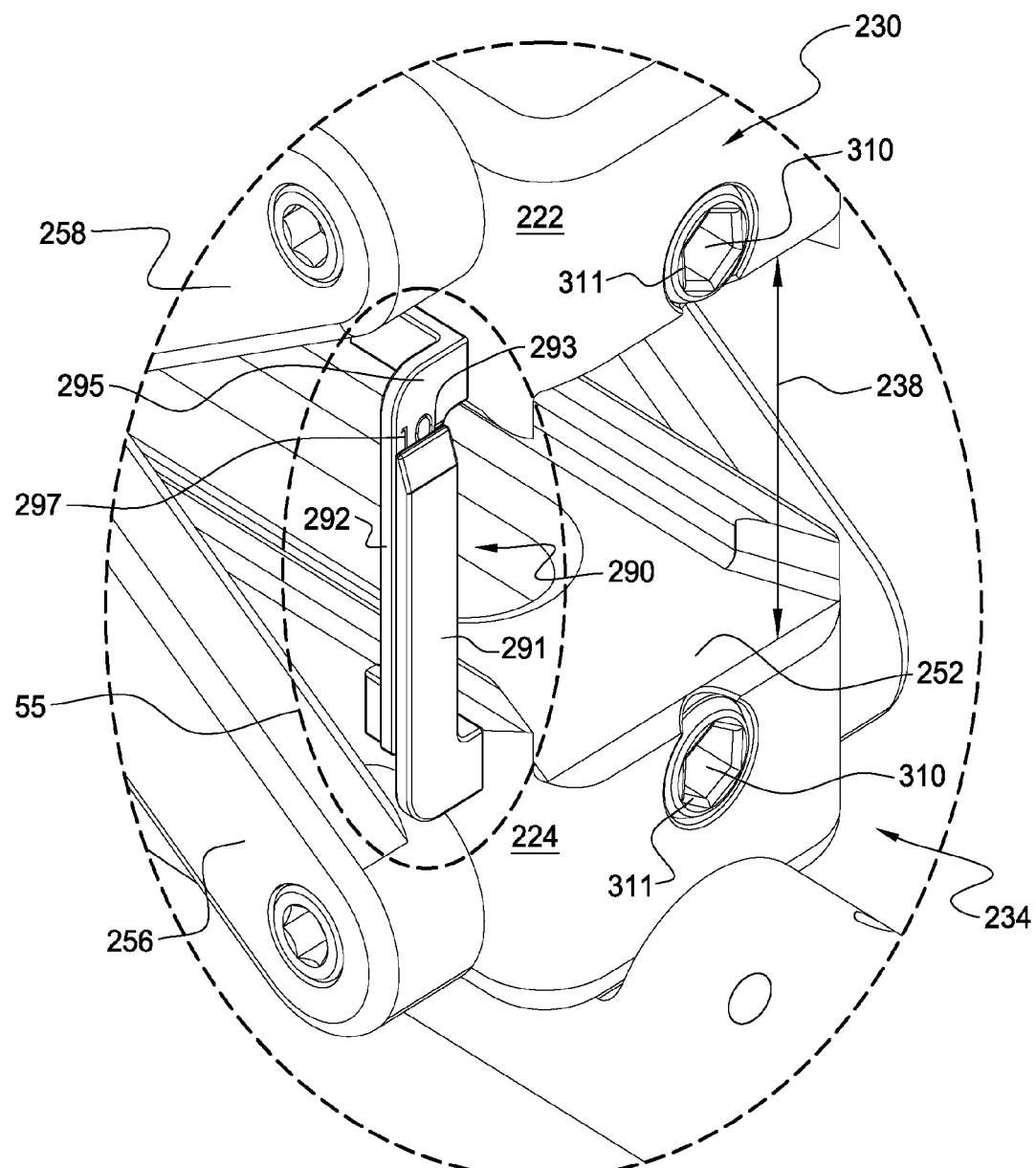
FIG. 53 is a detailed perspective view of the distal end of the distraction tool identified by Detail 53 in FIG. 46.
Figure 55:
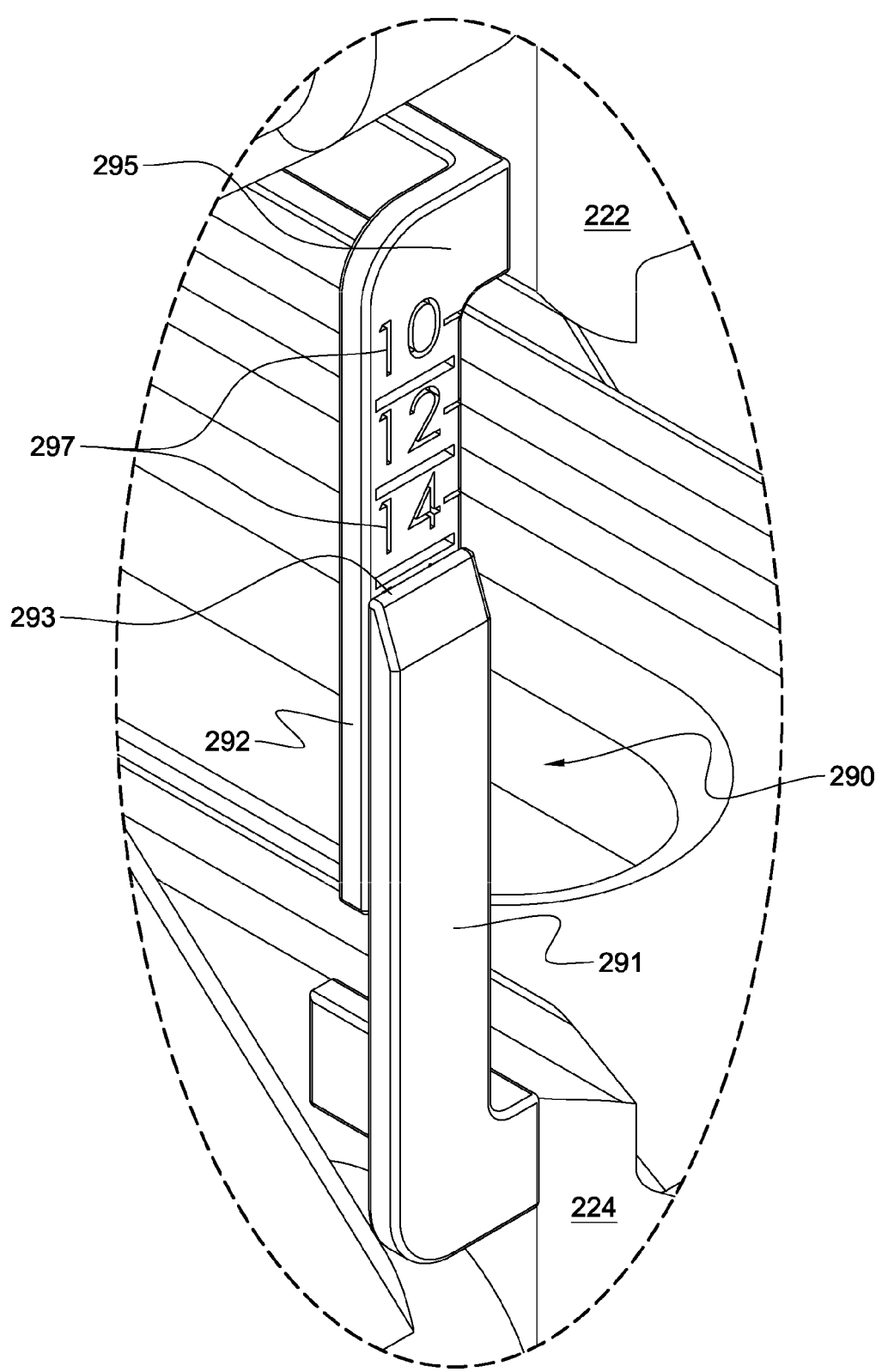
FIG. 55 is a detailed perspective view of the distraction tool shown in FIG. 53 identified by Detail 55 in FIG. 53.

FIG. 53 is a detailed perspective view of the distal ends 230, 234 of the distraction tool 220 identified by Detail 53 in FIG. 46. FIG. 53 illustrates one indicator 290 that may be used to indicate the separation 238 according to an aspect of the invention. As shown, indicator 290 may include indicator member 291 mounted to lower elongated member 224 and indicator member 292 mounted to upper elongated member 222. As illustrated in FIG. 53, with distraction or contraction of tool 220 and the variation in separation 238, the edge 293 of member 291 translates with respect to member 292. According to this aspect of the invention, face 295 of member 292 includes indicia 297, for example, lines and dimension numbers, corresponding to separation 238. In one aspect, the edge 293 provides an indication of the separation 238, for example, the indicia immediately above edge 293 may indicate the separation 238. In one aspect the indicia 297 may include 1 mm increments of separation 238, though other units and intervals may be used. FIG. 55 illustrates the operation of indicator 290 when the separation 238 is increased from that shown in FIG. 53. FIG. 55 is a detailed perspective view of the distraction tool 220 shown in FIG. 53 identified by Detail 55 in FIG. 53.

Insertion tool 220 may also include means for locking the relative positions of elongated members 222 and 224, for example, to maintain a desired distraction distance 238. In one aspect of the invention, as shown in FIG. 52, actuation mechanism 228 may include a locking mechanism 300, for example, an internally threaded and externally fluted or knurled locking collar or knob 302 that when activated mechanically restricts the movement of actuator rod 270, and substantially prevents the movement of actuator rod 270, actuator bar 276 and links 256 and 258 to "lock" the position of elongated members 222 and 224 to maintain the separation 238. Other locking mechanisms may also be provided within the scope of this invention. In addition, the knob or collar 302 may be provided with an indicator that cooperates with human readable indicia on the outer surface of support member 266 to indicate the separation 238.

Figure 54:
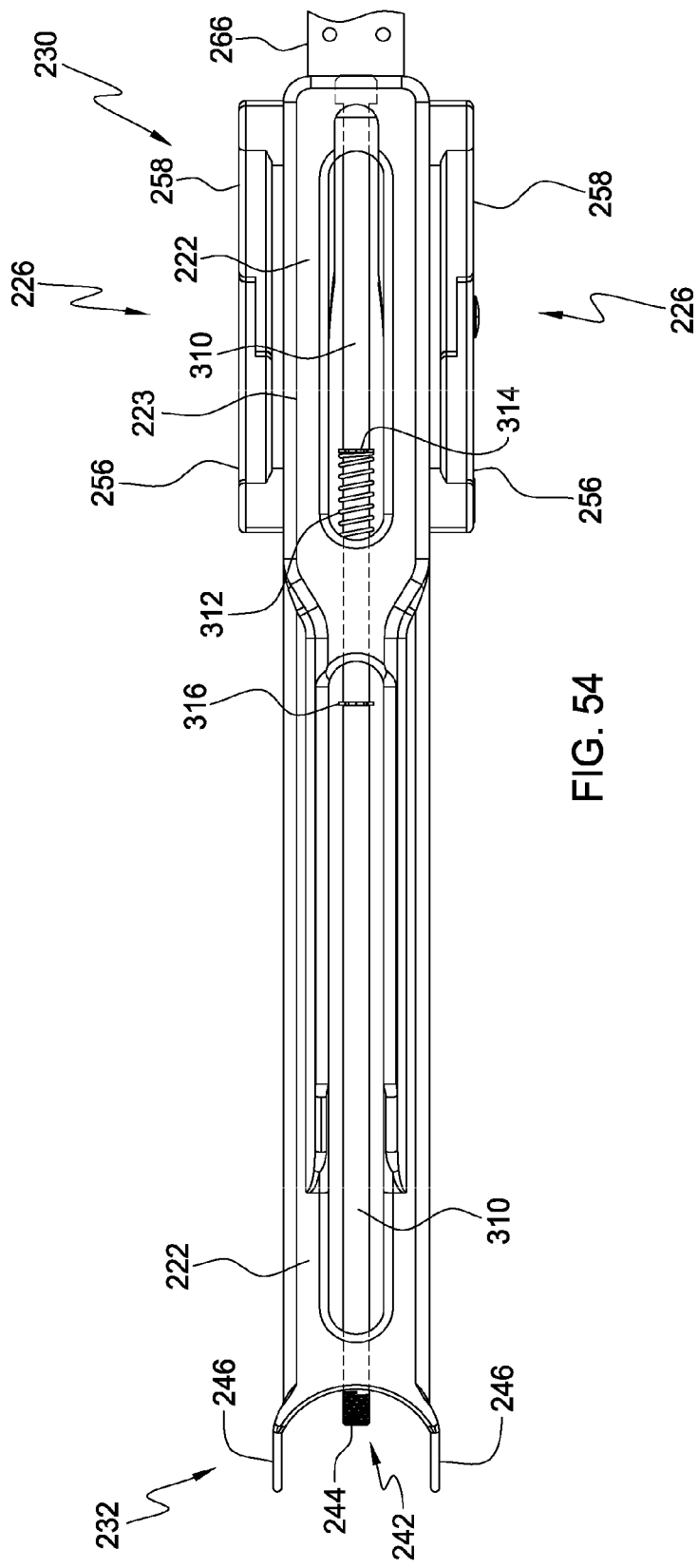
FIG. 54 is a detailed top view of the distraction tool shown in FIG. 50 identified by Detail 54 in FIG. 50.

In another aspect of the invention, as shown in FIG. 54, the coupling device 242 on the proximal ends 232, 236 of elongated members 222 and 224, respectively, may be actuated remotely, for example, by means of one or more elongated rods 310, from proximal ends 232, 236, for instance, actuated from distal ends 230, 236. Rods 310 may be accessible from the distal end 230 and 234 of elongated members 222 and 224. As shown in FIG. 53, the ends of rods 310 may be recessed into the ends of members 222 and 224 and have a recess 311 engageable by a tool, for example, a hex head wrench. In one aspect, the end of rod 310 may be provided with a knob or handle to facilitate rotation of rod 310 by the surgeon. This aspect of the invention is most clearly illustrated in FIG. 54 which shows a detailed view of the top view of the invention shown in FIG. 50 as indicated by detail 54 in FIG. 50. As shown in FIG. 54, rods 310 may extend from distal ends 230 and 234 to proximal ends 232 and 236, respectively, and engage coupling device 242, for example, end in threaded projection 244. In one aspect, threaded projection 244 comprises a threaded end of rods 310. As shown in FIG. 54, rods 310 may pass through elongated members 222 and 224, for example, pass through one or more through holes in elongated members 222 and 224. As shown, in one aspect, rod 310 may pass through at least one of elongated member 222 and elongated member 224 substantially parallel to the axis of the respective elongated member 222, 224. At least one of, typically both, of rods 310 may be biased by an elastic member 312, for example, a spring or elastic bushing, that is, rods 310 may be spring-biased threaded rods. The elastic member or spring 312 may be retained on rod 310 by appropriate hardware, for example, one or more spring clips 314. The travel of rod 310 may also be limited by a step or obstruction on rod 310, such as, a spring clip 316.

According to aspects of the invention, the coupling mechanism 242, for example, a threaded projection 244, on the proximal ends 232, 236 of elongated members 222 and 224, respectively, can be actuated, for example, rotated, by rotating the distal end of rods 310, for example, accessible from the distal ends 230 and 234 of elongated members 222 and 224, respectively. Accordingly, in aspects of the invention, components of implants being inserted using tool 220 can be engaged and disengaged by the coupling mechanism, for example, threaded and unthreaded, by remotely rotating rods 310, that is, remotely from proximal ends 232 and 236, for instance, from distal ends 230, 234.

Figure 56:
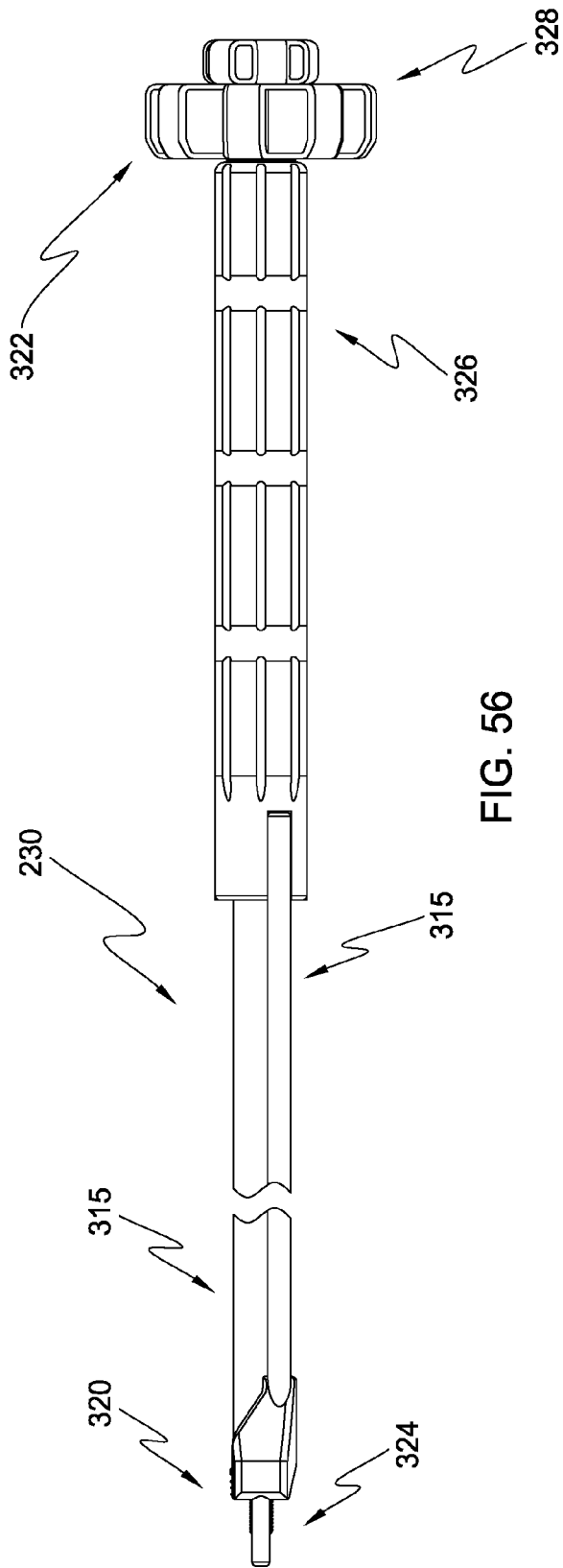
FIG. 56 is a side elevation view of the insertion tool shown in FIGS. 46 and 47 according to one aspect of the invention.

FIG. 56 is a side elevation view of the insertion tool 230 shown in FIGS. 46 and 47 according to one aspect of the invention. Insertion tool 230 may be adapted to insert an intermediate spacer member between end members of an implant, for example, between end members 212 and 214. As shown in FIGS. 46 and 47, according to aspects of the invention, insertion tool 230 may be used in conjunction with distraction tool 220 to implant a tissue spacer, for example, tissue spacer implant 10 and/or 110 described above. Once the surgeon establishes a desired distraction or separation 238 between implant components, for example, end members 212 and 214 shown above, the surgeon may then insert an intermediate component of the implant, for example, intermediate spacer member 120 or 216 disclosed above, using insertion tool 230.

As shown in FIG. 56, insertion tool 230 may have a proximal end 320 and a distal end 322 and may comprise one or more elongated members 315. Proximal end 320 includes a coupling device 324 adapted to mount to an implant component, for example, an intermediate spacer member 216. Distal end 322 includes a handle assembly 326 and a coupling mechanism actuator 328.

Figure 57:
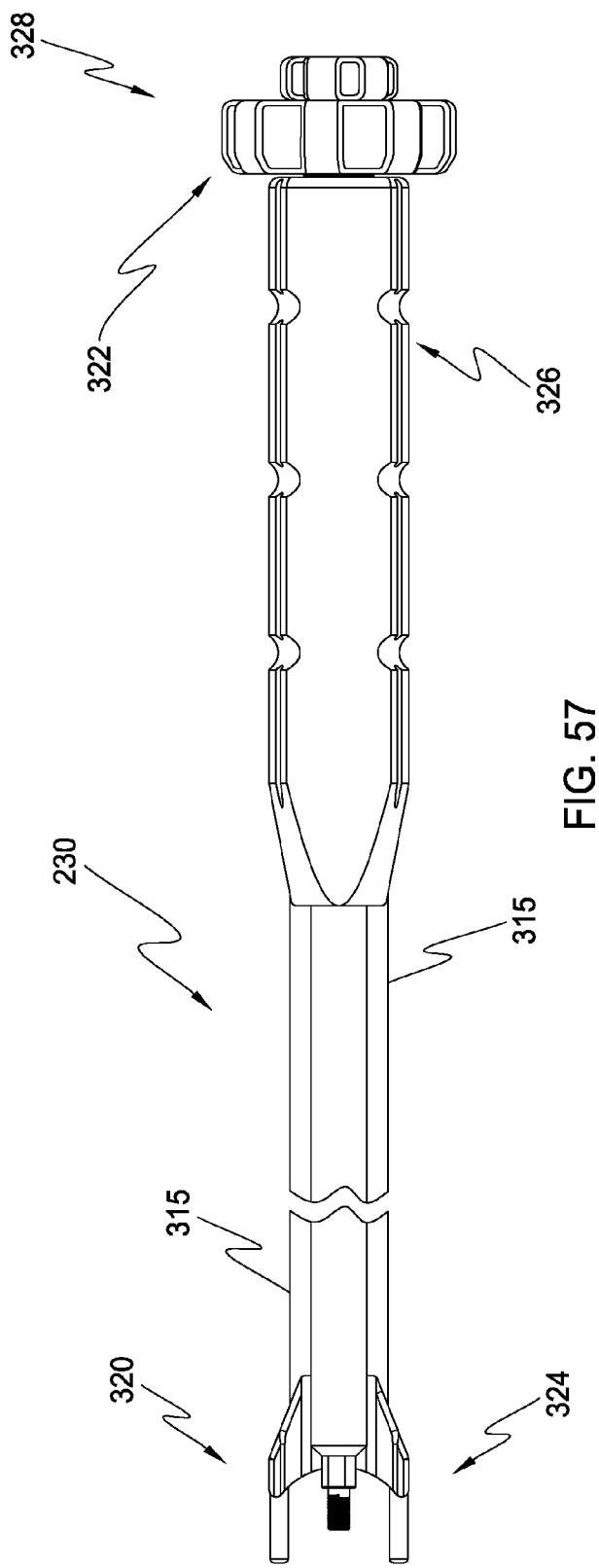
FIG. 57 is a top view of the insertion tool shown in FIG. 56.
Figure 58:
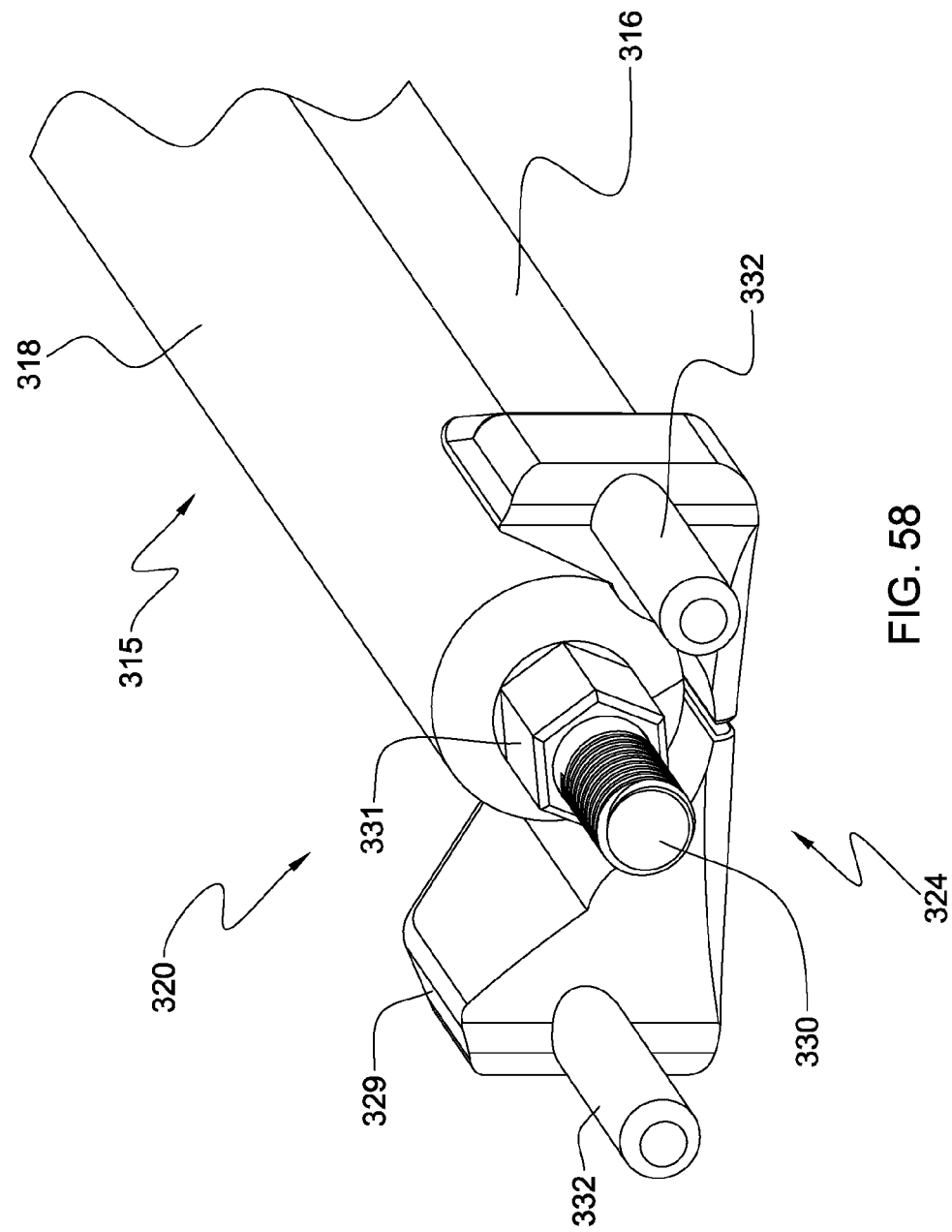
FIG. 58 is a perspective view of the proximal end of the insertion tool shown in FIG. 56.
Figure 59:
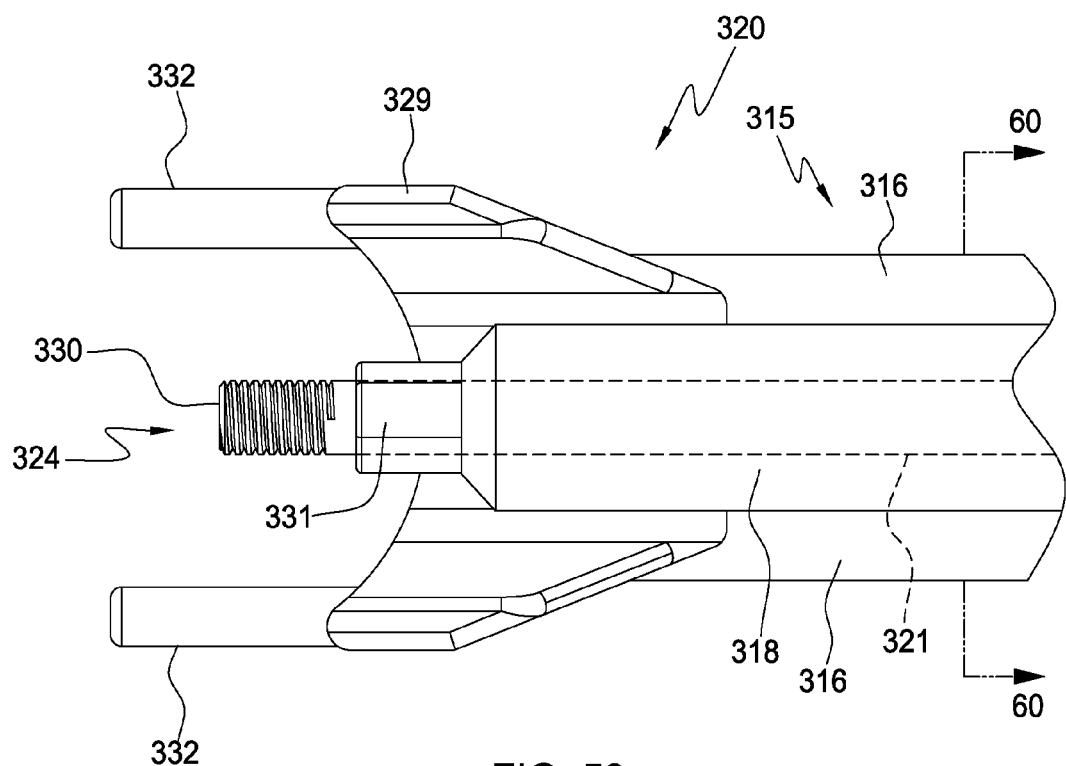
FIG. 59 is a top view of the proximal end of the insertion tool shown in FIG. 56.
Figure 60:
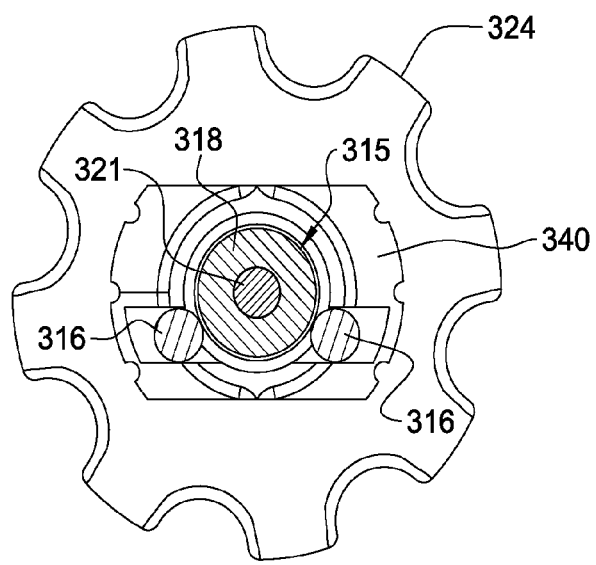
FIG. 60 is a cross sectional view of the insertion tool shown in FIG. 59 as viewed along section lines 60-60 in FIG. 59.

FIG. 57 is a top view of the proximal end 320 of the insertion tool 230 shown in FIG. 57. FIG. 58 is a perspective view of the proximal end 320 of the insertion tool 230 shown in FIGS. 56 and 57 and FIG. 59 is a top view of the proximal end 320 shown in FIG. 58. As shown in FIGS. 57 and 58, in one aspect, the one or more elongated members 315 may comprise three elongated members: two side members 316 and one central member 318. FIG. 60 is a cross sectional view of the one or more members 315 as viewed along section lines 60-60 in FIG. 59. Though members 316 and 318 may have any shape cross section, as shown in FIG. 59, in this aspect, members 316 and 318 may be circular in cross section. As shown in FIGS. 58-60, coupling device 324 of proximal end 320 may include a coupling bracket 329 mounted to one or more of elongated members 316, 318. Coupling bracket 329 may include one or more projections or pins 332 adapted to be received by or engage an implant component (not shown). As also shown in FIGS. 58-60, coupling device 324 may also include a projection 330 adapted to engage an implant component, for example, a threaded rod positioned and sized to be received by a threaded hole of an implant component, such as, a threaded hole in intermediate member 120 described above. As also shown, proximal end 320 may also include a projection 331 adapted to engage a fastener, for example, a hex head drive.

According to an aspect of the invention, projection 330, for example, a threaded rod, may be adapted to be rotated by a rod 321 extending along or within the one or more elongated members 315, and projection 331, for example, the hex head drive, may be adapted to be rotated by a rod 318 extending along or within the one or more elongated members 315. For example, as shown in FIG. 59, elongated rod 318 may extend along elongated rods 316 to hex head drive 331 and elongated rod 321 may extend through rod 318 and engage coupling device 324, for instance, threaded projection 330. In one aspect, threaded projection 330 may comprise a threaded end of rod 321. According to aspects of the invention, the coupling of proximal end 320 to an implant component may be controlled remotely by rotating rod 321 and threaded end 330 from the distal end of insertion tool 230. According to other aspects of the invention, the implant component (not shown) may be manipulated, for example, a coupling mechanism may be activated, by rotating rod 318 having hex head drive 331. This aspect of the invention will be made clearer in the following discussion.

Figure 61:
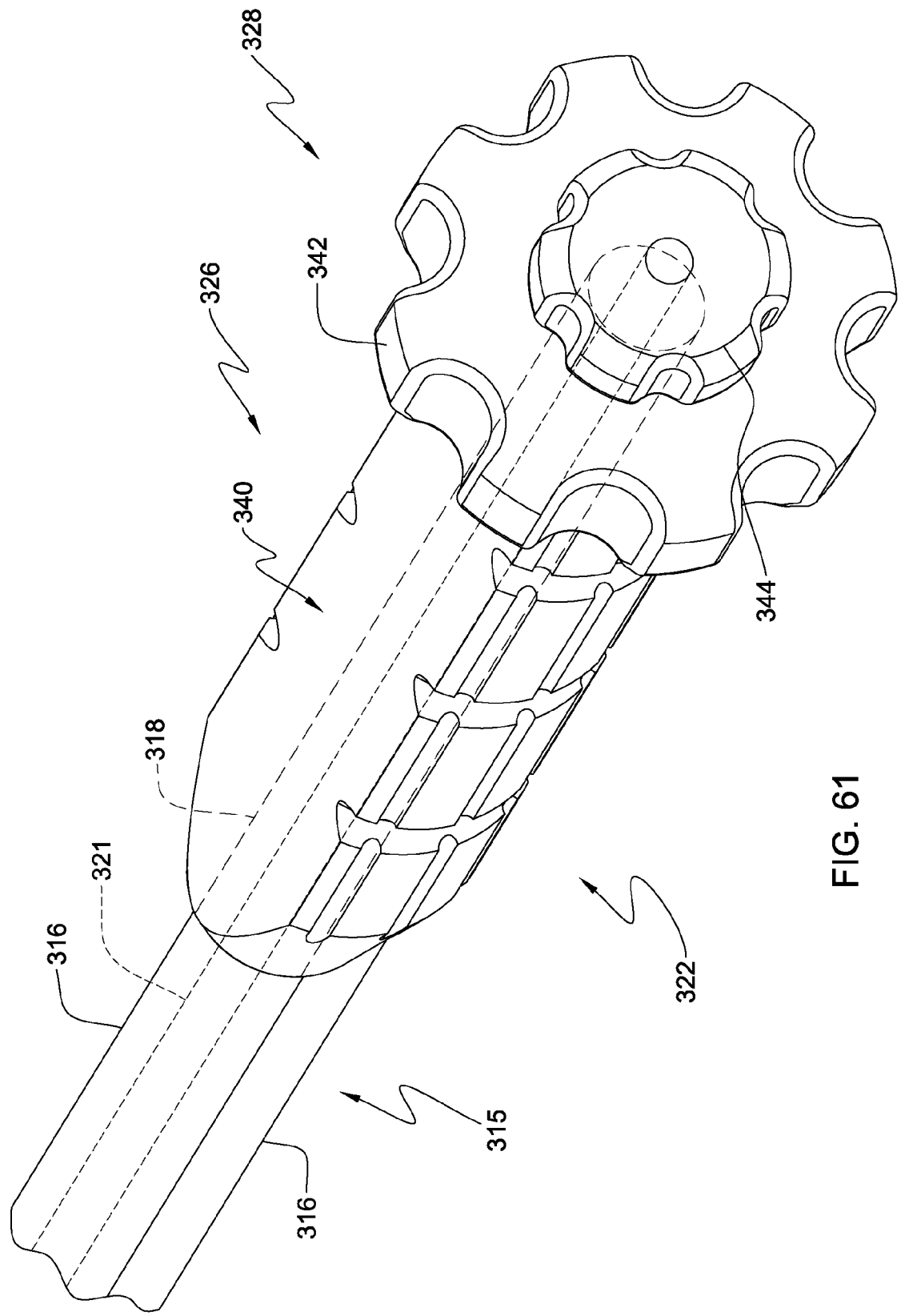
FIG. 61 is a perspective view of the distal end of the insertion tool shown in FIG. 56.

FIG. 61 is perspective view of distal end 322 of insertion tool 230 shown in FIGS. 46 and 47. As shown distal end 322 includes a handle assembly 326 mounted to elongated member 315 and a coupling mechanism actuator 328 mounted to handle assembly 326. Handle assembly 326 typically includes a handle 340, knob 342, and knob 344 mounted to handle 340. Handle 340 is adapted to facilitate gripping and manipulation of inserted tool 230, for example, having flutes or knurls and is mounted to elongated member 315, for example, molded on elongated members 316. Actuator mechanism 328 is adapted to actuate coupling device 324 at the proximal end of insertion tool 230. For example, in the aspect shown, actuator mechanism 328 may comprise a knob or handle 342 mounted to rod 318 whereby rotation of knob 342 rotates rod 318 and hex drive 331. In another aspect, actuator mechanism 328 may also comprise a knob or handle 344 mounted to rod 321 whereby rotation of knob 344 rotates rod 321 and also rotates threaded projection 330 providing for engagement or disengagement of insertion tool 230 with an implant component, for example, with intermediate spacer member 120, 216 described above. Knob 342 may be mounted to rod 318 and knob 344 may be mounted to rod 321 by conventional means, for example, rods 318 and 321 may be mounted to a bushing or insert (not shown), for example, by welding, and then the bushing or insert may be press fit into knobs 342 and 344, respectively. In one aspect, the bushings may be exposed and provide a surface that can be struck to transmit a force to the implant mounted at the proximal end 320. As shown in FIG. 61, knob 342 and knob 344 may be adapted to facilitate handling, for example, having flutes or knurls as shown.

In one aspect, insertion tool 230 may include elongated rod 315 having a first end and a second end opposite the first end, wherein the first end comprises the handle 340 and the second end comprises a coupling device 324 adapted to receive an implant component, for example, an intermediate spacer member 120, 216. In another aspect, insertion device 230 includes an activation rod 318 operatively connected to the coupling device 324. Rod 318 may pass through handle 340 and terminate with a knob 342, for example, a rotatable knob that may be used to withdraw rod 318. Rod 321 may also pass through handle 340, for example, and also pass within rod 318, and terminate with a knob 344, for example, a rotatable knob that may be used to withdraw rod 321. In one aspect, knobs 342 and/or knob 344 may be lockable to handle 340, for example, knob 342 and/or knob 344 may be threaded to handle 340, for instance, knob 344 may be threaded into knob 342 whereby the threaded engagement retains or locks rod 318 and/or rod 321 to handle 340.

Distraction tool 220 and insertion tool 230 may be fabricated from metals and/or non-metals. For example, in one aspect, distraction tool 220 and insertion tool 230 may be metallic, for example, made from any metal that is resistant to corrosion when exposed to bodily fluids, such as, stainless steel or titanium. In another aspect, distraction tool 220 and insertion tool 230 may be non-metallic, for example, made from a plastic that is resistant to attack when exposed to bodily fluids, such as, a PEEK, a PTFE, or their equivalents. In one aspect, distraction tool 220 and insertion tool 230 may typically be made from FDA approved implant grade materials, such as, implant grade titanium and/or implant stainless steel or implant grade plastics, such as, PEEK.

Figure 62:
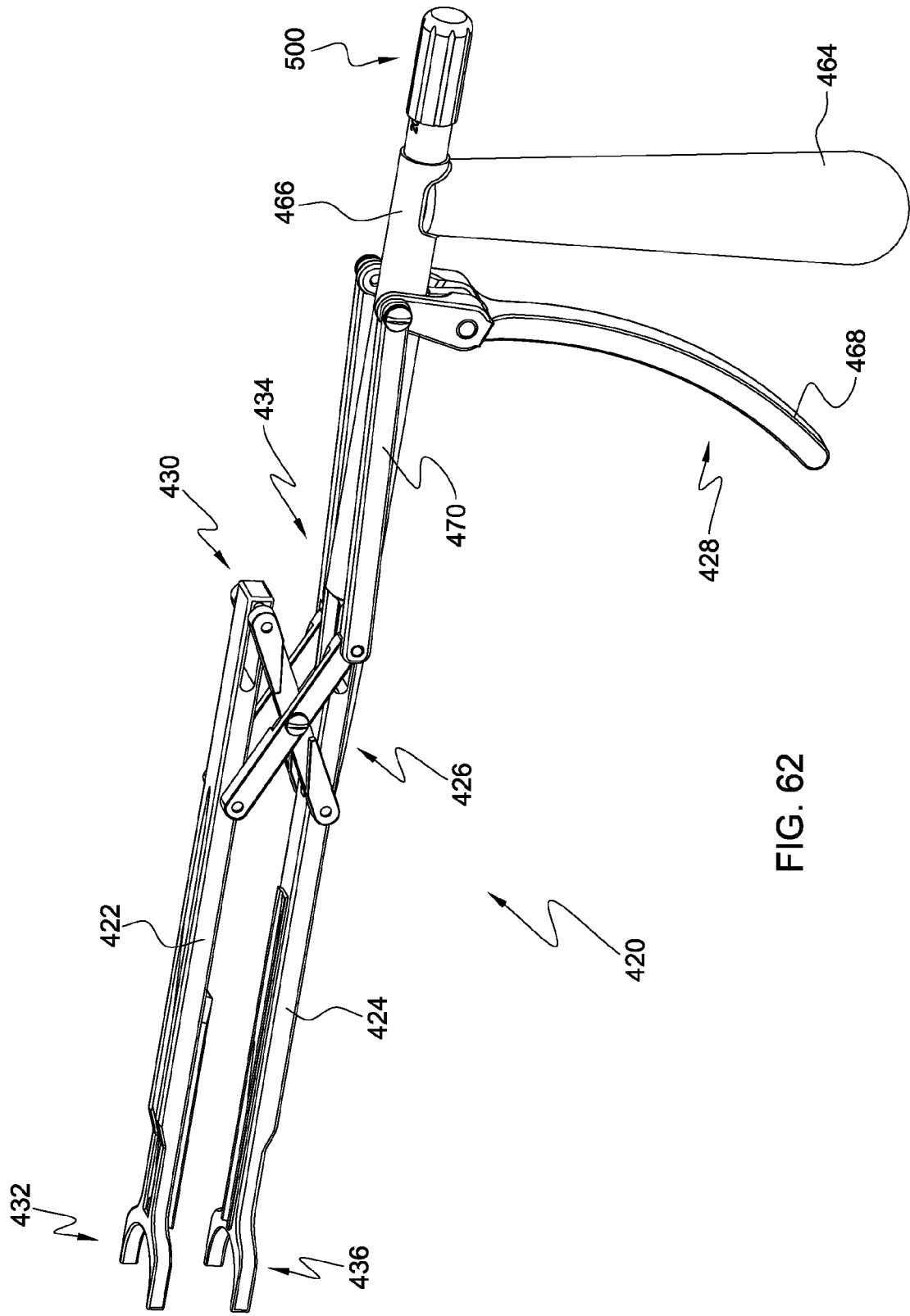
FIG. 62 is a perspective view of a surgical tool assembly according to another aspect of the invention which can be used to implant a tissue spacer implant.
Figure 63:
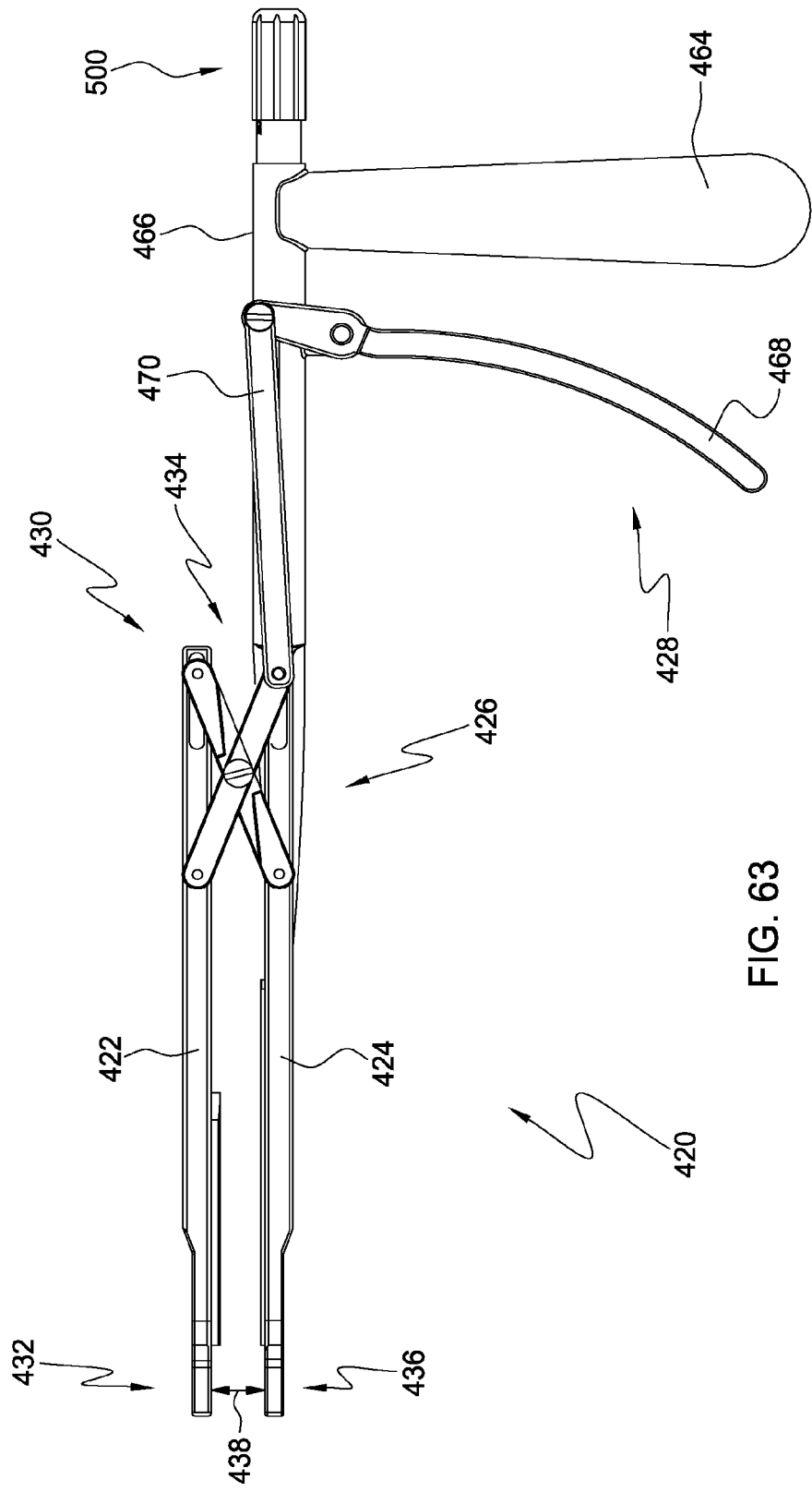
FIG. 63 is a side elevation view of the tool shown in FIG. 62.

FIG. 62 is a perspective view of a distraction tool 420 according to another aspect of the invention which can be used to implant a tissue spacer implant, for example, to insert tissue spacer implant 10 or 110 disclosed above. FIG. 63 is a side elevation view of the distraction tool 420 shown in FIG. 62. As shown, according to one aspect, distraction tool 420 is adapted to insert a first end member, for example, end member 112 shown in FIG. 26, a second end member, for example, end member 114 shown in FIG. 26, and a intermediate member, for example, intermediate spacer member 120 shown in FIG. 31 into a living being, for example, a live human patient.

Figure 64:
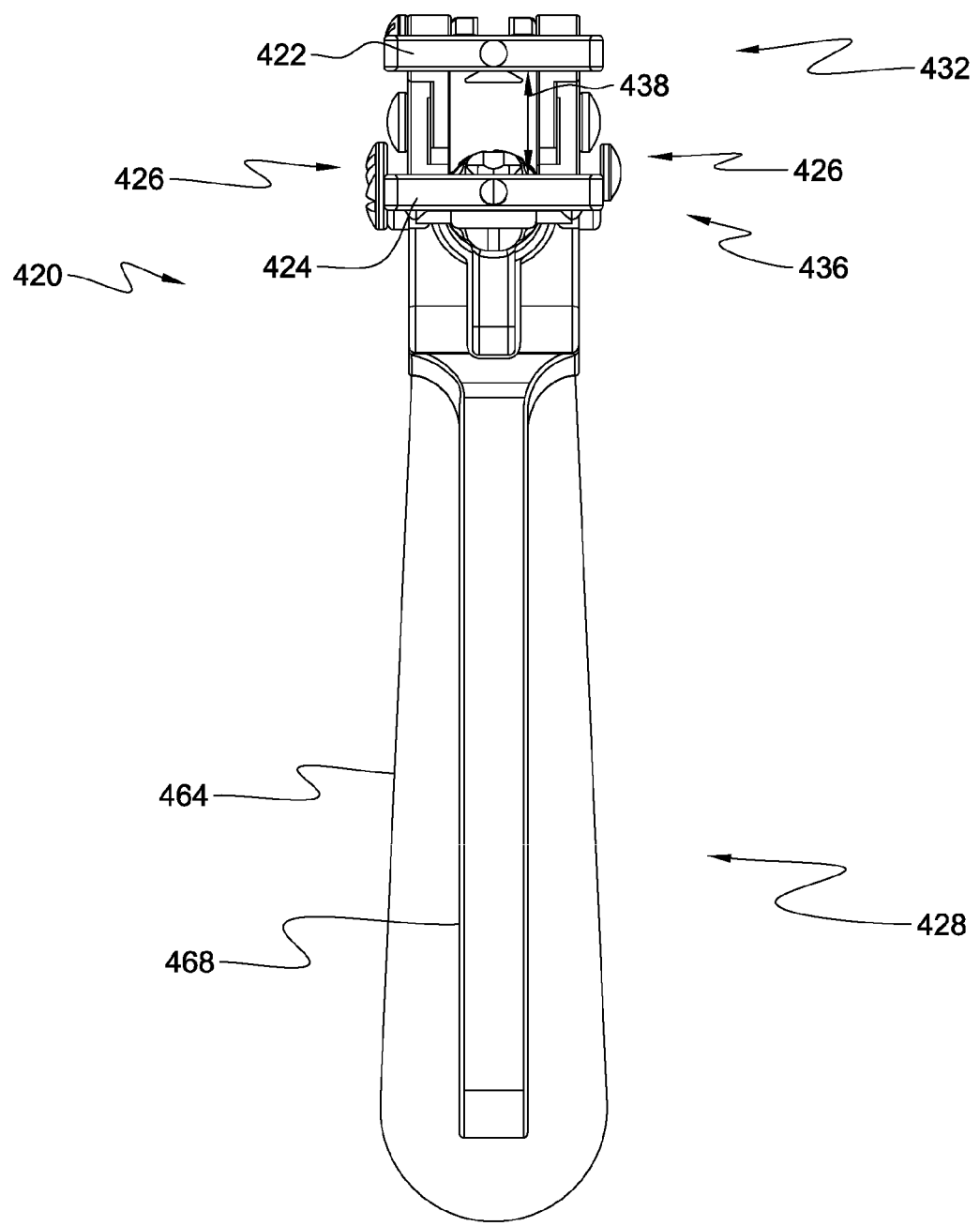
FIG. 64 is a left end elevation view of distraction tool shown in FIG. 62.
Figure 65:
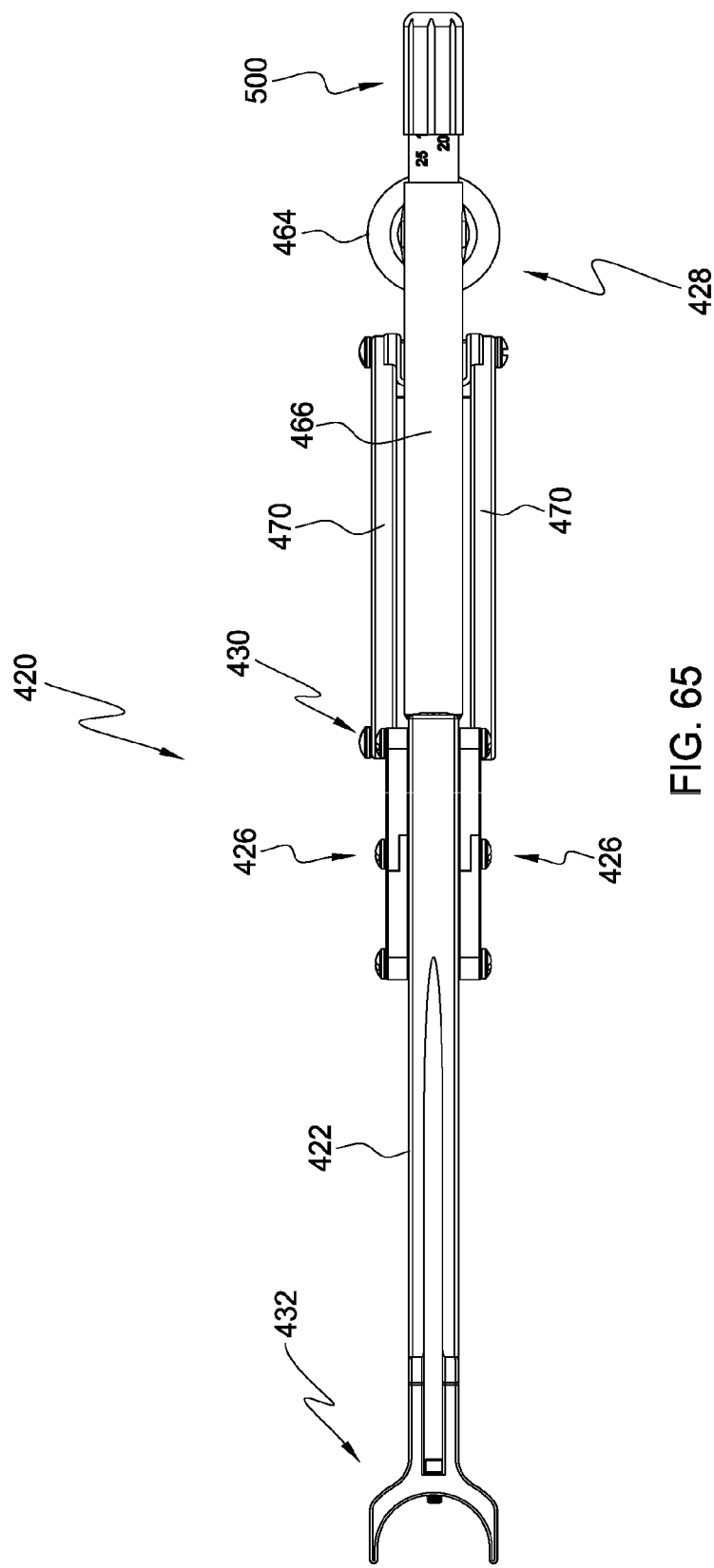
FIG. 65 is a top view of the distraction tool shown in FIG. 62.

FIG. 64 is a left end elevation view of the distraction tool 420 shown in FIG. 62, and FIG. 65 is top view of distraction tool 420 shown in FIG. 62. As shown in FIGS. 62-65, distraction tool 420 includes a first elongated member 422, a second elongated member 424, a distraction mechanism 426, and an actuator 428. First elongated member 422 includes a distal end 430 and a proximal end 432. Proximal end 432 is typically adapted to receive a first end member of an implant (not shown in, but see, for example, end member 112 shown in FIGS. 22 and 23). Second elongated member 424 similarly includes a distal end 434 and a proximal end 436. Proximal end 436 is typically adapted to receive a second end member of the implant (again, not shown, but see, for example, end member 114 shown in FIGS. 22 and 23). The distraction mechanism 426 is operatively connected to the first elongated member 422 and the second elongated member 424. According to aspects of the invention, distraction mechanism 426 is adapted to vary the separation 438 (see FIG. 64) between the first elongated member 422 and the second elongated member 424. The actuator 428, for example, a manual actuator, is operatively connected to the distraction mechanism 426, for example, by rods and linkages as discussed below, and is adapted to manipulate the distraction mechanism 426 to vary the separation 438 between the elongated members 422 and 424.

Figure 66:
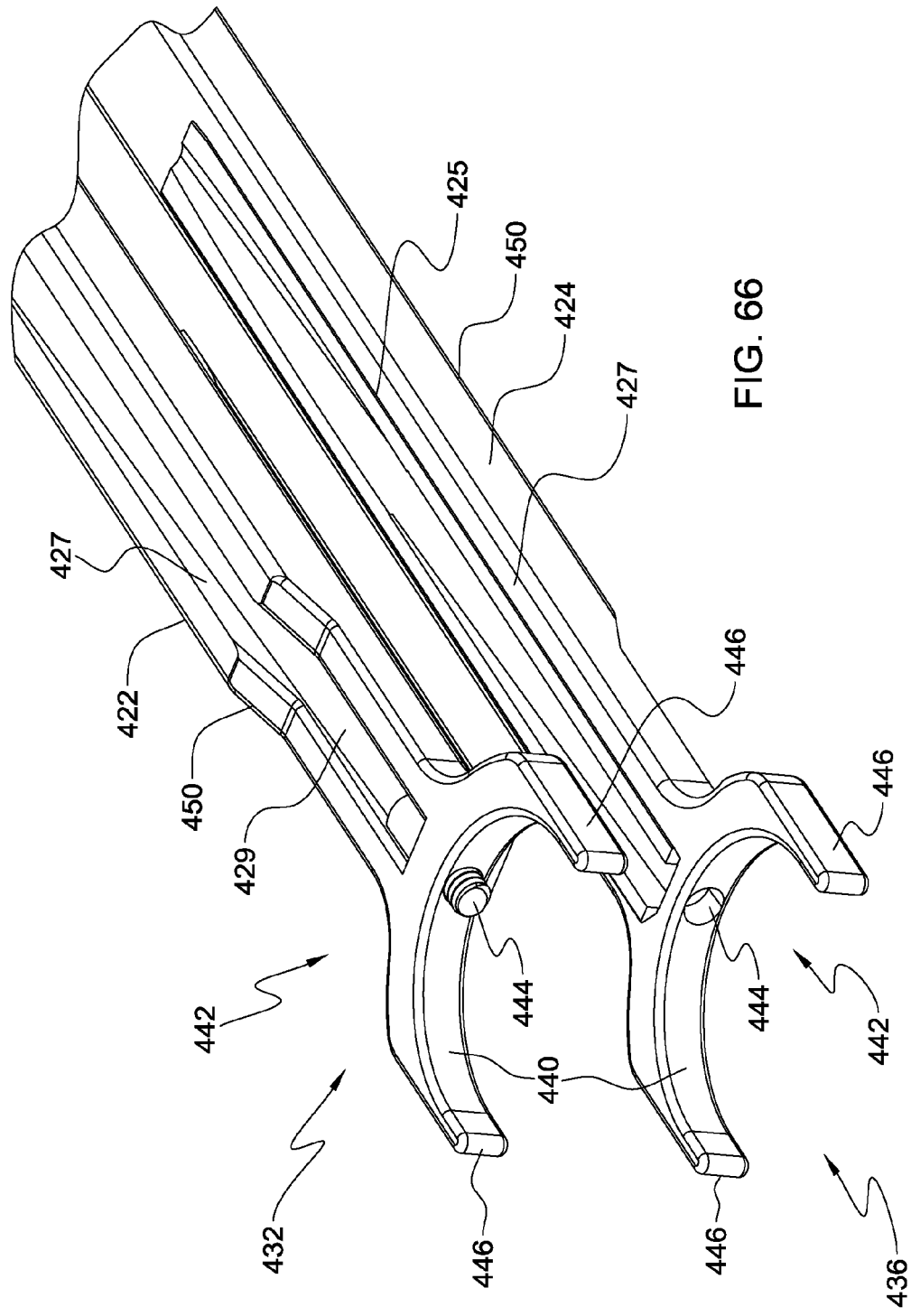
FIG. 66 is a detailed perspective view of the proximal end of the distraction tool shown in FIG. 62.

FIG. 66 is a detailed perspective view of the proximal ends 432, 436, of elongated members 422 and 424, respectively, of the distraction tool 420 shown in FIGS. 63-65. As noted above, proximal ends 432, 436 are adapted to receive components of an implant (not shown), for example, end members 112 and 114 shown in FIGS. 22 and 23. As shown in FIG. 66, proximal ends 432 and 436 may be appropriately shaped to receive the implant components (not shown), for example, proximal end 432 and 436 may each include a recess 440 shaped to comply with the shape of the implant. In the aspect shown in FIG. 66, recess 440 is arcuate and comprises a surface of substantially uniform radius; however, in other aspects, recess 440 may be planar, for example, rectangular, or curved, for example, oval of ellipsoidal, to comply with implants of similar shape. Proximal ends 432 and 436 may also include a coupling device 442 adapted to enhance engagement of proximal ends 432 with the implant. For example, as shown in FIG. 66, proximal ends 432 and 434 may include a recess, hole, or projection 444, for example, a threaded projection, positioned and sized to engage a threaded hole in the implant. In addition, proximal ends 432 and 434 may also include one or more axial projections or capture arms 446 adapted to engage one or more recesses in the implant. Projections 446 may be configured to facilitate capturing and holding of the implant during the distraction and implantation phases of the surgical procedure. In one aspect, projections 446 are configured and dimensioned to not exceed the outer dimensions of the implant so as to minimize the necessary surgical exposure and resultant tissue impingement of the instrument following insertion during the surgical procedure. Coupling device 442 may also include spring locks, spring pins, and surface texturing, among other means of enhancing engagement with the implant.

As also shown in FIG. 66, elongated members 422 and 424 may include through holes or slots 427, for example, to minimize the weight of tool 420, and may include ribs 450, for example, tapered ribs, to strengthen elongated members 422 and 424 to minimize deflection or damage during use or handling.

According to one aspect of the invention, slots 427 may be provided to provide access to projection or recess 444, for example, for access by a tool adapted to secure an implant component to distraction tool 420. For instance, as shown in FIG. 66 slots 427 in elongated members 422 and 424 may be provided to allow access to the one or more threaded rods 429 to secure an implant component to distraction tool 420. In one aspect, slots 427 may comprise angled channels or tapered slots, that is, slots of increasing depth or sloped in a distal to proximal direction to provide assistance to the surgeon in accessing hole 444 with rod 429, for example, a rod have a threaded end adapted to engage a hole with an internal thread on a component of the implant. In one aspect, threaded projection 444 may comprise the threaded end of rod 429.

In one aspect of the invention, elongated members 422 and 424 may be adapted to facilitate the insertion of a component of the implant (not shown), for example, having a guide or alignment mechanism for inserting an intermediate spacer member between the end member 422 and end member 424, for instance, to facilitate the insertion of intermediate spacer member 120 shown in FIGS. 22 and 23. For example, elongated members 422 and 424 may include one or more channels, rails, ramps, pins, posts, keys, slots, guides, and/or alignment mechanisms to facilitate insertion of an implant component. In the aspect of the invention, shown in FIG. 66, elongated members 422 and 424 include elongated rails or guides 425 that assist the surgeon in guiding an implant component into the implant. Rails or guides 425 may be located on the upper surface of lower elongated member 424 and on the lower surface of upper elongated member 422 to guide a component along elongated members 422 and 424 and assist the surgeon during insertion of, for example, an intermediate spacer member of an implant. As shown, the rails may be dovetailed and be adapted to receive a dovetail on an implant component, for example, the dovetail 171 shown in FIGS. 35 and 36.

In one aspect, the alignment mechanism, such as, guides 425, may also function to confirm that the correct sizing of the distracted gap or separation 438 that the instrument 420 has created. That is, the intermediate spacer member may mate with both of the top and bottom alignment mechanisms, for example, guides or dovetails 425, and by doing so confirm that the top elongated member 422 and the bottom elongated member 424 are correctly spaced apart.

Figure 67:
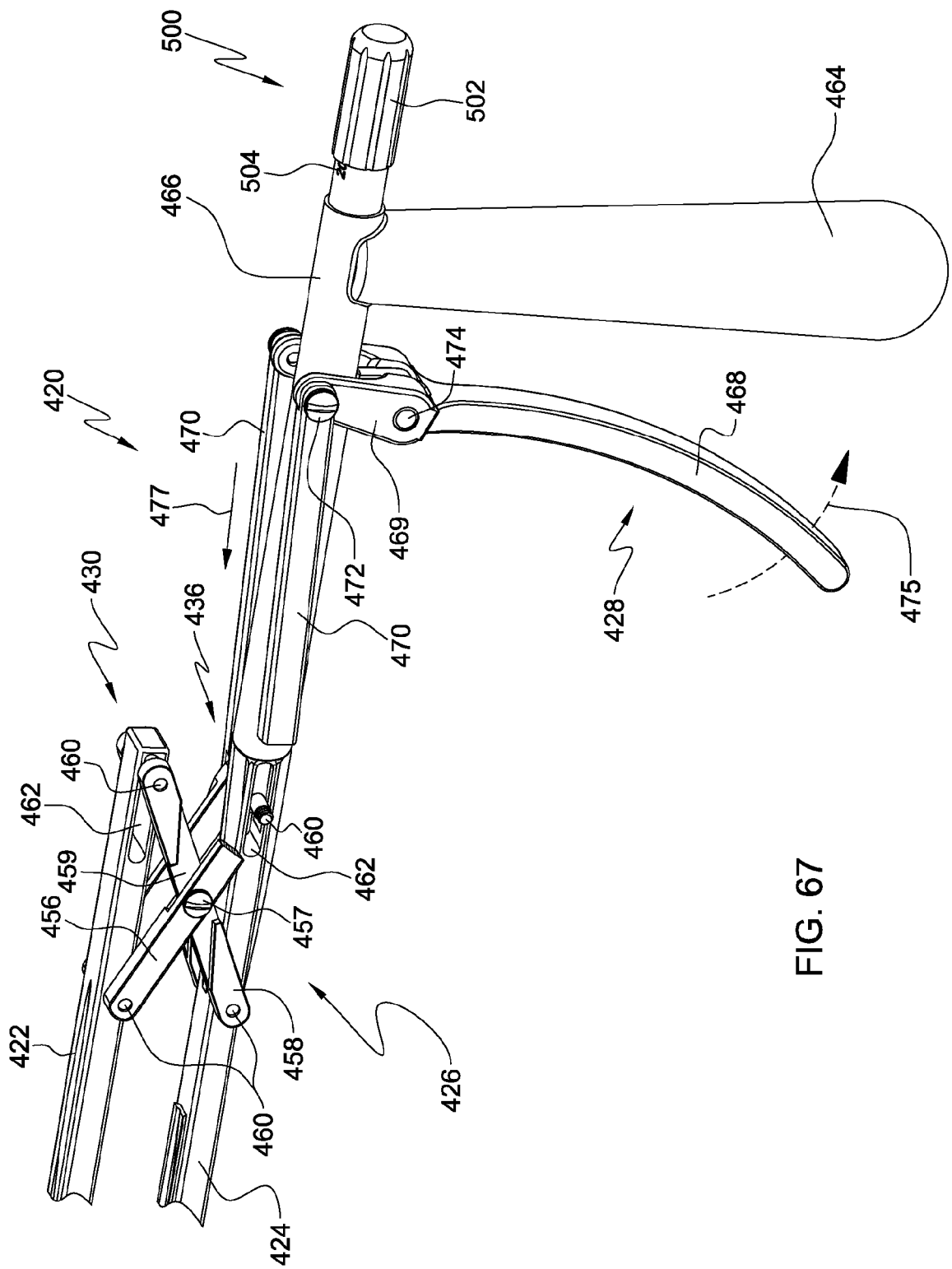
FIG. 67 is a detailed perspective view, partially in cross section, of the distal end of the distraction tool shown in FIG. 62.

FIG. 67 is a detailed perspective view, partially in cross section, of the distraction mechanism 426 of the distraction tool 420 shown in FIG. 62, according to one aspect of the invention. In FIG. 67, link 456 and rod 470 are sectioned to expose details of aspects of the invention. According to aspects of the invention, distraction mechanism 426 is configured to allow a surgeon to manipulate or vary the separation 438 (see FIGS. 63 and 64) between elongated members 422 and 424, and, accordingly, "distact" the two tissue surfaces against which the implant components mounted to the proximal ends 432, 436, of elongated members 422, 424, respectably, bear. In one aspect of the invention, any appropriate distraction mechanism 426 may be used to provide this function, for example, any combination of levers, cams, gears, or other devices or mechanisms that can effect the desired distraction may be used. In the aspect of the invention shown in FIG. 67, distraction mechanism 426 comprises at least one pair of links 456, 458 pivotally mounted to the distal ends 430, 434 of elongated members 422 and 424, respectively. Though one or more sets of links 456, 458 may be used to provide the desired function, two sets of links 456, 458 pivotally mounted to opposite sides of elongated members 422 and 424 by fasteners or pins 460 are provided in the aspect shown in FIG. 67. Links 456, 458 may be pivotally mounted to each other by fastener 457, for example, a screw, a bold, a rivet or a pin, and may include at least one recess 459 to minimize the assembled width of links 456, 458; recess 459 may also limit the rotation of links 456, 458 about fastener 457.

According to the aspect of the invention shown in FIG. 67, links 456, 458 may also be slidably mounted to elongated members 422 and 424. For example, the distal ends 430 and 434 of elongated members 422 and 424, respectively, may include elongated slots 462 positioned and adapted to receive pins 460 and allow longitudinal translation of pins 460 and links 456, 458 along elongated members 422 and 424.

According to aspects of the invention, distraction mechanism 426 is actuated by actuator 428. Again, though any type of manual or automated actuators may be used to actuate distraction mechanism 426, in the aspect of the invention shown in FIG. 67, actuator 428 may include a stationary hand grip 464 mounted to a support member 466, for example, a bar, rod or tube, and a rotatable hand lever 468 pivotally mounted to support member 466 and also pivotally mounted to one or more actuation rods 470. Hand grip 464 may be shaped and made from a material to enhance the grip of the surgeon while providing a comfortable, ergonomic design. Hand grip 464 may have at least an elastomeric surface to enhance the grip, for example, a silicone based elastomer may be used. In one aspect, support member 466 may comprise an extension to elongated member 424. In another aspect, elongated member 424 may be mounted to support member 466. As shown in FIG. 67, hand lever 468 may have a forked extension 469 which is pivotally mounted to support member 466 by screw or pin 474, for example, mounted to projection from support member 466, and pivotally mounted to actuator rod 470 by screw or pin 472. Actuator rods 470 may be mounted for axial translation about or within support member 466, for example, inside a hollow tube. As shown by the partial cut-away in FIG. 67, actuator rod 470 may be operatively connected to a detraction mechanism 426, for example, to link 456, by fastener or pin 460, and pin 460 may be adapted to translate within slot 462. Though not shown in FIG. 67, in one aspect, the distal ends 430, 434 of elongated members 422, 424, respectively, may include elongated slots, for example, to allow unencumbered translation of actuator rod 470 within the slots.

According to the aspect of the invention shown in FIG. 67, with the rotation of hand lever 468 about pin 474, for example, in the direction of arrow 475, the moment arm between pin 472 and pin 474 induces a translation of actuator rod 470, for example, in the direction of arrow 477, and a translation of pin 460 in slot 462. The translation of pin 460 in slot 462 translates the lower end of link 456 and, due to the pivotal mounting of link 456 to link 458 by fastener 457 and the pivotal mounting of links 456 and 458 to elongated members 422 and 424 by pins 460, results in an increase in the distance 438 between elongated members 422 and 424. Similarly, the rotation of hand lever 468 about pin 474 in the direction of opposite to the direction of arrow 475 results in a decrease of the distance 438 between elongated members 422 and 424.

FIG. 67 also illustrates certain features of the present invention that enhance operation or facilitate use by the surgeon. For example, the translation of actuator rod 470 may be biased by the presence of one or more springs (not shown). According to another aspect of the invention, an indication of the spacing 438 between elongated members 422 and 424 may be provided to the surgeon by one or more user-readable indicia. For example, elongated members 422 and 424 may be provided with a scale (not shown) having at least one translatable element that indicates the spacing 438 with movement of elongated members 222 and 224. An example of one such scale is shown in FIGS. 53 and 55.

Insertion tool 420 may also include means for locking the relative positions of elongated members 422 and 424, for example, to maintain a desired distraction distance. In one aspect of the invention, actuation mechanism 428 may include a locking mechanism 500, for example, an internally threaded and externally knurled locking collar or knob 502 which mechanically restricts the movement of actuator rod 470 or substantially prevents the movement of actuator rod 470, and links 456 and 458 to "lock" the positioning of elongated members 422 and 424 to maintain the separation 438. Accordingly, in this aspect, the surgeon or instrument operator does not have to continuously hold or depress the actuator 468 to maintain a set gap 438 between the elongated members 422 and 424. Other locking mechanisms can also be provided within the scope of this invention. In addition, the knob or collar 502, for example, a space indicator knob, may be provided with an indicator that cooperates with human readable indicia or discrete distance markings 504 on the outer surface of support member 466 to indicate the separation 438.

As discussed above with respect to coupling device 442, in another aspect of the invention, the coupling device 442 on the proximal ends 432, 434 of elongated members 422 and 424, respectively, may be actuated remotely, for example, by means of one or more elongated rods 429 (see FIG. 66). Rods 429 may be inserted into the proximal end 432, 434 from the distal end 430, 434 of elongated members 422 and 424. According to aspects of the invention, the coupling mechanism 442, for example, a threaded projection 444, on the proximal ends 432, 434 of elongated members 422 and 424, respectively, can be actuated, for example, rotated, by rotating the distal end of rods 429 accessible from the distal ends 430 and 434 of elongated members 422 and 424, respectively. Accordingly, in aspects of the invention, components of implants being inserted using tool 420 can be engaged and disengaged, for example, threaded and unthreaded, by remotely rotating rods 429.

Distraction tool 420 may be fabricated from metals and/or non-metals. For example, in one aspect, distraction tool 420 may be metallic, for example, made from any metal that is resistant to corrosion when exposed to bodily fluids, such as, stainless steel or titanium. In another aspect, distraction tool 420 may be non-metallic, for example, made from a plastic that is resistant to attack when exposed to bodily fluids, such as, PEEK, PTFE, or their equivalents. In one aspect, distraction tool 420 may typically be made from FDA approved implant grade materials, such as, implant grade titanium and/or implant stainless steel, or implant grade plastics, such as, PEEK.

Aspects of the invention also include the method or surgical technique for implantation of a tissue spacer implant, such as, implant 10 and 110. Though some features of this procedure, for example, appropriate tissue exposure and dissection techniques, are well known in the art, aspects of the present invention provide novel techniques. In one aspect, a method is provided which includes obtaining an implant 10, 110 and surgical instrument 210, 420 that include a first elongated member 222, 422 having a distal end and a proximal end adapted to receive a first end member of an implant; a second elongated member 224, 424 having a distal end and a proximal end adapted to receive a second end member of the implant; a distraction mechanism 226, 426 operatively connected to the first elongated member and the second elongated member, the distraction mechanism adapted to vary a separation between the first elongated member and the second elongated member; and an actuator 228, 428 operatively connected to the distraction mechanism and adapted to manipulate the distraction mechanism; mounting a least one component of the implant 10, 110 to the proximal ends of the elongated members 224, 424; and then inserting the at least one component of the implant 10, 110 between tissue bodies with the surgical instrument 10, 110. It should be understood that all of the above noted instrument components and respective elements include the same structural and functionality characteristics as described previously herein.

A possible further step of the method may include actuation of the distraction mechanism 226, 426 to either increase the space 238, 438 between the two tissue bodies or alternatively, maintain the existing space. Following this process, the next step may be to place the intermediate spacer member 20, 216 along the alignment mechanism, for example, dovetails or channels, of the top and bottom elongated members 224, 424 and slide the appropriate sized intermediate spacer member 20, 216 into the existing space between the end members 12, 14, 212, 214. The method may include the further step of securing the intermediate spacer member 20, 216 to the end members 12, 14, 212, 214 and then releasing the instrument 210, 420 from the end members and thereby allowing the extraction of the instrument 210, 420 from the incision site.

It should be understood by those skilled in the art that the surgical method and use of the surgical instrument 210, 420 described herein may be performed using either anterior, posterior or lateral approaches to the surgical site, including for example the spinal column. In addition, an operating surgeon may use a minimally invasive surgical approach and employ the surgical instrument 210, 420 because of the multi-functionality (that is, grasp and gap distraction/maintenance) operation of surgical instrument 210, 420 relative to implant 10, 110. It is further contemplated that the surgical instrument 210, 420 may be sized to allow for endoscopic insertion. Having these multiple functions incorporated into one instrument addresses a long felt need of providing the operating surgeon with the ability to keep one instrument in the wound and to not have to repeatedly remove the instrument and replace it with a different instrument to perform another function. Having a multi-purpose surgical instrument will lessen the potential for tissue disruption and adjacent structural damage.

It is contemplated that a method of fabricating the surgical instrument 210, 420 may include the steps of providing elongated members 222, 224, 422, 424 with a distraction mechanism 226, 426, and actuator 228, 428.

The fabrication method may also include the further step of providing top and bottom elongated members 222, 224, 422, 424 having implant engagement ends, and to couple a distraction mechanism 226, 426 to these elongated members that will typically allow the operating surgeon to adjust the distance 238, 438 between the implant engagement ends while holding the end members of the implant 10, 110 in place while positioned within a space between two tissue bodies. Yet a further step of the fabrication method may include providing a space indicator that permits the operating surgeon with the ability to determine the resultant distraction distance 238, 428 as well as securing and fixing the space between the implant engagement. Following this step, the overall length and position of the implant is finalized in vivo.

It is also contemplated that a tissue spacer implant insertion kit that includes various cross-sectional sizes and shapes and longitudinal lengths of end members 12, 14, 212, 214 and intermediate spacer members 20, 216 and a corresponding surgical instrument 210, 420 are provided. This will allow the operating surgeon to pick and choose the modular components that are necessary to assemble a tissue spacer implant that best fits the presented clinical situation or to address a certain anatomical deformity found in a patient. The kit may further include an inserter instrument 210, 420 that may be used with the multiple sized (both length and diameter) tissue spacer implants, including for example, spinal implants. It is also contemplated that multiple sized distractors/inserter instruments 210, 420 may be included in the kit to accommodate the various anatomic regions of the body, including the spine and the corresponding implant sizes (that is, lumbar, thoracic and cervical). Kits according to aspects of the invention may include an enclosure adapted to retain elements of the kit and an instruction manual describing and/or illustrating proper use, care, and maintenance of the kit and the elements in the kit. The distractor/inserter instrument 210, 420 may typically include the above described elements and components that, for the sake of brevity sake, will not be discussed again here, and include the same structural and functionality characteristics as described previously herein.

Although the various embodiments have been depicted and described in detail herein, it will be apparent to those skilled in the relevant art that additional modifications, and substitutions can be made without departing from its essence and therefore these are to be considered to be within the scope of the following claims.

What is claimed is:

1. A vertebral body replacement implant comprising:
 a first end member having a first end configured to engage tissue and a second end opposite the first end;
 a second end member having a first end configured to engage tissue and a second end opposite the first end;
 an intermediate spacer member having a main body and a coupling mechanism, the coupling mechanism comprising a first pair of projections and a second pair of projections,
  wherein the first pair of projections are adapted to slidably engage a recess of the second end of the first end member to secure the first end member and the main body of the intermediate spacer member along a longitudinal axis of the implant extending through the first end of the first end member and the first end of the second end member, and
  wherein the second pair of projections are adapted to slidably engage a recess of the second end of the second end member to secure the second end member and the main body of the intermediate spacer member along the longitudinal axis of the implant; and
 a deflecting member configured to deflect at least one of the projections of the first pair of projections with respect to the other projection of the first pair of projections to exert a contact force between the projections and the recess of the first end member to rigidly fix the intermediate spacer member and the first end member, and at least one of the projections of the second pair of projections with respect to the other projection of the second pair of projections to exert a contact force between the intermediate spacer member and the recess of the second end member to rigidly fix the intermediate spacer member and the second end member.

2. The vertebral body replacement implant as recited in claim 1, wherein the deflecting member deflects both of the projections of the first and the second pair of projections.

3. The vertebral body replacement implant as recited in claim 1, wherein the first pair of projections is shaped to fit within the recess in the second end of the first end member and the second pair of projections is shaped to fit within the recess in the second end of the second end member.

4. The vertebral body replacement implant as recited in claim 1, wherein each of the first pair of projections are beveled and the recess in the second end of the first end member is beveled, and wherein each of the second pair of projections are beveled and the recess in the second end of the second end member is beveled.

5. The vertebral body replacement implant as recited in claim 1, wherein the first pair of projections form a first dovetail-shaped projection and the recess of the second end of the first end member comprises a first dovetail-shaped recess such that the first dovetail-shaped projection and the first dovetail-shaped recess are adapted to slidably engage along a lateral axis extending substantially perpendicular to the longitudinal axis, and the second pair of projections form a second dovetail-shaped projection and the recess of the second end of the second end member comprises a second dovetail-shaped recess such that the second dovetail-shaped projection and the second dovetail-shaped recess are adapted to slidably engage along the lateral axis.

6. The vertebral body replacement implant as recited in claim 5, wherein an outer longitudinal end of the first dovetail-shaped projection defines a lateral dimension that is larger than a lateral dimension of an outer longitudinal end of the first dovetail-shaped recess such that, when engaged, the first dovetail-shaped projection is prevented from translating longitudinally out from within the first dovetail-shaped recess.

7. The vertebral body replacement implant as recited in claim 1, wherein the main body of the intermediate spacer member comprises a main body having a longitudinally extending separation, and wherein the deflecting member comprises a separation widening device adapted to be inserted into the longitudinally extending separation and to deform the main body to widen the longitudinally extending separation such that the projections of the first pair of projections and the projections of the second pair of projections are deflected away from each other.

8. The vertebral body replacement implant as recited in claim 7, wherein the separation widening device comprises a wedge or a threaded rod.

9. The vertebral body replacement implant as recited in claim 1, wherein at least one of projections of the first pair of projections of the coupling mechanism comprises a portion of a first coupling plate coupled to the intermediate spacer member and the other projection of the first pair of projections extends from the main body, and wherein at least one of projections of the second pair of projections of the coupling mechanism comprises a portion of a second coupling plate coupled to the intermediate spacer member and the other projection of the second pair of projections extends from the main body; and wherein the deflecting member is configured to deflect the first coupling plate and the second coupling plate with respect to the intermediate spacer member.

10. The vertebral body replacement implant as recited in claim 9, wherein the deflecting member comprises a camming device adapted to be inserted longitudinally at least partially between the first coupling plate and the second coupling plate to force the first coupling plate and the second coupling plate toward each other along the longitudinal axis.

11. The vertebral body replacement implant as recited in claim 10, wherein the camming device comprises one of a tapered rod, a wedge, and a threaded rod.

12. The vertebral body replacement implant as recited in claim 10, wherein the camming device comprises a tapered rod threaded into the main body of the intermediate spacer member.

13. The vertebral body replacement implant as recited in claim 1, wherein the vertebral body replacement implant further comprises a first footplate mounted to the first end of the first end member and a second footplate mounted to the first end of the second end member.

14. The vertebral body replacement implant as recited in claim 1, wherein the coupling mechanism is adapted to substantially simultaneously rigidly fix the first end member with the intermediate spacer member and the second end member with the intermediate spacer member.

15. The vertebral body replacement implant as recited in claim 1, wherein the recess of the second end of the first end member extends towards, and terminates before, the first end thereof, and the recess of the second end of the second end member extends towards, and terminates before, the first end thereof.

16. The vertebral body replacement implant as recited in claim 1, wherein when the first pair of projections engage the recess of the second end of the first end member, the first pair of projections extends towards, and terminates before, the first end of the first end member, and wherein when the second pair of projections engage the recess of the second end of the second end member, the second pair of projections extends towards, and terminates before, the first end of the second end member.

17. The vertebral body replacement implant as recited in claim 1, wherein the first end member, the second end member, and the intermediate spacer member each define a substantially cylindrical shape.

18. The vertebral body replacement implant as recited in claim 1, wherein the main body of the intermediate spacer member is of one-piece construction, and wherein one of the projections of each of the first and second pairs of projections of the coupling mechanism is a portion of the main body.

19. The vertebral body replacement implant as recited in claim 1, wherein the main body of the intermediate spacer member is hollow.

20. The vertebral body replacement implant as recited in claim 1, wherein, when the deflecting member deflects at least one of the projections of the first pair of projections and at least one of the projections of the second pair of projections with respect to the other projection of the respective pair of projections, the first end member and the second end member are rigidly fix to each other via the intermediate spacer member.

21. A vertebral body replacement implant comprising:
a first end member having a first end configured to engage tissue and a second end substantially opposing the first end;
a second end member having a first end configured to engage tissue and a second end substantially opposing the first end;
an intermediate spacer member having a first coupling end adapted to engage with the second end of the first end member and a second coupling end adapted to engage with the second end of the second end member;
a first coupling plate adapted to engage the second end of the first end member;
a second coupling plate adapted to engage the second end of the second end member; and
a deflection mechanism configured to couple to the intermediate spacer member and deflect the first coupling plate with respect to at least the first coupling end of the intermediate spacer member and the second coupling plate with respect to at least the second coupling end of the intermediate spacer member when the first coupling plate is engaged with the first end member and the second coupling plate is engaged with the second end member such that, upon deflection of the first coupling plate with respect to at least the first coupling end and the second coupling plate with respect to at least the second coupling end due at least in part to inserting the deflection mechanism into the first coupling plate and the second coupling plate, the first coupling plate engages and exerts a contact force between the first coupling plate and the second end of the first end member to rigidly fix the first end member to the intermediate spacer member, and the second coupling plate engages and exerts a contact force between the second coupling plate and the second end of the second end member to rigidly fix the second end member to the intermediate spacer member.

22. The vertebral body replacement implant as recited in claim 21, wherein the intermediate spacer member comprises a hollow main body, and wherein the first coupling plate and the second coupling plate are positioned at least partially within the hollow main body of the intermediate spacer member.

23. The vertebral body replacement implant as recited in claim 21, wherein the deflection mechanism comprises a camming device having a camming surface adapted to contact and deflect the first coupling plate and the second coupling plate toward each other along a longitudinal axis of the implant extending through the first end of the first end member and the first end of the second end member.

24. The vertebral body replacement implant as recited in claim 23, wherein the camming device comprises a cylindrical body and the camming surface comprises a beveled surface on the cylindrical body.

25. The vertebral body replacement implant as recited in claim 24, wherein the cylindrical body comprises a circular cylindrical body and the camming surface comprises a circular frustum of varying diameter.

26. The vertebral body replacement implant as recited in claim 23, wherein the camming device comprises a translatable camming device that moves along a lateral axis that is angled with respect to the longitudinal axis.

27. The vertebral body replacement implant as recited in claim 26, wherein the camming device comprises an external screw thread on the camming device, the external screw thread adapted to rotate within an internally threaded aperture and move the camming device along the lateral axis.

28. The vertebral body replacement implant as recited in claim 21, wherein the first coupling plate and the second coupling plate are separate and distinct components with respect to the intermediate spacer member.

29. The vertebral body replacement implant as recited in claim 21, wherein the first and second coupling plates each include a projection, and the first end member and the second end member include recesses corresponding to the first and second coupling plates, respectively.

30. The vertebral body replacement implant as recited in claim 29, wherein the projection of the first coupling plate is positioned within the corresponding recess of the first end member when the first coupling plate is engaged with the first end member, and wherein the projection of the second coupling plate is positioned within the corresponding recess of the second end member when the second coupling plate is engaged with the second end member.

31. The vertebral body replacement implant as recited in claim 30, wherein upon deflection of the first coupling plate with respect to at least the first coupling end of the intermediate spacer member and the second coupling plate with respect to at least the second coupling end of the intermediate spacer member, the projection of the first coupling plate engages the recess of the first end member and exerts a contact force between the second end of the first end member and the first coupling end of the intermediate spacer member to rigidly fix the first end member to the intermediate spacer member, and the projection of the second coupling plate engages the recess of the second end member and exerts a contact force between the second end of the second end member and the second coupling end of the intermediate spacer member to rigidly fix the second end member to the intermediate spacer member.

32. The vertebral body replacement implant as recited in claim 21, wherein at least a portion of the first coupling plate is positioned between the intermediate spacer member and the first end member, and at least a portion of the second coupling plate is positioned between the intermediate spacer member and the second end member.

* * * * *